United States Patent [19]
Niwa et al.

[11] Patent Number: 5,648,250
[45] Date of Patent: Jul. 15, 1997

[54] TISSUE PLASMINOGEN ACTIVATOR

[75] Inventors: Mineo Niwa, Muko; Yoshimasa Saito, Osaka; Hitoshi Sasaki, Amagasaki; Masako Hayashi; Jouji Notani, both of Takatsuki; Masakazu Kobayashi, Ikeda, all of Japan

[73] Assignee: Fujisawa Pharmaceutical Co., Ltd., Osaka, Japan

[21] Appl. No.: 412,859

[22] Filed: Mar. 29, 1995

Related U.S. Application Data

[63] Continuation of Ser. No. 238,796, May 6, 1994, abandoned, which is a continuation of Ser. No. 131,672, Oct. 5, 1993, abandoned, which is a continuation of Ser. No. 991,714, Dec. 16, 1992, abandoned, which is a continuation of Ser. No. 879,736, May 6, 1992, abandoned, which is a continuation of Ser. No. 711,410, Jun. 5, 1991, abandoned, which is a continuation of Ser. No. 227,149, Aug. 2, 1988, abandoned.

[30] Foreign Application Priority Data

| Aug. 3, 1987 | [GB] | United Kingdom | 8718298 |
| Oct. 26, 1987 | [GB] | United Kingdom | 8725052 |
| Nov. 13, 1987 | [GB] | United Kingdom | 8726683 |

[51] Int. Cl.⁶ ............ C12N 15/70; C12N 15/58; C07H 21/04; A61K 38/49
[52] U.S. Cl. ............ 435/172.3; 435/212; 435/320.1; 536/23.2; 514/12
[58] Field of Search ............ 435/212, 320.1, 435/172.3; 536/23.2; 514/12

[56] References Cited

FOREIGN PATENT DOCUMENTS

| 0093619 | 11/1983 | European Pat. Off. | C12N 15/00 |
| 0199574 | 10/1986 | European Pat. Off. | C12N 15/00 |
| 0196920 | 10/1986 | European Pat. Off. | C12N 9/72 |
| 8401786 | 5/1984 | WIPO | C12N 9/64 |

OTHER PUBLICATIONS van Zonneveld et al. (1986), Proc. Natl. Acad. Sci. USA 83:4670–4674.

*Primary Examiner*—Mindy Fleischer
*Assistant Examiner*—Nancy J. Degen
*Attorney, Agent, or Firm*—Oblon, Spivak, McClelland, Maier & Neustadt, P.C.

[57] ABSTRACT

The invention relates to a new tissue plasminogen activator which has strong activity for converting plasminogen into plasmin that degrades the fibrin network of blood clots to form soluble products and therefore is useful as a thrombolytic agent. The invention also relates to a DNA sequence encoding the amino acid sequence for the tissue plasminogen activator, to a process for producing the plasminogen activator, and to a pharmaceutical composition comprising the new tissue plasminogen activator.

17 Claims, 58 Drawing Sheets

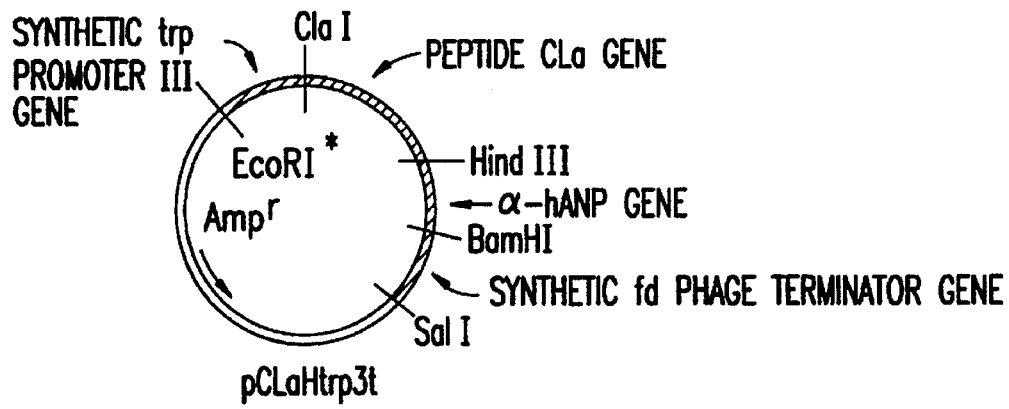
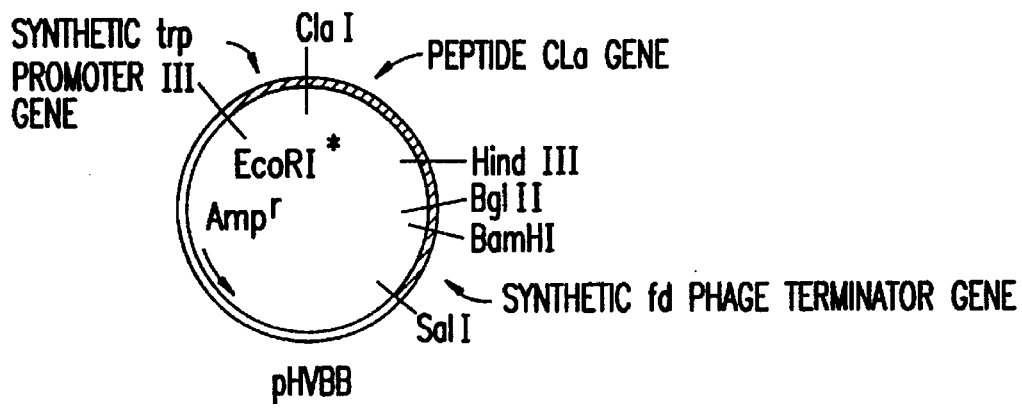
FIG.1

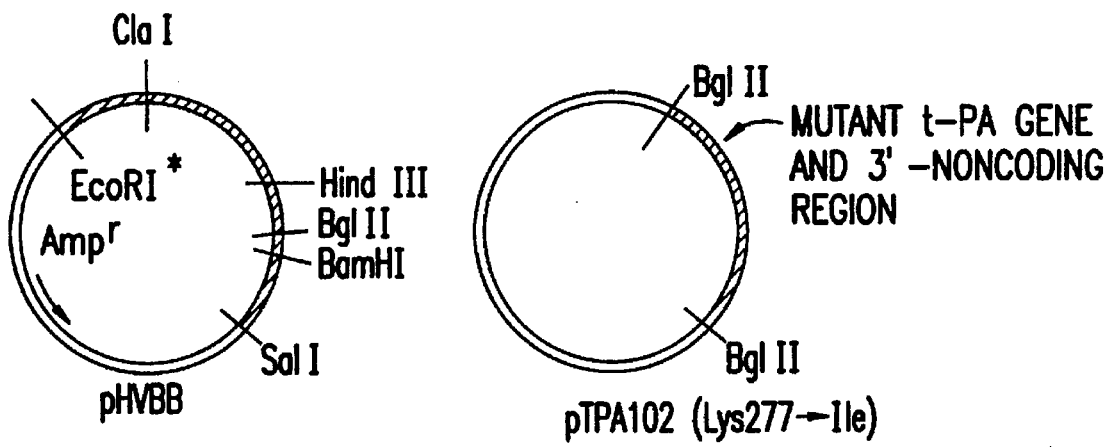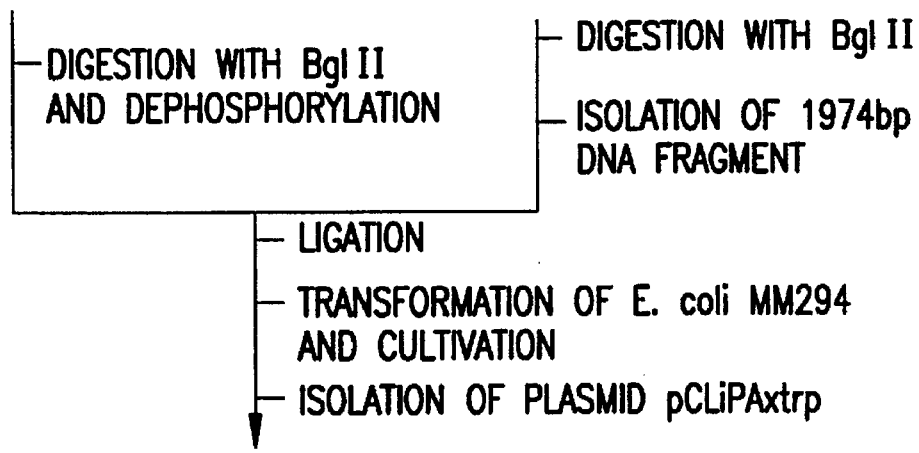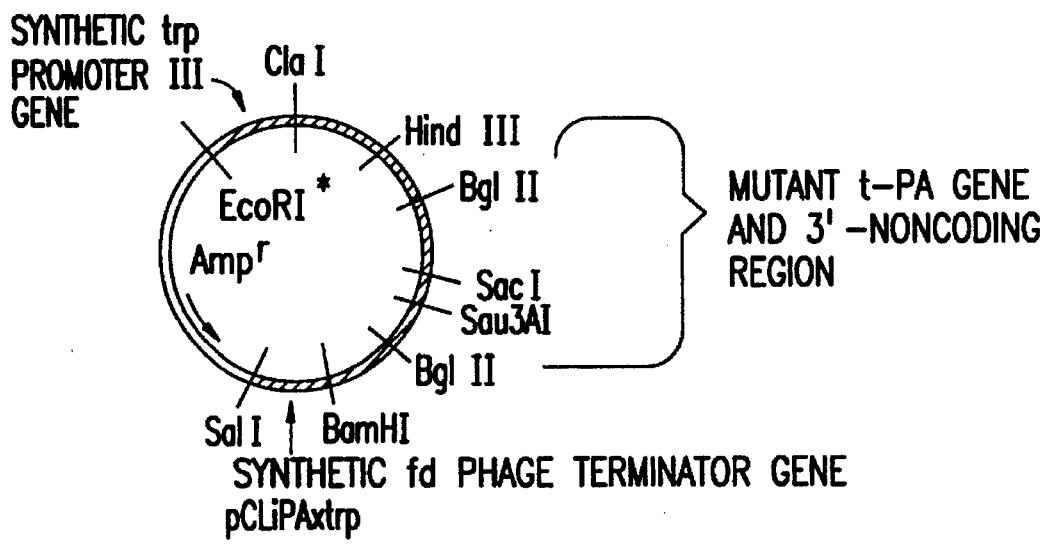
FIG.2

(BgI II)
Coding chains:5'- GATCTTACCAAGTGATCTGCAGAGATGAAAAAACGCAGATGATATACCAG
                 SerTyrGlnValIleCysArgAspGluLysThrGlnMetIleTyrGln
                 |→ Mutant t-PA                  10

CAACATCAGTCATGGCTGCGCCCTGTGCTCAGAAGCAACCGGGTGGAATATTGCTGGTGC
GlnHisGlnSerTrpLeuArgProValLeuArgSerAsnArgValGluTyrCysTrpCys
          20                                30

AACAGTGGCAGGGCACAGTGCCACTCAGTGCCTGTCAAAAGTTGCAGCGAGCCAAGGTGT
AsnSerGlyArgAlaGlnCysHisSerValProValLysSerCysSerGlyProArgCys
          40                                50

TTCAACGGGGGCACCTGCCAGCAGGCCCTGTACTTCTCAGATTTCGTGTGCCAGTGCCCC
PheAsnGlyGlyThrCysGlnGlnAlaLeuTyrPheSerAspPheValCysGlnCysPro
          60                                70
                                                   (AvaII)
GAAGGATTTGCTGGGAAGTGCTGTGAAATAGATACCAGGGCCACGTGCTACGAGGACCAG
GluGlyPheAlaGlyLysCysCysGluIleAspThrArgAlaThrCysTyrGluAspGln
          80                                90
                                                   (BbeI)
GGCATCAGCTACAGGGGCACGTGGAGCACAGCGGAGAGTGGCGCCGAGTGCACCAACTGG
GlyIleSerTyrArgGlyThrTrpSerThrAlaGluSerGlyAlaGluCysThrAsnTrp
          100                               110

AACAGCAGCGCGTTGGCCCAGAAGCCCTACAGCGGGCGGAGGCCAGACGCCATCAGGCTG
AsnSerSerAlaLeuAlaGlnLysProTyrSerGlyArgArgProAspAlaIleArgLeu
          120                               130

GGCCTGGGGAACCACAACTACTGCAGAAACCCAGATCGAGACTCAAAGCCCTGGTGCTAC
GlyLeuGlyAsnHisAsnTyrCysArgAsnProAspArgAspSerLysPorTrpCysTyr
          140                               150
                                                   (DdeI)
GTCTTTAAGGCGGGGAAGTACAGCTCAGAGTTCTGCAGCACCCCTGCCTGCTCTGAGGGA
ValPheLysAlaGlyLysTyrSerSerGluPheCysSerThrProAlaCysSerGluGly
          160                               170

AACAGTGACTGCTACTTTGGGAATGGGTCAGCCTACCGTGGCACGCACAGCCTCACCGAG
AsnSerAspCysTyrPheGlyAsnGlySerAlaTyrArgGlyThrHisSerLeuThrGlu
          180                               190
                        (EcoRI)
TCGGGTGCCTCCTGCCTCCCGTGGAATTCCATGATCCTGATAGGCAAGGTTTACACAGCA
SerGlyAlaSerCysLeuProTrpAsnSerMetIleLeuIleGlyLysValTyrThrAla·
          200                               210

FIG.3A

```
CAGAACCCCAGTGCCCAGGCACTGGGCCTGGGCAAACATAATTACTGCCGGAATCCTGAT
GlnAsnProSerAlaGlnAlaLeuGlyLeuGlyLysHisAsnTyrCysArgAsnProAsp
          220                                230

GGGGATGCCAAGCCCTGGTGCCACGTGCTGAAGAACCGCAGGCTGACGTGGGAGTACTGT
GlyAspAlaLysProTrpCysHisValLeuLysAsnArgArgLeuThrTrpGluTyrCys
          240                                250

GATGTGCCCTCCTGCTCCACCTGCGGCCTGAGACAGTACAGCCAGCCTCAGTTTCGCATC
AspValProSerCysSerThrCysGlyLeuArgGlnTyrSerGlnProGlnPheArgIle
          260                                270

ATAGGAGGCCTCTTCGCCGACATCGCCTCCCACCCCTGGCAGGCTGCCATCTTTGCCAAG
IleGlyGlyLeuPheAlaAspIleAlaSerHisProTrpGlnAlaAlaIlePheAlaLys
          280                                290

CACAGGAGGTCGCCCGGAGAGCGGTTCCTGTGCGGGGGCATACTCATCAGCTCCTGCTGG
HisArgArgSerProGlyGluArgPheLeuCysGlyGlyIleLeuIleSerSerCysTrp
          300                                310

ATTCTCTCTGCCGCCCACTGCTTCCAGGAGAGGTTTCCGCCCCACCACCTGACGGTGATC
IleLeuSerAlaAlaHisCysPheGlnGluArgPheProProHisHisLeuThrValIle
          320                                330

TTGGGCAGAACATACCGGGTGGTCCCTGGCGAGGAGGAGCAGAAATTTGAAGTCGAAAAA
LeuGlyArgThrTyrArgValValProGlyGluGluGluGlnLysPheGluValGluLys
          340                                350
                (EcoRI)
TACATTGTCCATAAGGAATTCGATGATGACACTTACGACAATGACATTGCGCTGCTGCAG
TyrIleValHisLysGluPheAspAspAspThrTyrAspAsnAspIleAlaLeuLeuGln
          360                                370

CTGAAATCGGATTCGTCCCGCTGTGCCCAGGAGAGCAGCGTGGTCCGCACTGTGTGCCTT
LeuLysSerAspSerSerArgCysAlaGlnGluSerSerValValArgThrValCysLeu
          380                                390
                                         (Sac I)
CCCCCGGCGGACCTGCAGCTGCCGGACTGGACGGAGTGTGAGCTCTCCGGCTACGGCAAG
ProProAlaAspLeuGlnLeuProAspTrpThrGluCysGluLeuSerGlyTyrGlyLys
          400                                410

CATGAGGCCTTGTCTCCTTTCTATTCGGAGCGGCTGAAGGAGGCTCATGTCAGACTGTAC
HisGluAlaLeuSerProPheTyrSerGluArgLeuLysGluAlaHisValArgLeuTyr
          420                                430
```

FIG.3B

```
CCATCCAGCCGCTGCACATCACAACATTTACTTAACAGAACAGTCACCGACAACATGCTG
ProSerSerArgCysThrSerGlnHisLeuLeuAsnArgThrValThrAspAsnMetLeu
         440                          450

TGTGCTGGAGACACTCGGAGCGGCGGGCCCCAGGCAAACTTGCACGACGCCTGCCAGGGC
CysAlaGlyAspThrArgSerGlyGlyProGlnAlaAsnLeuHisAspAlaCysGlnGly
         460                          470

GATTCGGGAGGCCCCCTGGTGTGTCTGAACGATGGCCGCATGACTTTGGTGGGCATCATC
AspSerGlyGlyProLeuValCysLeuAsnAspGlyArgMetThrLeuValGlyIleIle
         480                          490

AGCTGGGGCCTGGGCTGTGGACAGAAGGATGTCCCGGGTGTGTACACAAAGGTTACCAAC
SerTrpGlyLeuGlyCysGlyGlnLysAspValProGlyValTyrThrLysValThrAsn
         500                          510

TACCTAGACTGGATTCGTGACAACATGCGACCGTGACCAGGAACACCCGACTCCTCAAAA
TyrLeuAspTrpIleArgAspAsnMetArgPro***|→  Noncoding (Sau3AI)
GCAAATGAGATCCCGCCTCTTCTTCTTCAGAAGACACTGCAAAGGCGCAGTGCTTCTCTA

CAGACTTCTCCAGACCCACCACACCGCAGAAGCGGGACGAGACCCTACAGGAGAGGGAAG

AGTGCATTTTCCCAGATACTTCCCATTTTGGAAGTTTTCAGGACTTGGTCTGATTTCAGG

ATACTCTGTCAGATGGGAAGACATGAATGCACACTAGCCTCTCCAGGAATGCCTCCTCCC

TGGGCAGAAGTGGCCATGCCACCCTGTTTTCGCTAAAGCCCAACCTCCTGACCTGTCACC

GTGAGCAGCTTTGGAAACAGGACCACAAAAATGAAAGCATGTCTCAATAGTAAAAGAAAC (Bgl II)
AAGA -3'
```

FIG. 3C

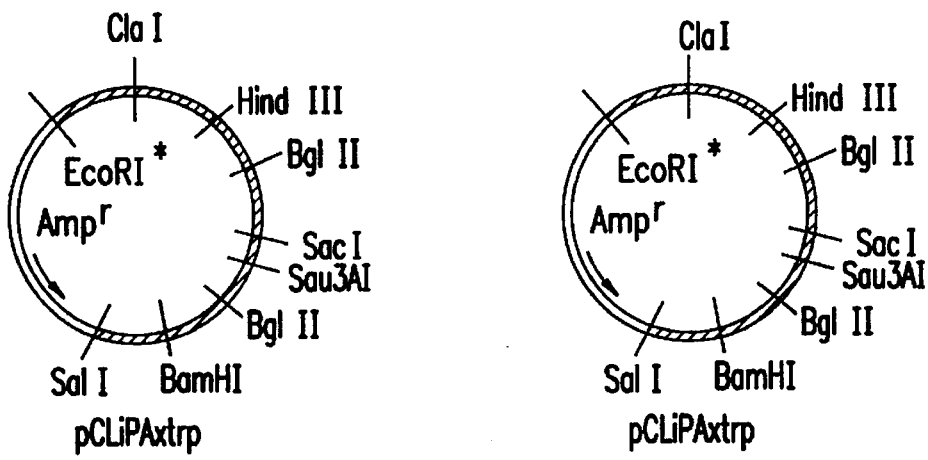
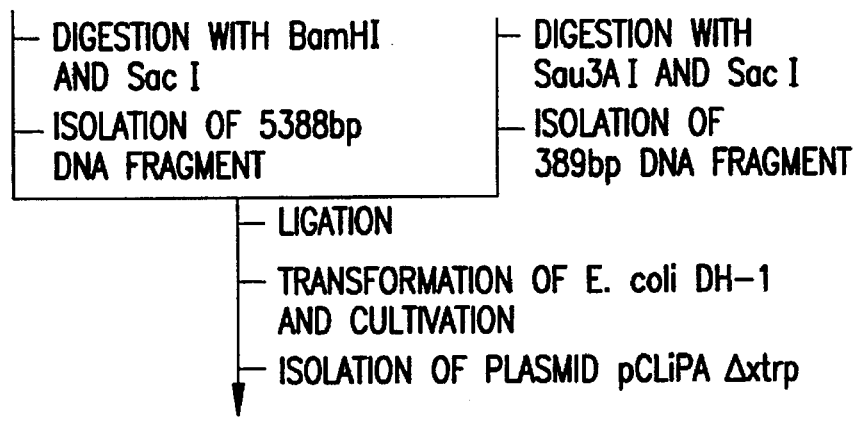
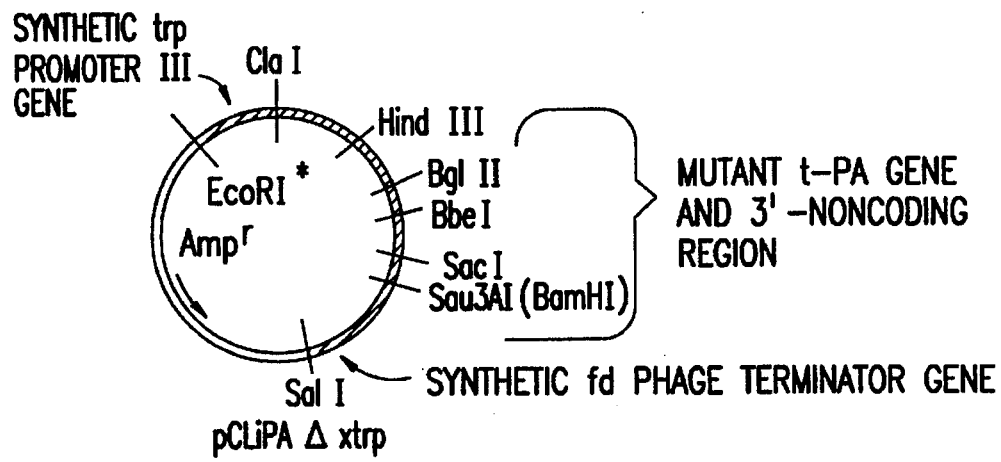
FIG.4

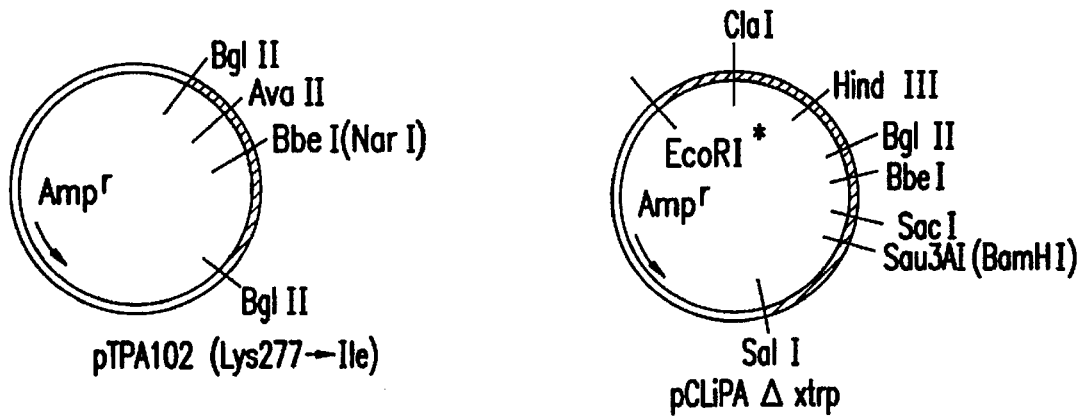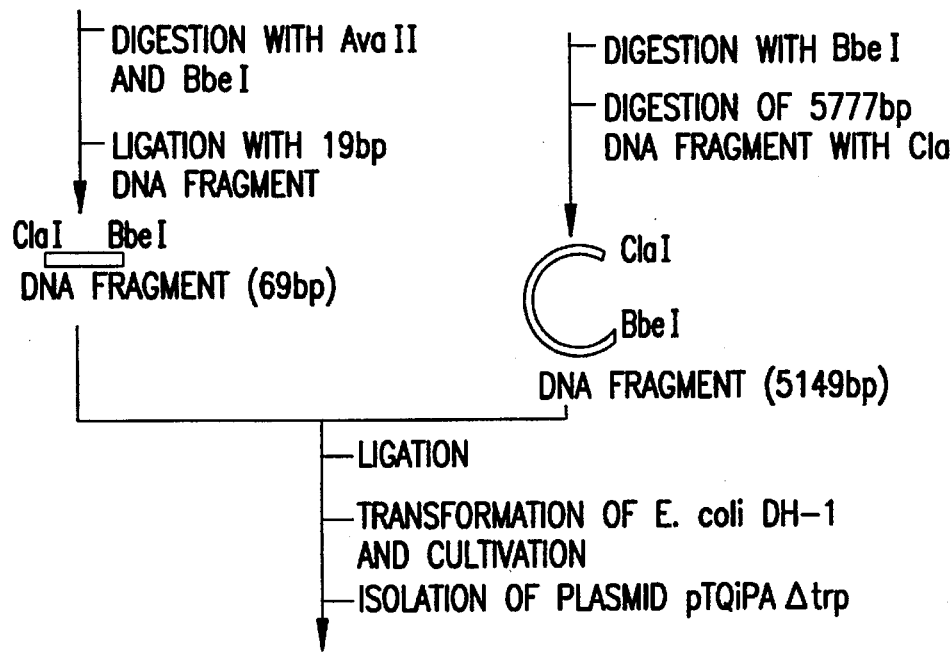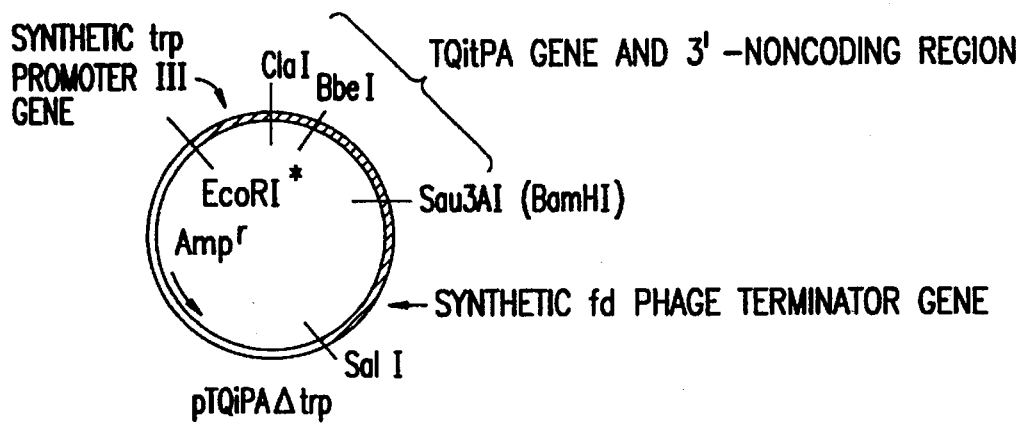
FIG.5

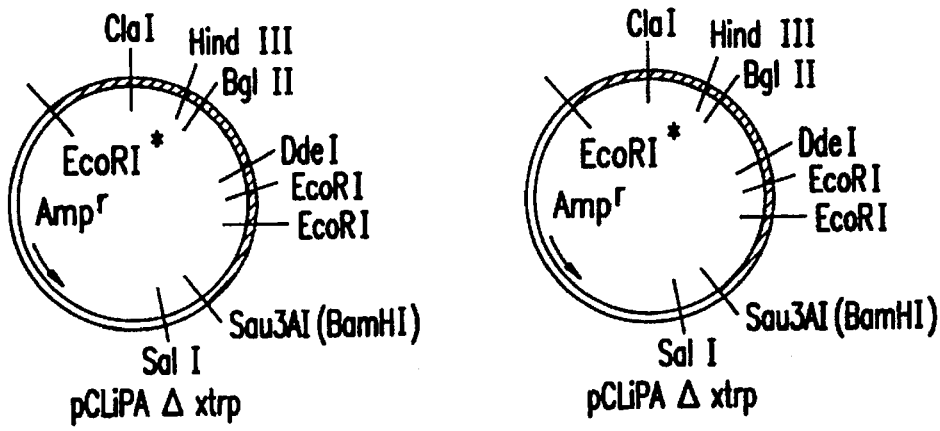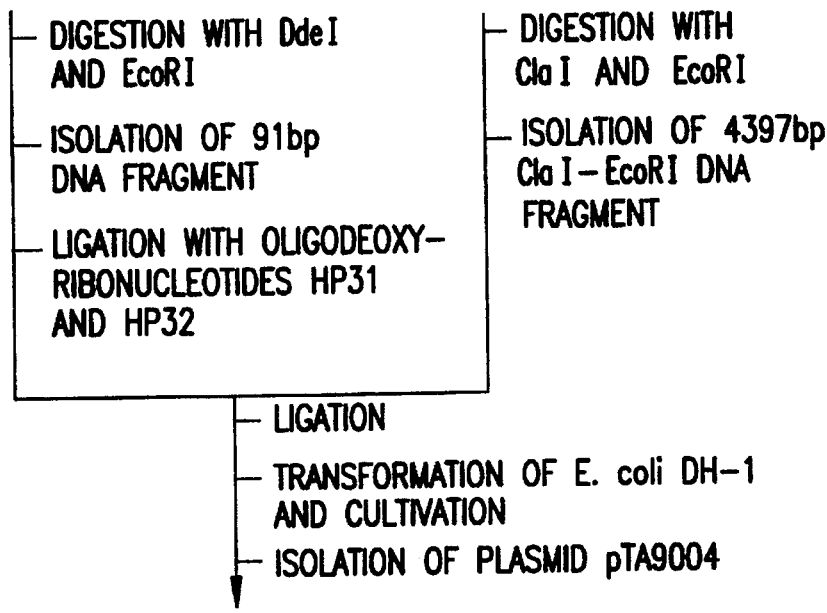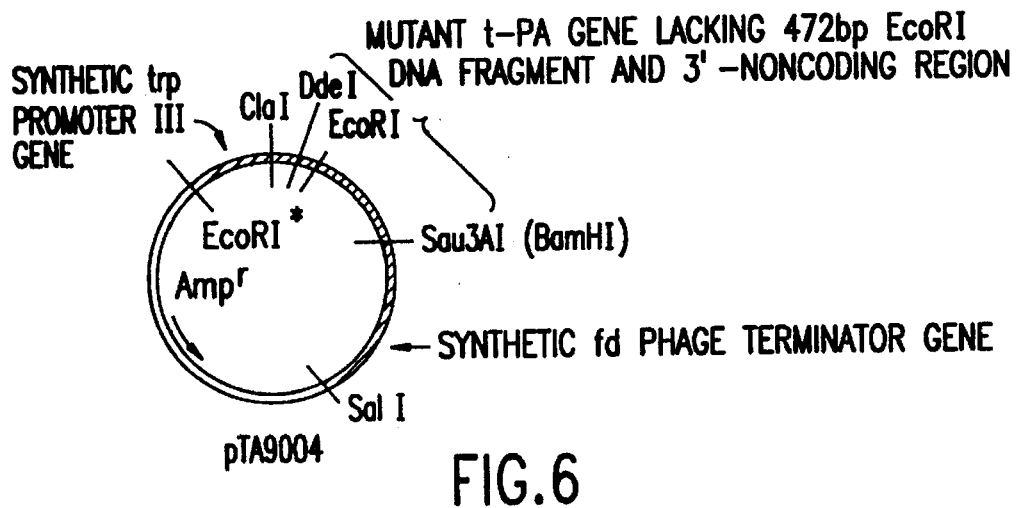
FIG.6

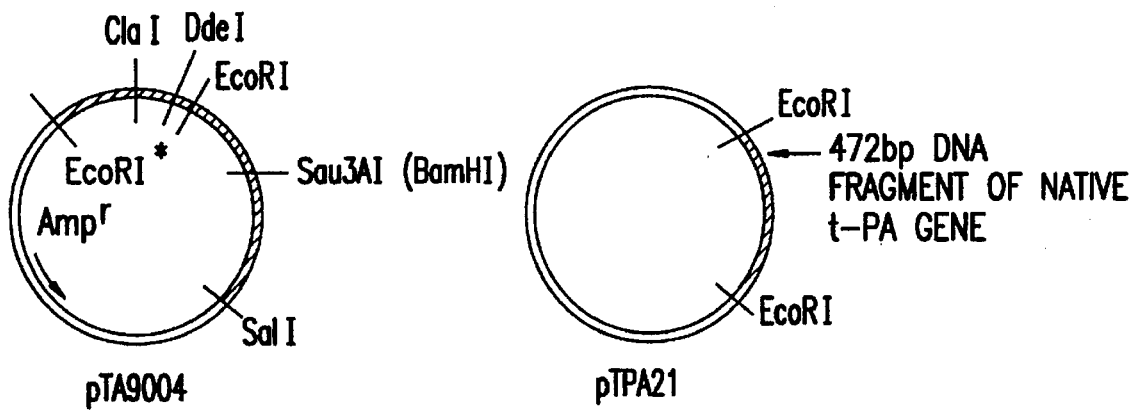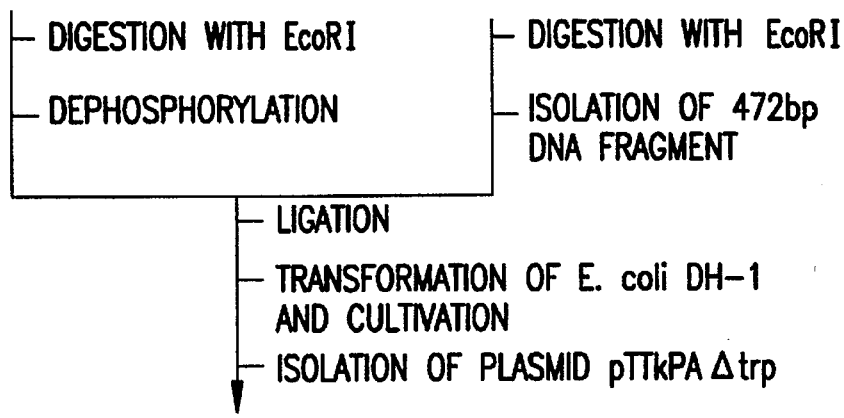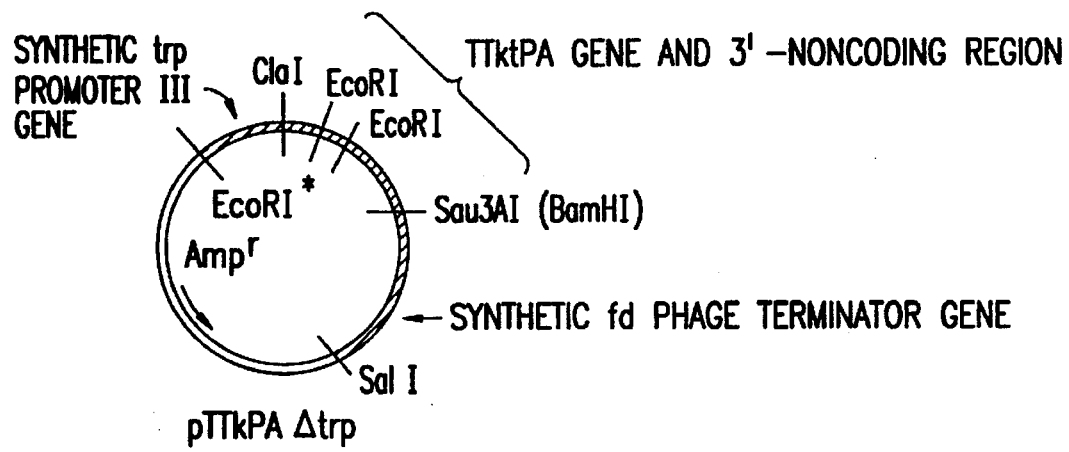
FIG.7

```
                        (EcoRI)
Coding chain:    5'- AATTCCATGATCCTGATAGGCAAGGTTTACACAGCA
Amino acid sequence:  AsnSerMetIleLeuIleGlyLysValTyrThrAla CAGAACCCCAGTGCCCAGGCACTGGGCCTGGGCAAACATAATTACTGCCGGAATCCTGAT
GlnAsnProSerAlaGlnAlaLeuGlyLeuGlyLysHisAsnTyrCysArgAsnProAsp GGGGATGCCAAGCCCTGGTGCCACGTGCTGAAGAACCGCAGGCTGACGTGGGAGTACTGT
GlyAspAlaLysProTrpCysHisValLeuLysAsnArgArgLeuThrTrpGluTyrCys GATGTGCCCTCCTGCTCCACCTGCGGCCTGAGACAGTACAGCCAGCCTCAGTTTCGCATC
AspValProSerCysSerThrCysGlyLeuArgGlnTyrSerGlnProGlnPheArgIle AAAGGAGGGCTCTTCGCCGACATCGCCTCCCACCCCTGGCAGGCTGCCATCTTTGCCAAG
LysGlyGlyLeuPheAlaAspIleAlaSerHisProTrpGlnAlaAlaIlePheAlaLys CACAGGAGGTCGCCCGGAGAGCGGTTCCTGTGCGGGGGCATACTCATCAGCTCCTGCTGG
HisArgArgSerProGlyGluArgPheLeuCysGlyGlyIleLeuIleSerSerCysTrp ATTCTCTCTGCCGCCCACTGCTTCCAGGAGAGGTTTCCGCCCCACCACCTGACGGTGATC
IleLeuSerAlaAlaHisCysPheGlnGluArgPheProProHisHisLeuThrValIle TTGGGCAGAACATACCGGGTGGTCCCTGGCGAGGAGGAGCAGAAATTTGAAGTCGAAAAA
LeuGlyArgThrTyrArgValValProGlyGluGluGluGlnLysPheGluValGluLys
                    (EcoRI)
TACATTGTCCATAAGG -3'
TyrIleValHisLys
```

FIG. 8

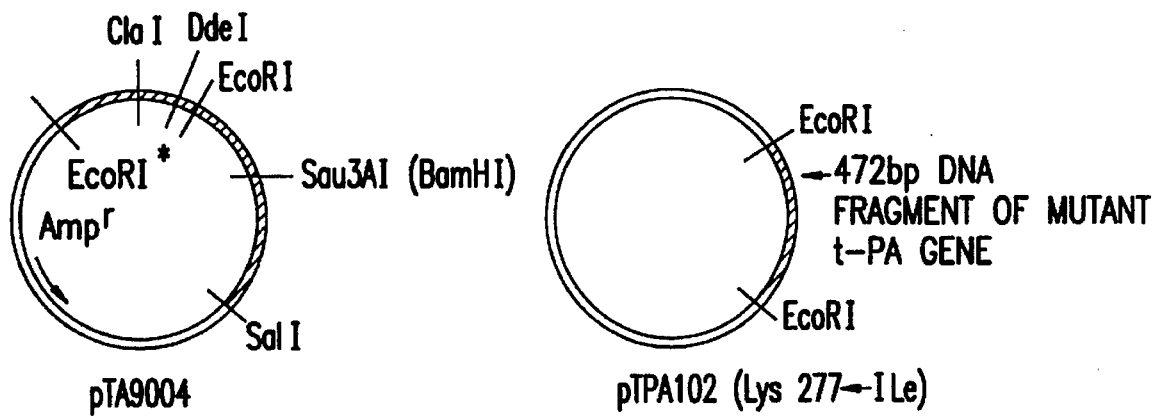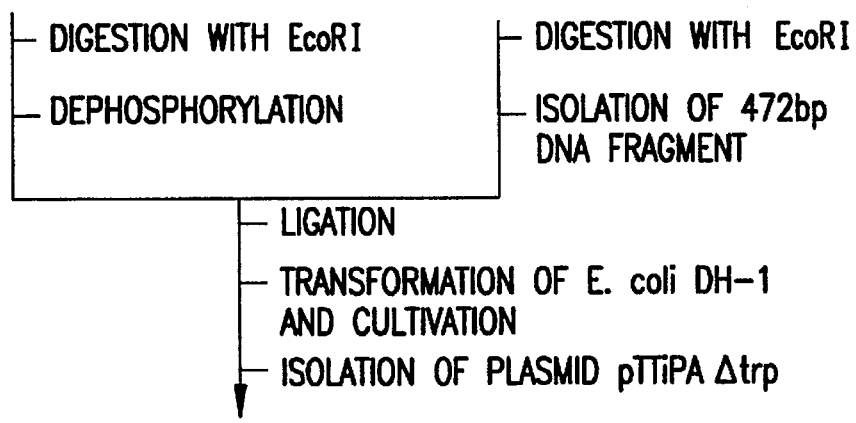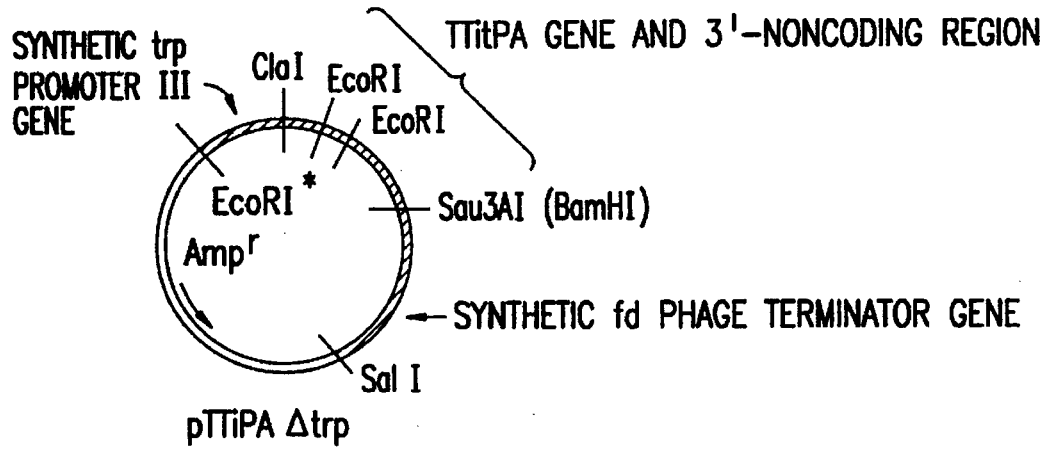
FIG.9

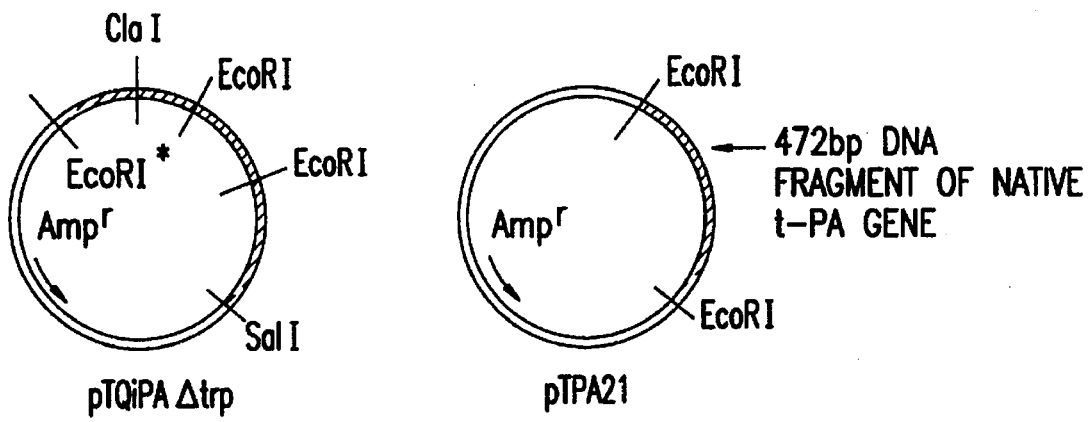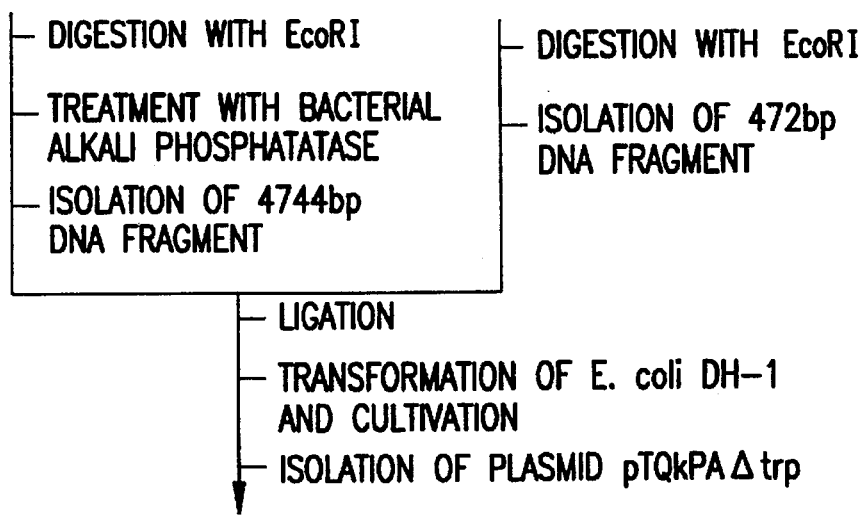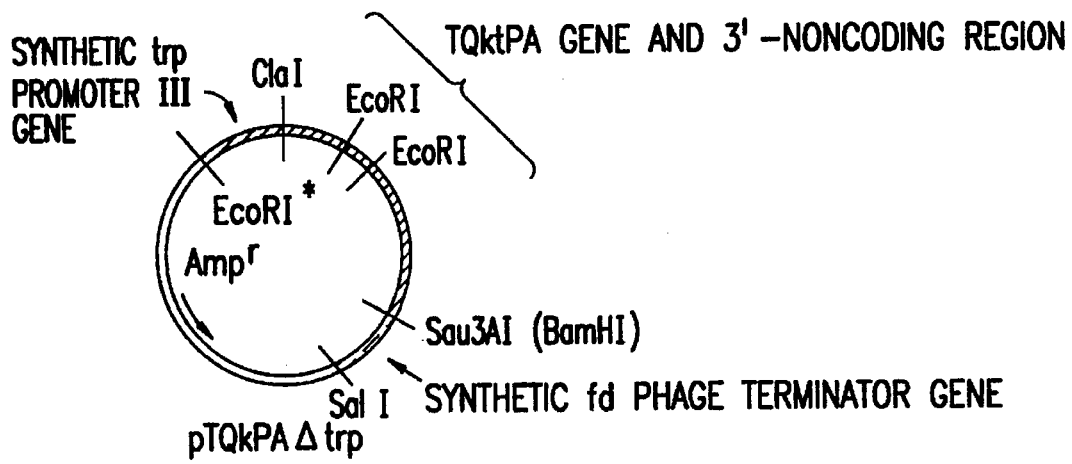
FIG.10

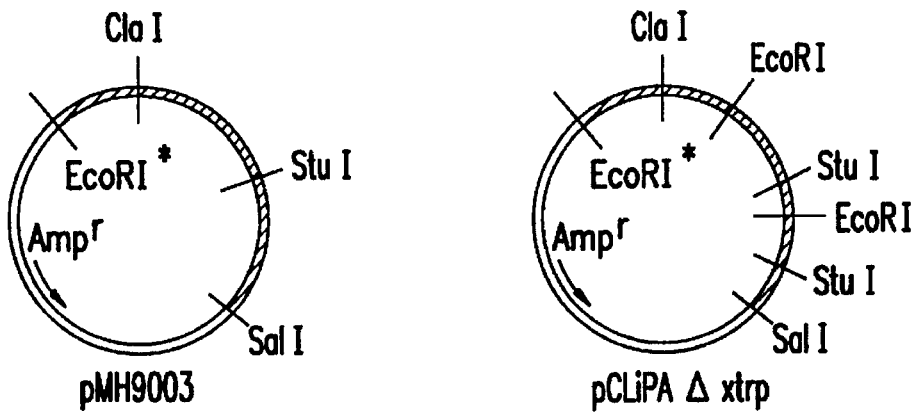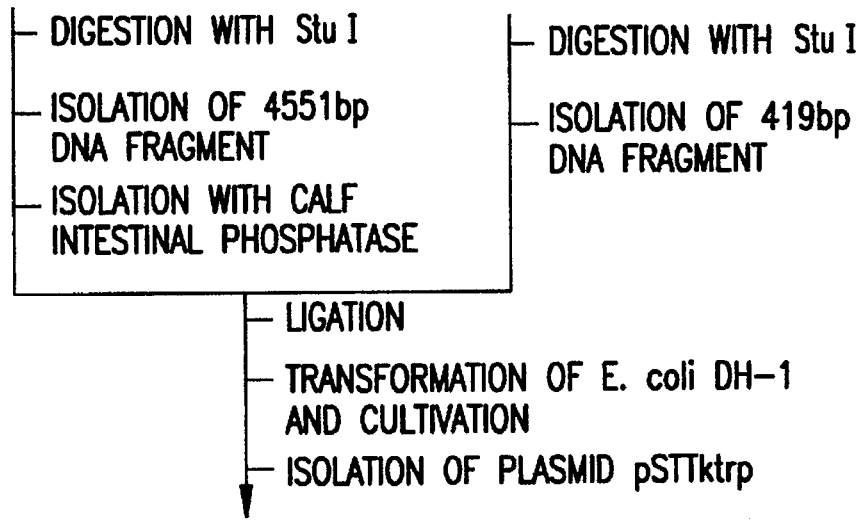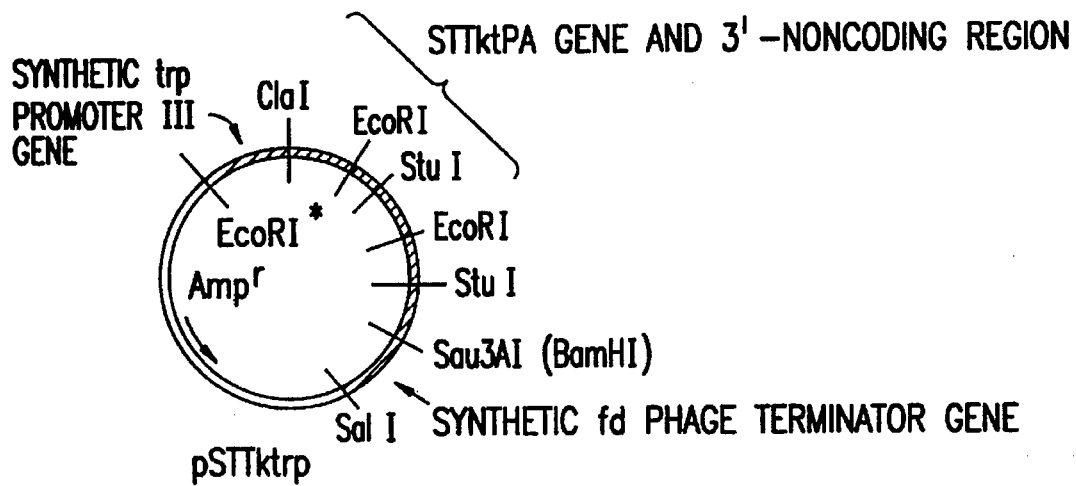
FIG.12

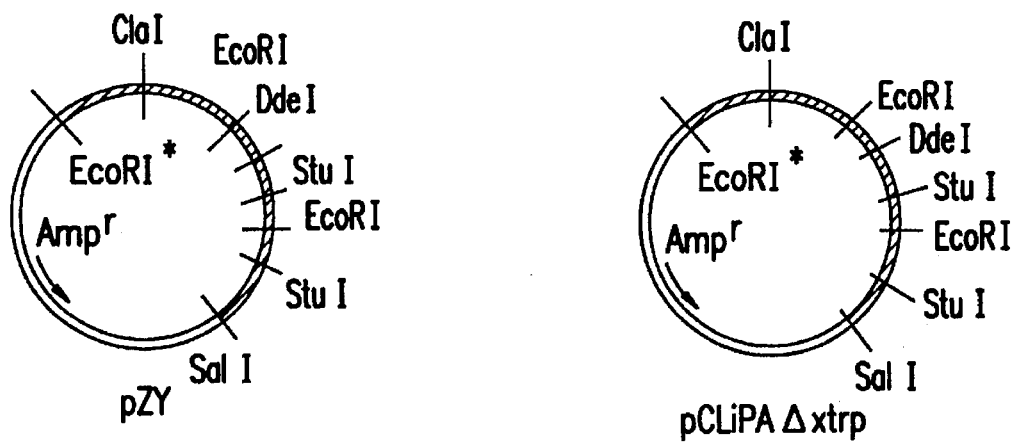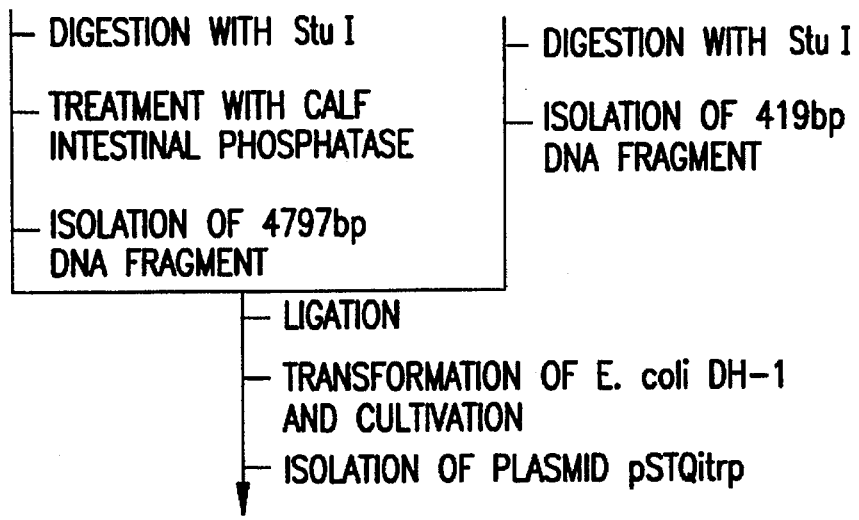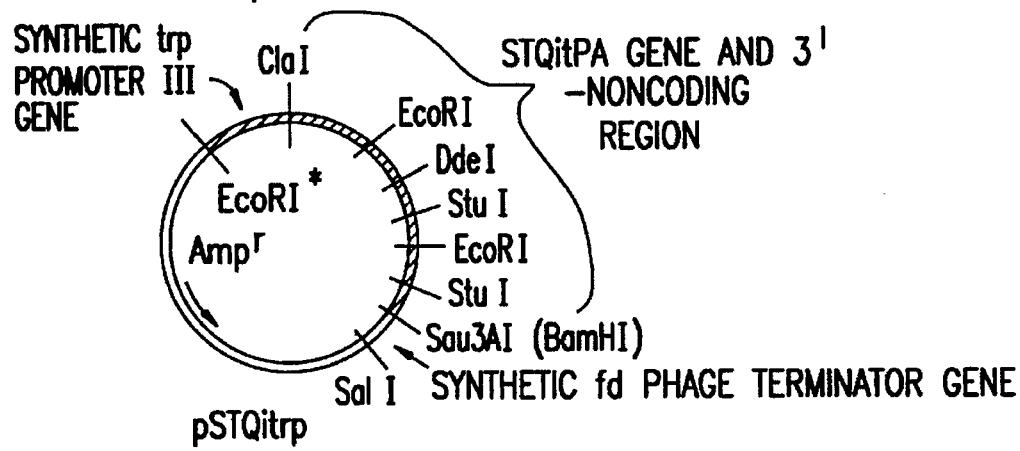
FIG. 14

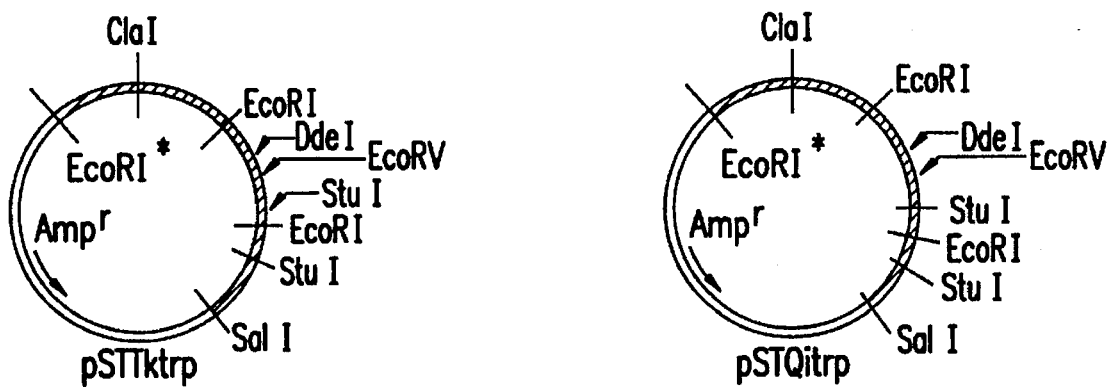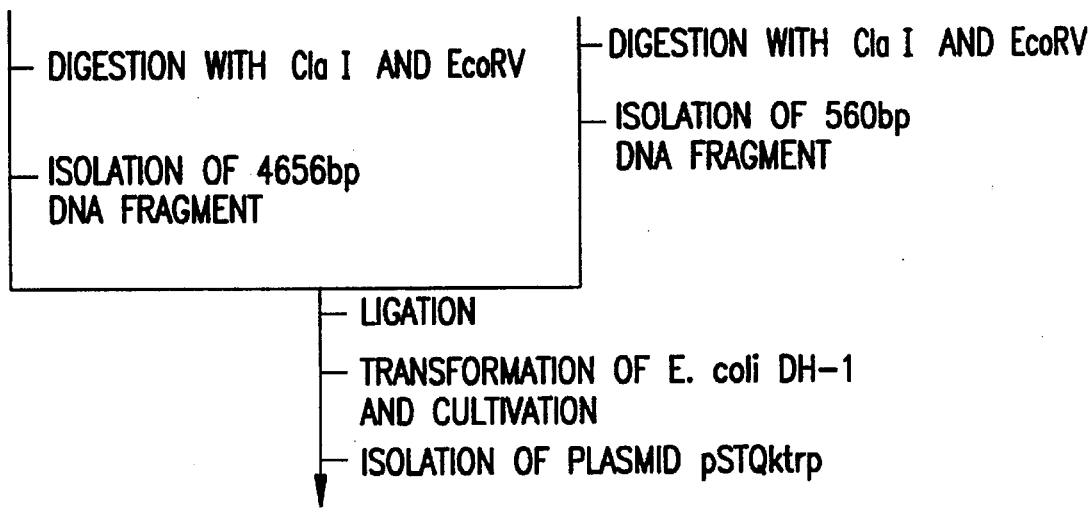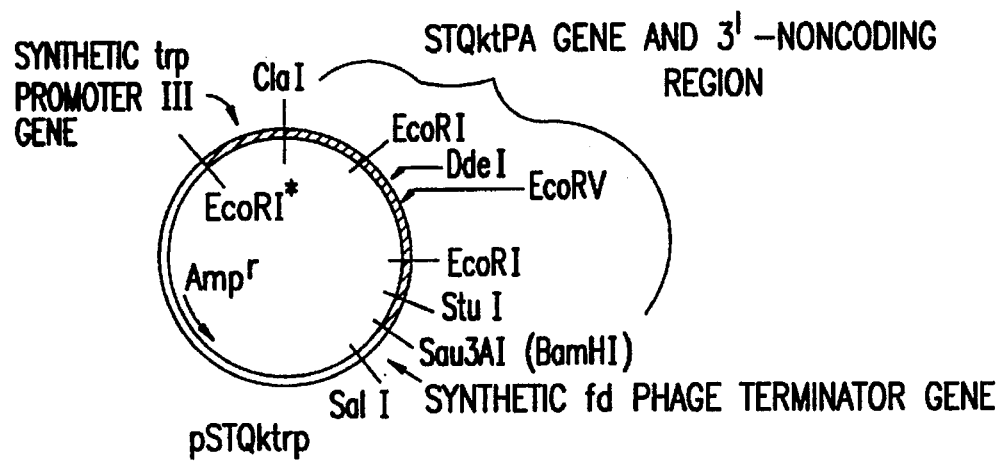
FIG.15

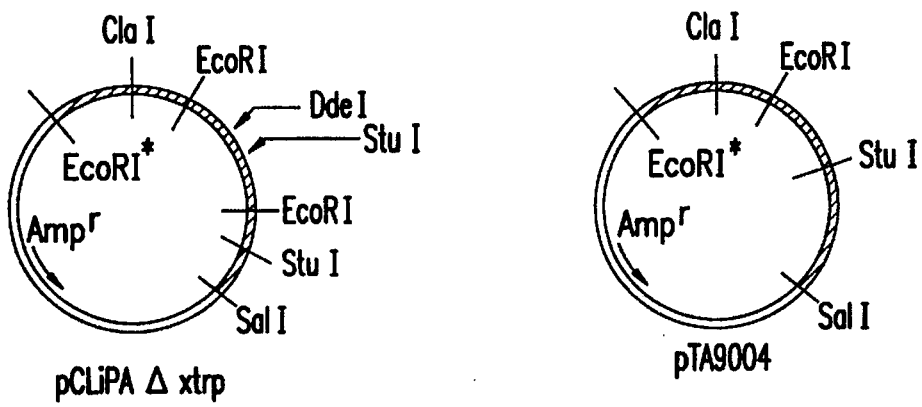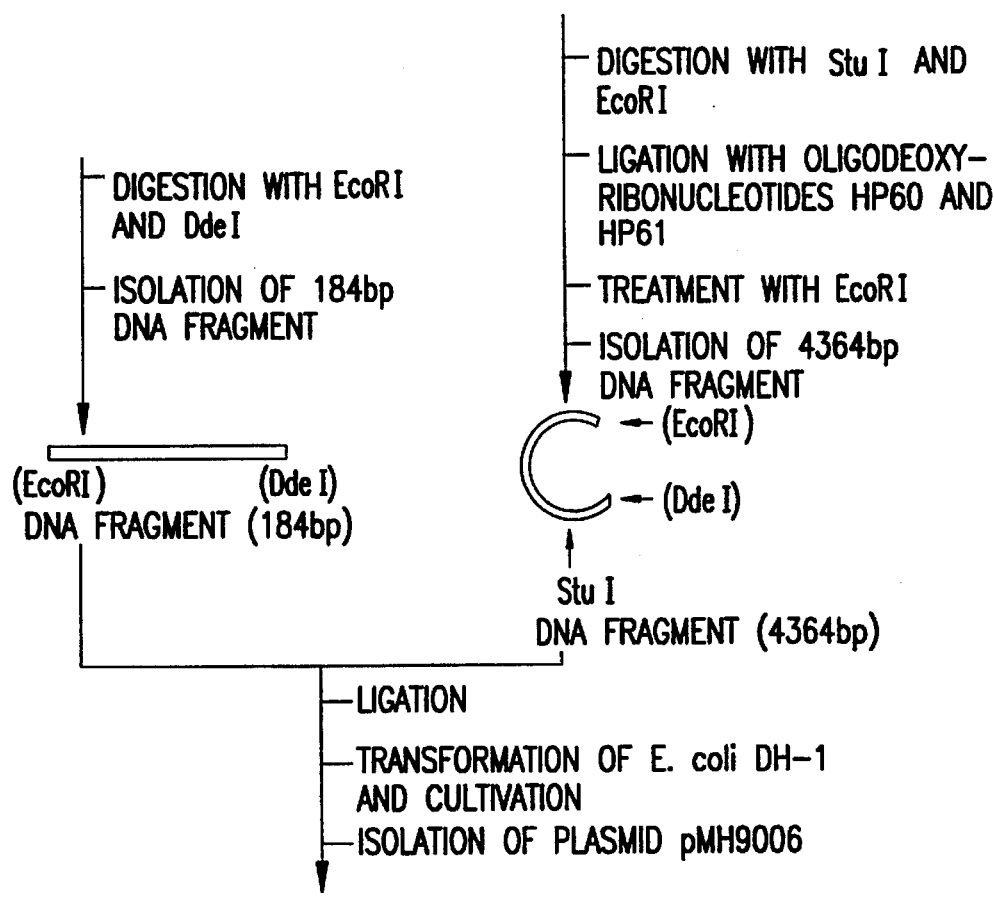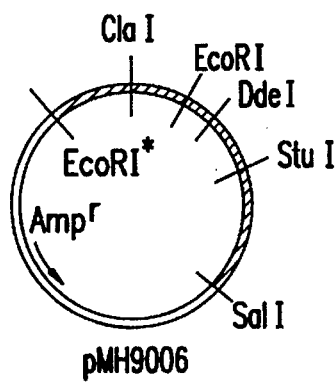
FIG.16

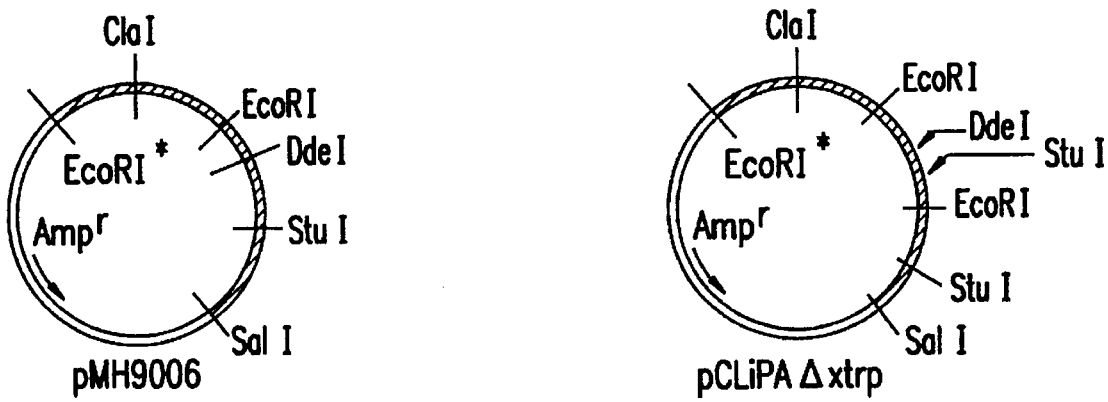
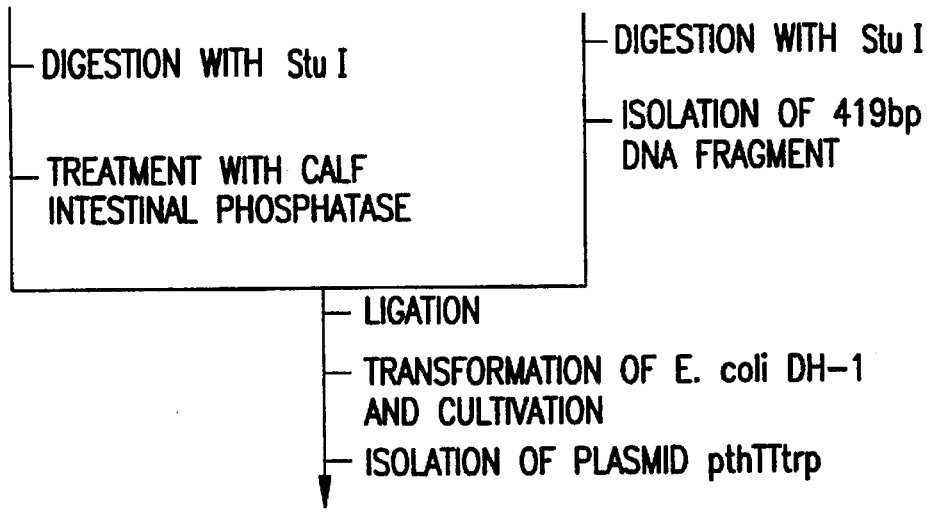
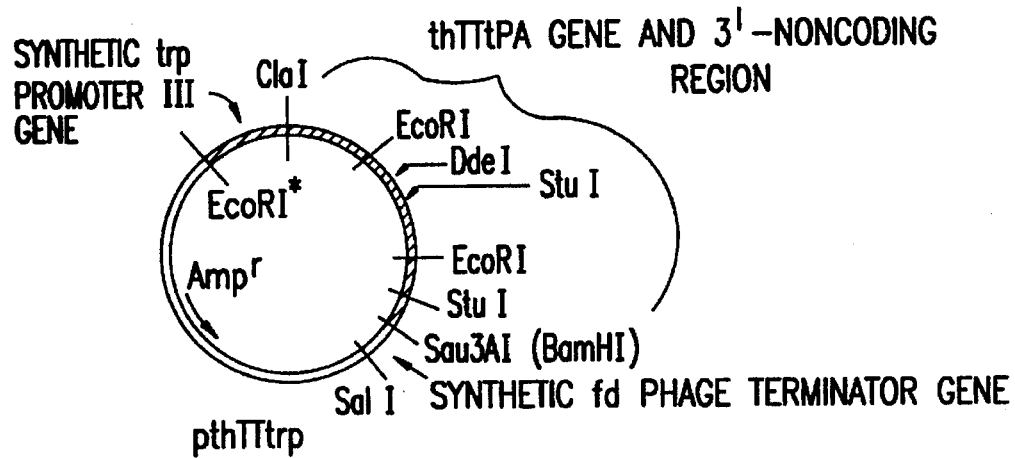
FIG.17

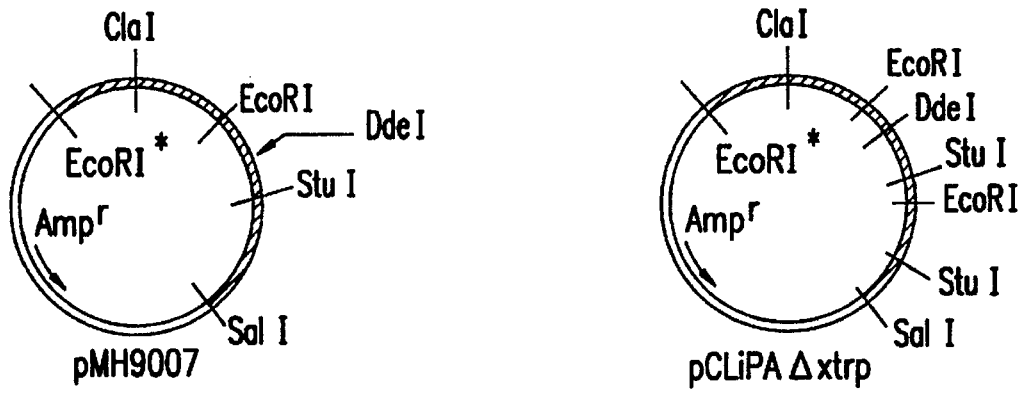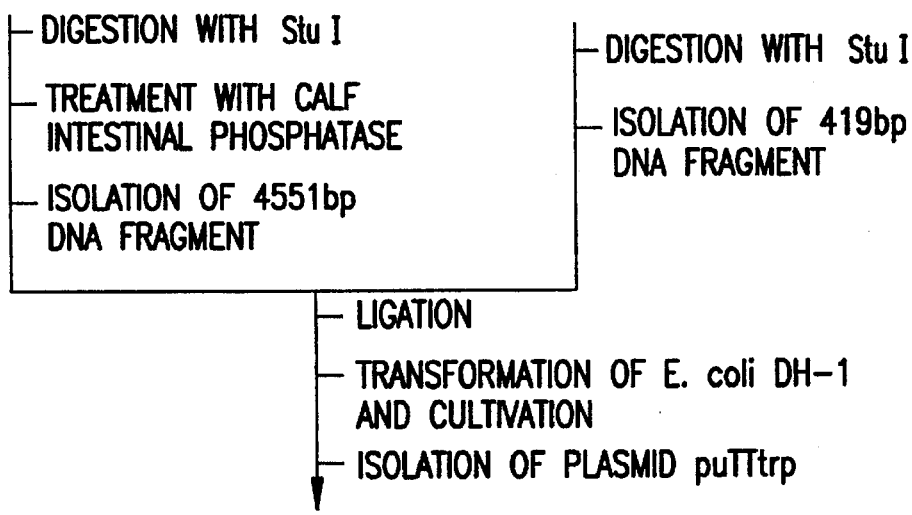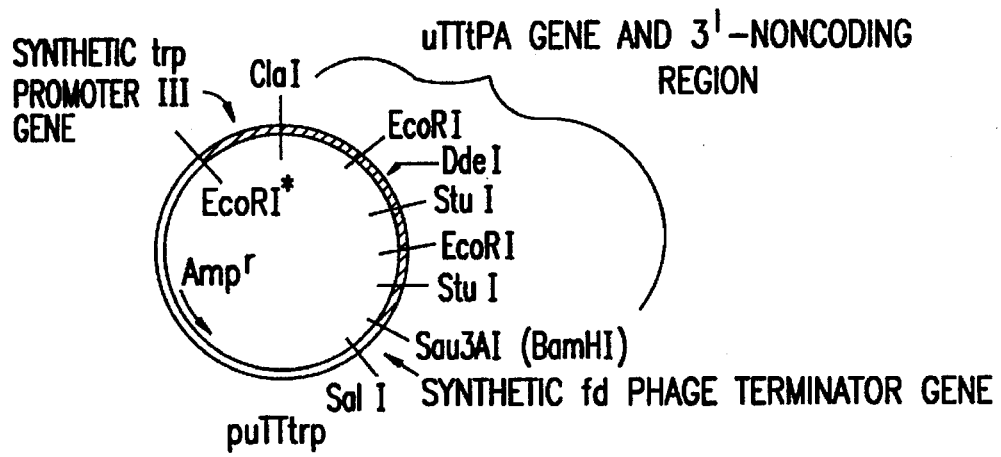
FIG.19

```
         10        20        30        40        50        60
5'- GTTAAGGGACGCTGTGAAGCAATCATGGATGCAATGAAGAGAGGGCTCTGCTGTGTGCTG
                              MetAspAlaMetLysArgGlyLeuCysCysValLeu 70        80        90       100       110       120
    CTGCTGTGTGGAGCAGTCTTCGTTTCGCCCAGCCAGGAAATCCATGCCCGATTCAGAAGA
    LeuLeuCysGlyAlaValPheValSerProSerGlnGluIleHisAlaArgPheArgArg 130       140       150       160       170       180
    GGAGCCAGATCTTACCAAGTGATCTGCAGAGATGAAAAAACGCAGATGATATACCAGCAA
    GlyAlaArgSerTyrGlnValIleCysArgAspGluLysThrGlnMetIleTyrGlnGln
         |→native tPA 190       200       210       220       230       240
    CATCAGTCATGGCTGCGCCCTGTGCTCAGAAGCAACCGGGTGGAATATTGCTGGTGCAAC
    HisGlnSerTrpLeuArgProValLeuArgSerAsnArgValGluTyrCysTrpCysAsn 250       260       270       280       290       300
    AGTGGCAGGGCACAGTGCCACTCAGTGCCTGTCAAAAGTTGCAGCGAGCCAAGGTGTTTC
    SerGlyArgAlaGlnCysHisSerValProValLysSerCysSerGluProArgCysPhe 310       320       330       340       350       360
    AACGGGGGCACCTGCCAGCAGGCCCTGTACTTCTCAGATTTCGTGTGCCAGTGCCCCGAA
    AsnGlyGlyThrCysGlnGlnAlaLeuTyrPheSerAspPheValCysGlnCysProGlu 370       380       390       400       410       420
    GGATTTGCTGGGAAGTGCTGTGAAATAGATACCAGGGCCACGTGCTACGAGGACCAGGGC
    GlyPheAlaGLyLysCysCysGluIleAspThrArgAlaThrCysTyrGluAspGlnGly 430       440       450       460       470       480
    ATCAGCTACAGGGGCACGTGGAGCACAGCGGAGAGTGGCGCCGAGTGCACCAACTGGAAC
    IleSerTyrArgGlyThrTrpSerThrAlaGluSerGlyAlaGluCysThrAsnTrpAsn 490       500       510       520       530       540
    AGCAGCGCGTTGGCCCAGAAGCCCTACAGCGGGCGGAGGCCAGACGCCATCAGGCTGGGC
    SerSerAlaLeuAlaGlnLysProTyrSerGlyArgArgProAspAlaIleArgLeuGly 550       560       570       580       590       600
    CTGGGGAACCACAACTACTGCAGAAACCCAGATCGAGACTCAAAGCCCTGGTGCTACGTC
    LeuGlyAsnHisAsnTyrCysArgAsnProAspArgAspSerLysProTrpCysTyrVal
```

FIG.21A

```
     610       620       630       640       650       660
TTTAAGGCGGGGAAGTACAGCTCAGAGTTCTGCAGCACCCCTGCCTGCTCTGAGGGAAAC
PheLysAlaGlyLysTyrSerSerGluPheCysSerThrProAlaCysSerGluGlyAsn 670       680       690       700       710       720
AGTGACTGCTACTTTGGGAATGGGTCAGCCTACCGTGGCACGCACAGCCTCACCGAGTCG
SerAspCysTyrPheGlyAsnGlySerAlaTyrArgGlyThrHisSerLeuThrGluSer 730       740       750       760       770       780
GGTGCCTCCTGCCTCCCGTGGAATTCCATGATCCTGATAGGCAAGGTTTACACAGCACAG
GlyAlaSerCysLeuProTrpAsnSerMetIleLeuIleGlyLysValTyrThrAlaGln 790       800       810       820       830       840
AACCCCAGTGCCCAGGCACTGGGCCTGGGCAAACATAATTACTGCCGGAATCCTGATGGG
AsnProSerAlaGlnAlaLeuGlyLeuGlyLysHisAsnTyrCysArgAsnProAspGly 850       860       870       880       890       900
GATGCCAAGCCCTGGTGCCACGTGCTGAAGAACCGCAGGCTGACGTGGGAGTACTGTGAT
AspAlaLysProTrpCysHisValLeuLysAsnArgArgLeuThrTrpGluTyrCysAsp 910       920       930       940       950       960
GTGCCCTCCTGCTCCACCTGCGGCCTGAGACAGTACAGCCAGCCTCAGTTTCGCATCAAA
ValProSerCysSerThrCysGlyLeuArgGlnTyrSerGlnProGlnPheArgIleLys 970       980       990      1000      1010      1020
GGAGGGCTCTTCGCCGACATCGCCTCCCACCCCTGGCAGGCTGCCATCTTTGCCAAGCAC
GlyGlyLeuPheAlaAspIleAlaSerHisProTrpGlnAlaAlaIlePheAlaLysHis 1030      1040      1050      1060      1070      1080
AGGAGGTCGCCCGGAGAGCGGTTCCTGTGCGGGGGCATACTCATCAGCTCCTGCTGGATT
ArgArgSerProGlyGluArgPheLeuCysGlyGlyIleLeuIleSerSerCysTrpIle 1090      1100      1110      1120      1130      1140
CTCTCTGCCGCCCACTGCTTCCAGGAGAGGTTTCCGCCCCACCACCTGACGGTGATCTTG
LeuSerAlaAlaHisCysPheGlnGluArgPheProProHisHisLeuThrValIleLeu 1150      1160      1170      1180      1190      1200
GGCAGAACATACCGGGTGGTCCCTGGCGAGGAGGAGCAGAAATTTGAAGTCGAAAAATAC
GlyArgThrTyrArgValValProGlyGluGluGluGlnLysPheGluValGluLysTyr 1210      1220      1230      1240      1250      1260
ATTGTCCATAAGGAATTCGATGATGACACTTACGACAATGACATTGCGCTGCTGCAGCTG
IleValHisLysGluPheAspAspAspThrTyrAspAsnAspIleAlaLeuLeuGlnLeu
```

FIG.21B

```
     1270      1280      1290      1300      1310      1320
AAATCGGATTCGTCCCGCTGTGCCCAGGAGAGCAGCGTGGTCCGCACTGTGTGCCTTCCC
LysSerAspSerSerArgCysAlaGlnGluSerSerValValArgThrValCysLeuPro 1330      1340      1350      1360      1370      1380
CCGGCGGACCTGCAGCTGCCGGACTGGACGGAGTGTGAGCTCTCCGGCTACGGCAAGCAT
ProAlaAspLeuGlnLeuProAspTrpThrGluCysGluLeuSerGlyTyrGlyLysHis 1390      1400      1410      1420      1430      1440
GAGGCCTTGTCTCCTTTCTATTCGGAGCGGCTGAAGGAGGCTCATGTCAGACTGTACCCA
GluAlaLeuSerProPheTyrSerGluArgLeuLysGluAlaHisValArgLeuTyrPro 1450      1460      1470      1480      1490      1500
TCCAGCCGCTGCACATCACAACATTTACTTAACAGAACAGTCACCGACAACATGCTGTGT
SerSerArgCysThrSerGlnHisLeuLeuAsnArgThrValThrAspAsnMetLueCys 1510      1520      1530      1540      1550      1560
GCTGGAGACACTCGGAGCGGCGGGCCCCAGGCAAACTTGCACGACGCCTGCCAGGGCGAT
AlaGlyAspThrArgSerGlyGlyProGlnAlaAsnLeuHisAspAlaCysGlnGlyAsp 1570      1580      1590      1600      1610      1620
TCGGGAGGCCCCCTGGTGTGTCTGAACGATGGCCGCATGACTTTGGTGGGCATCATCAGC
SerGlyGlyProLeuValCysLeuAsnAspGlyArgMetThrLeuValGlyIleIleSer 1630      1640      1650      1660      1670      1680
TGGGGCCTGGGCTGTGGACAGAAGGATGTCCCGGGTGTGTACACAAAGGTTACCAACTAC
TrpGlyLeuGlyCysGlyGlnLysAspValProGlyValTyrThrLysValThrAsnTyr 1690      1700      1710      1720      1730      1740
CTAGACTGGATTCGTGACAACATGCGACCGTGACCAGGAACACCCGACTCCTCAAAAGCA
LeuAspTrpIleArgAspAsnMetArgPro***
                               ⊢|
     1750      1760      1770      1780      1790      1800
AATGAGATCCCGCCTCTTCTTCTTCAGAAGACACTGCAAAGGCGCAGTGCTTCTCTACAG 1810      1820      1830      1840      1850      1860
ACTTCTCCAGACCCACCACACCGCAGAAGCGGGACGAGACCCTACAGGAGAGGGAAGAGT 1870      1880      1890      1900      1910      1920
GCATTTTCCCAGATACTTCCCATTTTGGAAGTTTTCAGGACTTGGTCTGATTTCAGGATA 1930      1940      1950      1960      1970      1980
CTCTGTCAGATGGGAAGACATGAATGCACACTAGCCTCTCCAGGAATGCCTCCTCCCTGG
```

FIG. 21C

```
       1990      2000      2010      2020      2030      2040
GCAGAAGTGGCCATGCCACCCTGTTTTCGCTAAAGCCCAACCTCCTGACCTGTCACCGTG 2050      2060      2070      2080      2090      2100
AGCAGCTTTGGAAACAGGACCACAAAAATGAAAGCATGTCTCAATAGTAAAAGAAACAAG

```
                10        20        30        40        50        60
5' - ATGTCTGAGGGAAACAGTGACTGCTACTTTGGGAATGGGTCAGCCTACCGTGGCACGCAG
     MetSerGluGlyAsnSerAspCysTyrPheGlyAsnGlySerAlaTyrArgGlyThrHis
     |→ TTKtPA
                70        80        90       100       110       120
     AGCCTCACCGAGTCGGGTGCCTCCTGCCTCCCGTGGAATTCCATGATCCTGATAGGCAAG
     SerLeuThrGluSerGlyAlaSerCysLeuProTrpAsnSerMetIleLeuIleGlyLys 130       140       150       160       170       180
     GTTTACACAGCACAGAACCCCAGTGCCCAGGCACTGGGCCTGGGCAAACATAATTACTGC
     ValTyrThrAlaGlnAsnProSerAlaGlnAlaLeuGlyLeuGlyLysHisAsnTyrCys 190       200       210       220       230       240
     CGGAATCCTGATGGGGATGCCAAGCCCTGGTGCCACGTGCTGAAGAACCGCAGGCTGACG
     ArgAsnProAspGlyAspAlaLysProTrpCysHisValLeuLysAsnArgArgLeuThr 250       260       270       280       290       300
     TGGGAGTACTGTGATGTGCCCTCCTGCTCCACCTGCGGCCTGAGACAGTACAGCCAGCCT
     TrpGluTyrCysAspValProSerCysSerThrCysGlyLeuArgGlnTyrSerGlnPro 310       320       330       340       350       360
     CAGTTTCGCATCAAAGGAGGGCTCTTCGCCGACATCGCCTCCCACCCCTGGCAGGCTGCC
     GlnPheArgIleLysGlyGlyLeuPheAlaAspIleAlaSerHisProTrpGlnAlaAla 370       380       390       400       410       420
     ATCTTTGCCAAGCACAGGAGGTCGCCCGGAGAGCGGTTCCTGTGCGGGGGCATACTCATC
     IlePheAlaLysHisArgArgSerProGlyGluArgPheLeuCysGlyGlyIleLeuIle 430       440       450       460       470       480
     AGCTCCTGCTGGATTCTCTCTGCCGCCCACTGCTTCCAGGAGAGGTTTCCGCCCCACCAC
     SerSerCysTrpIleLeuSerAlaAlaHisCysPheGlnGluArgPheProProHisHis 490       500       510       520       530       540
     CTGACGGTGATCTTGGGCAGAACATACCGGGTGGTCCCTGGCGAGGAGGAGCAGAAATTT
     LeuThrValIleLeuGlyArgThrTyrArgValValProGlyGluGluGluGlnLysPhe 550       560       570       580       590       600
     GAAGTCGAAAAATACATTGTCCATAAGGAATTCGATGATGACACTTACGACAATGACATT
     GluValGluLysTyrIleValHisLysGluPheAspAspAspThrTyrAspAsnAspIle 610       620       630       640       650       660
     GCGCTGCTGCAGCTGAAATCGGATTCGTCCCGCTGTGCCCAGGAGAGCAGCGTGGTCCGC
     AlaLeuLeuGlnLeuLysSerAspSerSerArgCysAlaGlnGluSerSerValValArg
```

FIG.29A

```
           670       680       690       700       710       720
ACTGTGTGCCTTCCCCCGGCGGACCTGCAGCTGCCGGACTGGACGGAGTGTGAGCTCTCC
ThrValCysLeuProProAlaAspLeuGlnLeuProAspTrpThrGluCysGluLeuSer 730       740       750       760       770       780
GGCTACGGCAAGCATGAGGCCTTGTCTCCTTTCTATTCGGAGCGGCTGAAGGAGGCTCAT
GlyTyrGlyLysHisGluAlaLeuSerProPheTyrSerGluArgLeuLysGluAlaHis 790       800       810       820       830       840
GTCAGACTGTACCCATCCAGCCGCTGCACATCACAACATTTACTTAACAGAACAGTCACC
ValArgLeuTyrProSerSerArgCysThrSerGlnHisLeuLeuAsnArgThrValThr 850       860       870       880       890       900
GACAACATGCTGTGTGCTGGAGACACTCGGAGCGGCGGGCCCCAGGCAAACTTGCACGAC
AspAsnMetLeuCysAlaGlyAspThrArgSerGlyGlyProGlnAlaAsnLeuHisAsp 910       920       930       940       950       960
GCCTGCCAGGGCGATTCGGGAGGCCCCCTGGTGTGTCTGAACGATGGCCGCATGACTTTG
AlaCysGlnGlyAspSerGlyGlyProLeuValCysLeuAsnAspGlyArgMetThrLeu 970       980       990      1000      1010      1020
GTGGGCATCATCAGCTGGGGCCTGGGCTGTGGACAGAAGGATGTCCCGGGTGTGTACACA
ValGlyIleIleSerTrpGlyLeuGlyCysGlyGlnLysAspValProGlyValTyrThr 1030      1040      1050      1060      1070      1080
AAGGTTACCAACTACCTAGACTGGATTCGTGACAACATGCGACCGTGA - 3'
LysValThrAsnTyrLeuAspTrpIleArgAspAsnMetArgPro***
                                              ←|
```

FIG.29B

```
              10        20        30        40        50        60
5' - ATGTCTGAGGGAAACAGTGACTGCTACTTTGGGAATGGGTCAGCCTACCGTGGCACGCAG
     MetSerGluGlyAsnSerAspCysTyrPheGlyAsnGlySerAlaTyrArgGlyThrHis
     |→   TTitPA
              70        80        90       100       110       120
     AGCCTCACCGAGTCGGGTGCCTCCTGCCTCCCGTGGAATTCCATGATCCTGATAGGCAAG
     SerLeuThrGluSerGlyAlaSerCysLeuProTrpAsnSerMetIleLeuIleGlyLys 130       140       150       160       170       180
     GTTTACACAGCACAGAACCCCAGTGCCCAGGCACTGGGCCTGGGCAAACATAATTACTGC
     ValTyrThrAlaGlnAsnProSerAlaGlnAlaLeuGlyLeuGlyLysHisAsnTyrCys 190       200       210       220       230       240
     CGGAATCCTGATGGGGATGCCAAGCCCTGGTGCCACGTGCTGAAGAACCGCAGGCTGACG
     ArgAsnProAspGlyAspAlaLysProTrpCysHisValLeuLysAsnArgArgLeuThr 250       260       270       280       290       300
     TGGGAGTACTGTGATGTGCCCTCCTGCTCCACCTGCGGCCTGAGACAGTACAGCCAGCCT
     TrpGluTyrCysAspValProSerCysSerThrCysGlyLeuArgGlnTyrSerGlnPro 310       320       330       340       350       360
     CAGTTTCGCATCAAAGGAGGGCTCTTCGCCGACATCGCCTCCCACCCCTGGCAGGCTGCC
     GlnPheArgIleLysGlyGlyLeuPheAlaAspIleAlaSerHisProTrpGlnAlaAla 370       380       390       400       410       420
     ATCTTTGCCAAGCACAGGAGGTCGCCCGGAGAGCGGTTCCTGTGCGGGGGCATACTCATC
     IlePheAlaLysHisArgArgSerProGlyGluArgPheLeuCysGlyGlyIleLeuIle 430       440       450       460       470       480
     AGCTCCTGCTGGATTCTCTCTGCCGCCCACTGCTTCCAGGAGAGGTTTCCGCCCCACCAC
     SerSerCysTrpIleLeuSerAlaAlaHisCysPheGlnGluArgPheProProHisHis 490       500       510       520       530       540
     CTGACGGTGATCTTGGGCAGAACATACCGGGTGGTCCCTGGCGAGGAGGAGCAGAAATTT
     LeuThrValIleLeuGlyArgThrTyrArgValValProGlyGluGluGluGlnLysPhe 550       560       570       580       590       600
     GAAGTCGAAAAATACATTGTCCATAAGGAATTCGATGATGACACTTACGACAATGACATT
     GluValGluLysTyrIleValHisLysGluPheAspAspAspThrTyrAspAsnAspIle 610       620       630       640       650       660
     GCGCTGCTGCAGCTGAAATCGGATTCGTCCCGCTGTGCCCAGGAGAGCAGCGTGGTCCGC
     AlaLeuLeuGlnLeuLysSerAspSerSerArgCysAlaGlnGluSerSerValValArg
```

FIG.30A

```
        670       680       690       700       710       720
ACTGTGTGCCTTCCCCCGGCGGACCTGCAGCTGCCGGACTGGACGGAGTGTGAGCTCTCC
ThrValCysLeuProProAlaAspLeuGlnLeuProAspTrpThrGluCysGluLeuSer 730       740       750       760       770       780
GGCTACGGCAAGCATGAGGCCTTGTCTCCTTTCTATTCGGAGCGGCTGAAGGAGGCTCAT
GlyTyrGlyLysHisGluAlaLeuSerProPheTyrSerGluArgLeuLysGluAlaHis 790       800       810       820       830       840
GTCAGACTGTACCCATCCAGCCGCTGCACATCACAACATTTACTTAACAGAACAGTCACC
ValArgLeuTyrProSerSerArgCysThrSerGlnHisLeuLeuAsnArgThrValThr 850       860       870       880       890       900
GACAACATGCTGTGTGCTGGAGACACTCGGAGCGGCGGGCCCCAGGCAAACTTGCACGAC
AspAsnMetLeuCysAlaGlyAspThrArgSerGlyGlyProGlnAlaAsnLeuHisAsp 910       920       930       940       950       960
GCCTGCCAGGGCGATTCGGGAGGCCCCCTGGTGTGTCTGAACGATGGCCGCATGACTTTG
AlaCysGlnGlyAspSerGlyGlyProLeuValCysLeuAsnAspGlyArgMetThrLeu 970       980       990      1000      1010      1020
GTGGGCATCATCAGCTGGGGCCTGGGCTGTGGACAGAAGGATGTCCCGGGTGTGTACACA
ValGlyIleIleSerTrpGlyLeuGlyCysGlyGlnLysAspValProGlyValTyrThr 1030      1040      1050      1060      1070      1080
AAGGTTACCAACTACCTAGACTGGATTCGTGACAACATGCGACCGTGA - 3'
LysValThrAsnTyrLeuAspTrpIleArgAspAsnMetArgPro***
                                               ←|
```

FIG.30B

```
                 10         20         30         40         50         60
5' - ATGTGTTATGAGGACCAGGGCATCAGCTACAGGGGCACGTGGAGCACAGCGGAGAGTGGC
     MetCysTyrGluAspGlnGlyIleSerTyrArgGlyThrTrpSerThrAlaGluSerGly
      |→ TQKtPA
                 70         80         90        100        110        120
     GCCGAGTGCACCAACTGGAACAGCAGCGCGTTGGCCCAGAAGCCCTACAGCGGGCGGAGG
     AlaGluCysThrAsnTrpAsnSerSerAlaLeuAlaGlnLysProTyrSerGlyArgArg 130        140        150        160        170        180
     CCAGACGCCATCAGGCTGGGCCTGGGGAACCACAACTACTGCAGAAACCCAGATCGAGAC
     ProAspAlaIleArgLeuGlyLeuGlyAsnHisAsnTyrCysArgAsnProAspArgAsp 190        200        210        220        230        240
     TCAAAGCCCTGGTGCTACGTCTTTAAGGCGGGGAAGTACAGCTCAGAGTTCTGCAGCACC
     SerLysProTrpCysTyrValPheLysAlaGlyLysTyrSerSerGluPheCysSerThr 250        260        270        280        290        300
     CCTGCCTGCTCTGAGGGAAACAGTGACTGCTACTTTGGGAATGGGTCAGCCTACCGTGGC
     ProAlaCysSerGluGlyAsnSerAspCysTyrPheGlyAsnGlySerAlaTyrArgGly 310        320        330        340        350        360
     ACGCACAGCCTCACCGAGTCGGGTGCCTCCTGCCTCCCGTGGAATTCCATGATCCTGATA
     ThrHisSerLeuThrGluSerGlyAlaSerCysLeuProTrpAsnSerMetIleLeuIle 370        380        390        400        410        420
     GGCAAGGTTTACACAGCACAGAACCCCAGTGCCCAGGCACTGGGCCTGGGCAAACATAAT
     GlyLysValTyrThrAlaGlnAsnProSerAlaGlnAlaLeuGlyLeuGlyLysHisAsn 430        440        450        460        470        480
     TACTGCCGGAATCCTGATGGGGATGCCAAGCCCTGGTGCCACGTGCTGAAGAACCGCAGG
     TyrCysArgAsnProAspGlyAspAlaLysProTrpCysHisValLeuLysAsnArgArg 490        500        510        520        530        540
     CTGACGTGGGAGTACTGTGATGTGCCCTCCTGCTCCACCTGCGGCCTGAGACAGTACAGC
     LeuThrTrpGluTyrCysAspValProSerCysSerThrCysGlyLeuArgGlnTyrSer 550        560        570        580        590        600
     CAGCCTCAGTTTCGCATCAAAGGAGGGCTCTTCGCCGACATCGCCTCCCACCCCTGGCAG
     GlnProGlnPheArgIleLysGlyGlyLeuPheAlaAspIleAlaSerHisProTrpGln 610        620        630        640        650        660
     GCTGCCATCTTTGCCAAGCACAGGAGGTCGCCCGGAGAGCGGTTCCTGTGCGGGGGCATA
     AlaAlaIlePheAlaLysHisArgArgSerProGlyGluArgPheLeuCysGlyGlyIle
```

FIG.31A

```
     670       680       690       700       710       720
CTCATCAGCTCCTGCTGGATTCTCTCTGCCGCCCACTGCTTCCAGGAGAGGTTTCCGCCC
LeuIleSerSerCysTrpIleLeuSerAlaAlaHisCysPheGlnGluArgPheProPro 730       740       750       760       770       780
CACCACCTGACGGTGATCTTGGGCAGAACATACCGGGTGGTCCCTGGCGAGGAGGAGCAG
HisHisLeuThrValIleLeuGlyArgThrTyrArgValValProGlyGluGluGluGln 790       800       810       820       830       840
AAATTTGAAGTCGAAAAATACATTGTCCATAAGGAATTCGATGATGACACTTACGACAAT
LysPheGluValGluLysTyrIleValHisLysGluPheAspAspAspThrTyrAspAsn 850       860       870       880       890       900
GACATTGCGCTGCTGCAGCTGAAATCGGATTCGTCCCGCTGTGCCCAGGAGAGCAGCGTG
AspIleAlaLeuLeuGlnLeuLysSerAspSerSerArgCysAlaGlnGluSerSerVal 910       920       930       940       950       960
GTCCGCACTGTGTGCCTTCCCCCGGCGGACCTGCAGCTGCCGGACTGGACGGAGTGTGAG
ValArgThrValCysLeuProProAlaAspLeuGlnLeuProAspTrpThrGluCysGlu 970       980       990      1000      1010      1020
CTCTCCGGCTACGGCAAGCATGAGGCCTTGTCTCCTTTCTATTCGGAGCGGCTGAAGGAG
LeuSerGlyTyrGlyLysHisGluAlaLeuSerProPheTyrSerGluArgLeuLysGlu 1030      1040      1050      1060      1070      1080
GCTCATGTCAGACTGTACCCATCCAGCCGCTGCACATCACAACATTTACTTAACAGAACA
AlaHisValArgLeuTyrProSerSerArgCysThrSerGlnHisLeuLeuAsnArgThr 1090      1100      1110      1120      1130      1140
GTCACCGACAACATGCTGTGTGCTGGAGACACTCGGAGCGGCGGGCCCCAGGCAAACTTG
ValThrAspAsnMetLeuCysAlaGlyAspThrArgSerGlyGlyProGlnAlaAsnLeu 1150      1160      1170      1180      1190      1200
CACGACGCCTGCCAGGGCGATTCGGGAGGCCCCCTGGTGTGTCTGAACGATGGCCGCATG
HisAspAlaCysGlnGlyAspSerGlyGlyProLeuValCysLeuAsnAspGlyArgMet 1210      1220      1230      1240      1250      1260
ACTTTGGTGGGCATCATCAGCTGGGGCCTGGGCTGTGGACAGAAGGATGTCCCGGGTGTG
ThrLeuValGlyIleIleSerTrpGluLeuGlyCysGlyGlnLysAspValProGlyVal 1270      1280      1290      1300      1310
TACACAAAGGTTACCAACTACCTAGACTGGATTCGTGACAACATGCGACCGTGA - 3'
TyrThrLysValThrAsnTyrLeuAspTrpIleArgAspAsnMetArgPro***
```

FIG.31B

```
            10        20        30        40        50        60
5' - ATGTGTTATGAGGACCAGGGGCATCAGCTACAGGGGCACGTGGAGCACAGCGGAGAGTGGC
     MetCysTyrGluAspGlnGlyIleSerTyrArgGlyThrTrpSerThrAlaGluSerGly
     |→ TQitPA
            70        80        90       100       110       120
     GCCGAGTGCACCAACTGGAACAGCAGCGCGTTGGCCCAGAAGCCCTACAGCGGGCGGAGG
     AlaGluCysThrAsnTrpAsnSerSerAlaLeuAlaGlnLysProTyrSerGlyArgArg 130       140       150       160       170       180
     CCAGACGCCATCAGGCTGGGCCTGGGGAACCACAACTACTGCAGAAACCCAGATCGAGAC
     ProAspAlaIleArgLeuGlyLeuGlyAsnHisAsnTyrCysArgAsnProAspArgAsp 190       200       210       220       230       240
     TCAAAGCCCTGGTGCTACGTCTTTAAGGCGGGGAAGTACAGCTCAGAGTTCTGCAGCACC
     SerLysProTrpCysTyrValPheLysAlaGlyLysTyrSerSerGluPheCysSerThr 250       260       270       280       290       300
     CCTGCCTGCTCTGAGGGAAACAGTGACTGCTACTTTGGGAATGGGTCAGCCTACCGTGGC
     ProAlaCysSerGluGlyAsnSerAspCysTyrPheGlyAsnGlySerAlaTyrArgGly 310       320       330       340       350       360
     ACGCACAGCCTCACCGAGTCGGGTGCCTCCTGCCTCCCGTGGAATTCCATGATCCTGATA
     ThrHisSerLeuThrGluSerGlyAlaSerCysLeuProTrpAsnSerMetIleLeuIle 370       380       390       400       410       420
     GGCAAGGTTTACACAGCACAGAACCCCAGTGCCCAGGCACTGGGCCTGGGCAAACATAAT
     GlyLysValTyrThrAlaGlnAsnProSerAlaGlnAlaLeuGlyLeuGlyLysHisAsn 430       440       450       460       470       480
     TACTGCCGGAATCCTGATGGGGATGCCAAGCCCTGGTGCCACGTGCTGAAGAACCGCAGG
     TyrCysArgAsnProAspGlyAspAlaLysProTrpCysHisValLeuLysAsnArgArg 490       500       510       520       530       540
     CTGACGTGGGAGTACTGTGATGTGCCCTCCTGCTCCACCTGCGGCCTGAGACAGTACAGC
     LeuThrTrpGluTyrCysAspValProSerCysSerThrCysGlyLeuArgGlnTyrSer 550       560       570       580       590       600
     CAGCCTCAGTTTCGCATCAAAGGAGGGCTCTTCGCCGACATCGCCTCCCACCCCTGGCAG
     GlnProGlnPheArgIleLysGlyGlyLeuPheAlaAspIleAlaSerHisProTrpGln 610       620       630       640       650       660
     GCTGCCATCTTTGCCAAGCACAGGAGGTCGCCCGGAGAGCGGTTCCTGTGCGGGGGCATA
     AlaAlaIlePheAlaLysHisArgArgSerProGlyGluArgPheLeuCysGlyGlyIle
```

FIG.32A

```
       670       680       690       700       710       720
CTCATCAGCTCCTGCTGGATTCTCTCTGCCGCCCACTGCTTCCAGGAGAGGTTTCCGCCC
LeuIleSerSerCysTrpIleLeuSerAlaAlaHisCysPheGlnGluArgPheProPro 730       740       750       760       770       780
CACCACCTGACGGTGATCTTGGGCAGAACATACCGGGTGGTCCCTGGCGAGGAGGAGCAG
HisHisLeuTHrValIleLeuGlyArgThrTyrArgValValProGlyGluGluGluGln 790       800       810       820       830       840
AAATTTGAAGTCGAAAAATACATTGTCCATAAGGAATTCGATGATGACACTTACGACAAT
LysPheGluValGluLysTyrIleValHisLysGluPheAspAspAspThrTyrAspAsn 850       860       870       880       890       900
GACATTGCGCTGCTGCAGCTGAAATCGGATTCGTCCCGCTGTGCCCAGGAGAGCAGCGTG
AspIleAlaLeuLeuGlnLueLysSerAspSerSerArgCysAlaGlnGluSerSerVal 910       920       930       940       950       960
GTCCGCACTGTGTGCCTTCCCCCGGCGGACCTGCAGCTGCCGGACTGGACGGAGTGTGAG
ValArgThrValCysLeuProProAlaAspLeuGlnLeuProAspTrpThrGluCysGlu 970       980       990      1000      1010      1020
CTCTCCGGCTACGGCAAGCATGAGGCCTTGTCTCCTTTCTATTCGGAGCGGCTGAAGGAG
LeuSerGlyTyrGlyLysHisGluAlaLeuSerProPheTyrSerGluArgLeuLysGlu 1030      1040      1050      1060      1070      1080
GCTCATGTCAGACTGTACCCATCCAGCCGCTGCACATCACAACATTTACTTAACAGAACA
AlaHisValArgLeuTyrProSerSerArgCysThrSerGlnHisLeuLeuAsnArgThr 1090      1100      1110      1120      1130      1140
GTCACCGACAACATGCTGTGTGCTGGAGACACTCGGAGCGGCGGGCCCCAGGCAAACTTG
ValThrAspAsnMetLeuCysAlaGlyAspThrArgSerGlyGlyProGlnAlaAsnLeu 1150      1160      1170      1180      1190      1200
CACGACGCCTGCCAGGGCGATTCGGGAGGCCCCCTGGTGTGTCTGAACGATGGCCGCATG
HisAspAlaCysGlnGlyAspSerGlyGlyProLeuValCysLeuAsnAspGlyArgMet 1210      1220      1230      1240      1250      1260
ACTTTGGTGGGCATCATCAGCTGGGGCCTGGGCTGTGGACAGAAGGATGTCCCGGGTGTG
ThrLeuValGlyIleIleSerTrpGluLeuGlyCysGlyGlnLysAspValProGlyVal 1270      1280      1290      1300      1310
TACACAAAGGTTACCAACTACCTAGACTGGATTCGTGACAACATGCGACCGTGA - 3'
TyrThrLysValThrAsnTyrLeuAspTrpIleArgAspAsnMetArgPro***
```

FIG.32B

```
                    10         20         30         40         50         60
5' - ATGTCTGAGGGAAACAGTGACTGCTACTTTGGGAATGGGTCAGCCTACCGTGGCACGCAC
     MetSerGluGlyAsnSerAspCysTyrPheGLyAsnGlySerAlaTyrArgGlyThrHis
     |→ STTktPA
                    70         80         90        100        110        120
     AGCCTCACCGAGTCGGGTGCCTCCTGCCTCCCGTGGAATTCCATGATCCTGATAGGCAAG
     SerLeuThrGluSerGlyAlaSerCysLeuProTrpAsnSerMetIleLeuIleGlyLys 130        140        150        160        170        180
     GTTTACACAGCACAGAACCCCAGTGCCCAGGCACTGGGCCTGGGCAAACATAATTACTGC
     ValTyrThrAlaGlnAsnProSerAlaGlnAlaLeuGlyLeuGlyLysHisAsnTyrCys 190        200        210        220        230        240
     CGGAATCCTGATGGGGATGCCAAGCCCTGGTGCCACGTGCTGAAGAACCGCAGGCTGACG
     ArgAsnProAspGlyAspAlaLysProTrpCysHisValLeiLysAsnArgArgLeuThr 250        260        270        280        290        300
     TGGGAGTACTGTGATGTGCCCTCCTGCTCCACCTGCGGCCTGAGACAGTACAGCCAGCCA
     TrpGluTyrCysAspValProSerCysSerThrCysGlyLeuArgGlnTyrSerGlnPro 310        320        330        340        350        360
     CAGTTTGATATCAAAGGAGGCCTCTTCGCCGACATCGCCTCCCACCCCTGGCAGGCTGCC
     GlnPheAspIleLysGlyGlyLeuPheAlaAspIleAlaSerHisProTrpGlnAlaAla 370        380        390        400        410        420
     ATCTTTGCCAAGCACAGGAGGTCGCCCGGAGAGCGGTTCCTGTGCGGGGGCATACTCATC
     IlePheAlaLysHisArgArgSerProGlyGluArgPheLeuCysGlyGlyIleLeuIle 430        440        450        460        470        480
     AGCTCCTGCTGGATTCTCTCTGCCGCCCACTGCTTCCAGGAGAGGTTTCCGCCCCACCAC
     SerSerCysTrpIleLeuSerAlaAlaHisCysPheGlnGluArgPheProProHisHis 490        500        510        520        530        540
     CTGACGGTGATCTTGGGCAGAACATACCGGGTGGTCCCTGGCGAGGAGGAGCAGAAATTT
     LeuThrValIleLeuGlyArgThrTyrArgValValProGlyGluGluGluGlnLysPhe 550        560        570        580        590        600
     GAAGTCGAAAAATACATTGTCCATAAGGAATTCGATGATGACACTTACGACAATGACATT
     GluValGluLysTyrIleValHisLysGluPheAspAspAspThrTyrAspAsnAspIle 610        620        630        640        650        660
     GCGCTGCTGCAGCTGAAATCGGATTCGTCCCGCTGTGCCCAGGAGAGCAGCGTGGTCCGC
     AlaLeuLeuGlnLeuLysSerAspSerSerArgCysAlaGlnGluSerSerValValArg
```

FIG.33A

```
      670       680       690       700       710       720
ACTGTGTGCCTTCCCCCGGCGGACCTGCAGCTGCCGGACTGGACGGAGTGTGAGCTCTCT
ThrValCysLeuProProAlaAspLeuGlnLeuProAspTrpThrGluCysGluLeuSer 730       740       750       760       770       780
GGCTACGGCAAGCATGAGGCCTTGTCTCCTTTCTATTCGGAGCGGCTGAAGGAGGCTCAT
GlyTyrGlyLysHisGluAlaLeuSerProPheTyrSerGluArgLeuLysGluAlaHis 790       800       810       820       830       840
GTCAGACTGTACCCATCCAGCCGCTGCACATCACAACATTTACTTAACAGAACAGTCACC
ValArgLeuTyrProSerSerArgCysThrSerGlnHisLeuLeuAsnArgThrValThr 850       860       870       880       890       900
GACAACATGCTGTGTGCTGGAGACACTCGGAGCGGCGGGCCCCAGGCAAACTTGCACGAC
AspAsnMetLeuCysAlaGlyAspThrArgSerGlyGlyProGlnAlaAsnLeuHisAsp 910       920       930       940       950       960
GCCTGCCAGGGCGATTCGGGAGGCCCCCTGGTGTGTCTGAACGATGGCCGCATGACTTTG
AlaCysGlnGlyAspSerGlyGlyProLeuValCysLeuAsnAspGlyArgMetThrLeu 970       980       990      1000      1010      1020
GTGGGCATCATCAGCTGGGGCCTGGGCTGTGGACAGAAGGATGTCCCGGGTGTGTACACA
ValGlyIleIleSerTrpGlyLeuGlyCysGlyGlnLysAspValProGlyValTyrThr 1030      1040      1050      1060      1070
AAGGTTACCAACTACCTAGACTGGATTCGTGACAACATGCGACCGTGA - 3'
LysValThrAsnTyrLeuAspTrpIleArgAspAsnMetArgPro***
                                               ←|
```

FIG.33B

```
         10        20        30        40        50        60
5' - ATGTGTTATGAGGACCAGGGCATCAGCTACAGGGGCACGTGGAGCACAGCGGAGAGTGGC
     MetCysTyrGluAspGlnGlyIleSerTyrArgGlyThrTrpSerThrAlaGluSerGly
      |→ STQKtPA
         70        80        90       100       110       120
     GCCGAGTGCACCAACTGGAACAGCAGCGCGTTGGCCCAGAAGCCCTACAGCGGGCGGAGG
     AlaGluCysThrAsnTrpAsnSerSerAlaLeuAlaGlnLysProTyrSerGlyArgArg 130       140       150       160       170       180
     CCAGACGCCATCAGGCTGGGCCTGGGGAACCACAACTACTGCAGAAACCCAGATCGAGAC
     ProAspAlaIleArgLeuGlyLeuGlyAsnHisAsnTyrCysArgAsnProAspArgAsp 190       200       210       220       230       240
     TCAAAGCCCTGGTGCTACGTCTTTAAGGCGGGGAAGTACAGCTCAGAGTTCTGCAGCACC
     SerLysProTrpCysTyrValPheLysAlaGlyLysTyrSerSerGluPheCysSerThr 250       260       270       280       290       300
     CCTGCCTGCTCTGAGGGAAACAGTGACTGCTACTTTGGGAATGGGTCAGCCTACCGTGGC
     ProAlaCysSerGluGlyAsnSerAspCysTyrPheGlyAsnGlySerAlaTyrArgGly 310       320       330       340       350       360
     ACGCACAGCCTCACCGAGTCGGGTGCCTCCTGCCTCCCGTGGAATTCCATGATCCTGATA
     ThrHisSerLeuThrGluSerGlyAlaSerCysLeuProTrpAsnSerMetIleLeuIle 370       380       390       400       410       420
     GGCAAGGTTTACACAGCACAGAACCCCAGTGCCCAGGCACTGGGCCTGGGCAAACATAAT
     GlyLysValTyrThrAlaGlnAsnProSerAlaGlnAlaLeuGlyLeuGlyLysHisAsn 430       440       450       460       470       480
     TACTGCCGGAATCCTGATGGGGATGCCAAGCCCTGGTGCCACGTGCTGAAGAACCGCAGG
     TyrCysArgAsnProAspGlyAspAlaLysProTrpCysHisValLeuLysAsnArgArg 490       500       510       520       530       540
     CTGACGTGGGAGTACTGTGATGTGCCCTCCTGCTCCACCTGCGGCCTGAGACAGTACAGC
     LeuThrTrpGluTyrCysAspValProSerCysSerThrCysGlyLeuArgGlnTyrSer 550       560       570       580       590       600
     CAGCCTCAGTTTCGCATCAAAGGAGGGCTCTTCGCCGACATCGCCTCCCACCCCTGGCAG
     GlnProGlnPheArgIleLysGlyGlyLeuPheAlaAspIleAlaSerHisProTrpGln 610       620       630       640       650       660
     GCTGCCATCTTTGCCAAGCACAGGAGGTCGCCCGGAGAGCGGTTCCTGTGCGGGGGCATA
     AlaAlaIlePheAlaLysHisArgArgSerProGlyGluArgPheLeuCysGlyGlyIle
```

FIG.34A

```
       670       680       690       700       710       720
CTCATCAGCTCCTGCTGGATTCTCTCTGCCGCCCACTGCTTCCAGGAGAGGTTTCCGCCC
LeuIleSerSerCysTrpIleLeuSerAlaAlaHisCysPheGlnGluArgPheProPro 730       740       750       760       770       780
CACCACCTGACGGTGATCTTGGGCAGAACATACCGGGTGGTCCCTGGCGAGGAGGAGCAG
HisHisLeuThrValIleLeuGlyArgThrTyrArgValValProGlyGluGluGluGln 790       800       810       820       830       840
AAATTTGAAGTCGAAAAATACATTGTCCATAAGGAATTCGATGATGACACTTACGACAAT
LysPheGluValGluLysTyrIleValHisLysGluPheAspAspAspThrTyrAspAsn 850       860       870       880       890       900
GACATTGCGCTGCTGCAGCTGAAATCGGATTCGTCCCGCTGTGCCCAGGAGAGCAGCGTG
AspIleAlaLeuLeuGlnLeuLysSerAspSerSerArgCysAlaGlnGluSerSerVal 910       920       930       940       950       960
GTCCGCACTGTGTGCCTTCCCCCGGCGGACCTGCAGCTGCCGGACTGGACGGAGTGTGAG
ValArgThrValCysLeuProProAlaAspLeuGlnLeuProAspTrpThrGluCysGlu 970       980       990      1000      1010      1020
CTCTCCGGCTACGGCAAGCATGAGGCCTTGTCTCCTTTCTATTCGGAGCGGCTGAAGGAG
LeuSerGlyTyrGlyLysHisGluAlaLeuSerProPheTyrSerGluArgLeuLysGlu 1030      1040      1050      1060      1070      1080
GCTCATGTCAGACTGTACCCATCCAGCCGCTGCACATCACAACATTTACTTAACAGAACA
AlaHisValArgLeuTyrProSerSerArgCysThrSerGlnHisLeuLeuAsnArgThr 1090      1100      1110      1120      1130      1140
GTCACCGACAACATGCTGTGTGCTGGAGACACTCGGAGCGGCGGGCCCCAGGCAAACTTG
ValThrAspAsnMetLeuCysAlaGlyAspThrArgSerGlyGlyProGlnAlaAsnLeu 1150      1160      1170      1180      1190      1200
CACGACGCCTGCCAGGGCGATTCGGGAGGCCCCCTGGTGTGTCTGAACGATGGCCGCATG
HisAspAlaCysGlnGlyAspSerGlyGlyProLeuValCysLeuAsnAspGlyArgMet 1210      1220      1230      1240      1250      1260
ACTTTGGTGGGCATCATCAGCTGGGGCCTGGGCTGTGGACAGAAGGATGTCCCGGGTGTG
ThrLeuValGlyIleIleSerTrpGluLeuGlyCysGlyGlnLysAspValProGlyVal 1270      1280      1290      1300      1310
TACACAAAGGTTACCAACTACCTAGACTGGATTCGTGACAACATGCGACCGTGA  - 3'
TyrThrLysValThrAsnTyrLeuAspTrpIleArgAspAsnMetArgPro***
                                                      ←|
```

FIG. 34B

```
             10         20        30        40        50        60
5' - ATGTGTTATGAGGACCAGGGCATCAGCTACAGGGGCACGTGGAGCACAGCGGAGAGTGGC
     MetCysTyrGluAspGlnGlyIleSerTyrArgGlyThrTrpSerThrAlaGluSerGly
     |→ STQitPA
             70        80        90       100       110       120
     GCCGAGTGCACCAACTGGAACAGCAGCGCGTTGGCCCAGAAGCCCTACAGCGGGCGGAGG
     AlaGluCysThrAsnTrpAsnSerSerAlaLeuAlaGlnLysProTyrSerGlyArgArg 130       140       150       160       170       180
     CCAGACGCCATCAGGCTGGGCCTGGGGAACCACAACTACTGCAGAAACCCAGATCGAGAC
     ProAspAlaIleArgLeuGlyLeuGlyAsnHisAsnTyrCysArgAsnProAspArgAsp 190       200       210       220       230       240
     TCAAAGCCCTGGTGCTACGTCTTTAAGGCGGGGAAGTACAGCTCAGAGTTCTGCAGCACC
     SerLysProTrpCysTyrValPheLysAlaGlyLysTyrSerSerGluPheCysSerThr 250       260       270       280       290       300
     CCTGCCTGCTCTGAGGGAAACAGTGACTGCTACTTTGGGAATGGGTCAGCCTACCGTGGC
     ProAlaCysSerGluGlyAsnSerAspCysTyrPheGlyAsnGlySerAlaTyrArgGly 310       320       330       340       350       360
     ACGCACAGCCTCACCGAGTCGGGTGCCTCCTGCCTCCCGTGGAATTCCATGATCCTGATA
     ThrHisSerLeuThrGluSerGlyAlaSerCysLeuProTrpAsnSerMetIleLeuIle 370       380       390       400       410       420
     GGCAAGGTTTACACAGCACAGAACCCCAGTGCCCAGGCACTGGGCCTGGGCAAACATAAT
     GlyLysValTyrThrAlaGlnAsnProSerAlaGlnAlaLeuGlyLeuGlyLysHisAsn 430       440       450       460       470       480
     TACTGCCGGAATCCTGATGGGGATGCCAAGCCCTGGTGCCACGTGCTGAAGAACCGCAGG
     TyrCysArgAsnProAspGlyAspAlaLysProTrpCysHisValLeuLysAsnArgArg 490       500       510       520       530       540
     CTGACGTGGGAGTACTGTGATGTGCCCTCCTGCTCCACCTGCGGCCTGAGACAGTACAGC
     LeuThrTrpGluTyrCysAspValProSerCysSerThrCysGlyLeuArgGlnTyrSer 550       560       570       580       590       600
     CAGCCTCAGTTTCGCATCAAAGGAGGGCTCTTCGCCGACATCGCCTCCCACCCCTGGCAG
     GlnProGlnPheArgIleLysGlyGlyLeuPheAlaAspIleAlaSerHisProTrpGln 610       620       630       640       650       660
     GCTGCCATCTTTGCCAAGCACAGGAGGTCGCCCGGAGAGCGGTTCCTGTGCGGGGGCATA
     AlaAlaIlePheAlaLysHisArgArgSerProGlyGluArgPheLeuCysGlyGlyIle
```

FIG.35A

```
        670       680       690       700       710       720
CTCATCAGCTCCTGCTGGATTCTCTCTGCCGCCCACTGCTTCCAGGAGAGGTTTCCGCCC
LeuIleSerSerCysTrpIleLeuSerAlaAlaHisCysPheGlnGluArgPheProPro 730       740       750       760       770       780
CACCACCTGACGGTGATCTTGGGCAGAACATACCGGGTGGTCCCTGGCGAGGAGGAGCAG
HisHisLeuThrValIleLeuGlyArgThrTyrArgValValProGlyGluGluGluGln 790       800       810       820       830       840
AAATTTGAAGTCGAAAAATACATTGTCCATAAGGAATTCGATGATGACACTTACGACAAT
LysPheGluValGluLysTyrIleValHisLysGluPheAspAspAspThrTyrAspAsn 850       860       870       880       890       900
GACATTGCGCTGCTGCAGCTGAAATCGGATTCGTCCCGCTGTGCCCAGGAGAGCAGCGTG
AspIleAlaLeuLeuGlnLueLysSerAspSerSerArgCysAlaGlnGluSerSerVal 910       920       930       940       950       960
GTCCGCACTGTGTGCCTTCCCCCGGCGGACCTGCAGCTGCCGGACTGGACGGAGTGTGAG
ValArgThrValCysLeuProProAlaAspLeuGlnLeuProAspTrpThrGluCysGlu 970       980       990       1000      1010      1020
CTCTCCGGCTACGGCAAGCATGAGGCCTTGTCTCCTTTCTATTCGGAGCGGCTGAAGGAG
LeuSerGlyTyrGlyLysHisGluAlaLeuSerProPheTyrSerGluArgLeuLysGlu 1030      1040      1050      1060      1070      1080
GCTCATGTCAGACTGTACCCATCCAGCCGCTGCACATCACAACATTTACTTAACAGAACA
AlaHisValArgLeuTyrProSerSerArgCysThrSerGlnHisLeuLeuAsnArgThr 1090      1100      1110      1120      1130      1140
GTCACCGACAACATGCTGTGTGCTGGAGACACTCGGAGCGGCGGGCCCCAGGCAAACTTG
ValThrAspAsnMetLeuCysAlaGlyAspThrArgSerGlyGlyProGlnAlaAsnLeu 1150      1160      1170      1180      1190      1200
CACGACGCCTGCCAGGGCGATTCGGGAGGCCCCCTGGTGTGTCTGAACGATGGCCGCATG
HisAspAlaCysGlnGlyAspSerGlyGlyProLeuValCysLeuAsnAspGlyArgMet 1210      1220      1230      1240      1250      1260
ACTTTGGTGGGCATCATCAGCTGGGGCCTGGGCTGTGGACAGAAGGATGTCCCGGGTGTG
ThrLeuValGlyIleIleSerTrpGluLeuGlyCysGlyGlnLysAspValProGlyVal 1270      1280      1290      1300      1310
TACACAAAGGTTACCAACTACCTAGACTGGATTCGTGACAACATGCGACCGTGA - 3'
TyrThrLysValThrAsnTyrLeuAspTrpIleArgAspAsnMetArgPro***
```

FIG.35B

```
            10        20        30        40        50        60
5' - ATGTCTGAGGGAAACAGTGACTGCTACTTTGGGAATGGGTCAGCCTACCGTGGCACGCAC
     MetSerGluGlyAsnSerAspCysTyrPheGlyAsnGlySerAlaTyrArgGlyThrHis
     |→ UTTtPA
            70        80        90       100       110       120
     AGCCTCACCGAGTCGGGTGCCTCCTGCCTCCCGTGGAATTCCATGATCCTGATAGGCAAG
     SerLeuThrGluSerGlyAlaSerCysLeuProTrpAsnSerMetIleLeuIleGlyLys 130       140       150       160       170       180
     GTTTACACAGCACAGAACCCCAGTGCCCAGGCACTGGGCCTGGGCAAACATAATTACTGC
     ValTyrThrAlaGlnAsnProSerAlaGlnAlaLeuGlyLeuGlyLysHisAsnTyrCys 190       200       210       220       230       240
     CGGAATCCTGATGGGGATGCCAAGCCCTGGTGCCACGTGCTGAAGAACCGCAGGCTGACG
     ArgAsnProAspGlyAspAlaLysProTrpCysHisValLeuLysAsnArgArgLeuThr 250       260       270       280       290       300
     TGGGAGTACTGTGATGTGCCCTCCTGCTCCACCTGCGGCCTGAGACAGACTCTGCGTCCG
     TrpGluTyrCysAspValProSerCysSerThrCysGlyLeuArgGlnThrLeuArgPro 310       320       330       340       350       360
     GGFTTCAAAATCAAAGGAGGCCTCTTCGCCGACATCGCCTCCCACCCCTGGCAGGCTGCC
     ArgPheLysIleLysGlyGlyLeuPheAlaAspIleAlaSerHisProTrpGlnAlaAla 370       380       390       400       410       420
     ATCTTTGCCAAGCACAGGAGGTCGCCCGGAGAGCGGTTCCTGTGCGGGGGCATACTCATC
     IlePheAlaLysHisArgArgSerProGlyGluArgPheLeuCysGlyGlyIleLeuIle 430       440       450       460       470       480
     AGCTCCTGCTGGATTCTCTCTGCCGCCCACTGCTTCCAGGAGAGGTTTCCGCCCCACCAC
     SerSerCysTrpIleLeuSerAlaAlaHisCysPheGlnGluArgPheProProHisHis 490       500       510       520       530       540
     CTGACGGTGATCTTGGGCAGAACATACCGGGTGGTCCCTGGCGAGGAGGAGCAGAAATTT
     LeuThrValIleLeuGlyArgThrTyrArgValValProGlyGluGluGluGlnLysPhe 550       560       570       580       590       600
     GAAGTCGAAAAATACATTGTCCATAAGGAATTCGATGATGACACTTACGACAATGACATT
     GluValGluLysTyrIleValHisLysGluPheAspAspAspThrTyrAspAsnAspIle 610       620       630       640       650       660
     GCGCTGCTGCAGCTGAAATCGGATTCGTCCCGCTGTGCCCAGGAGAGCAGCGTGGTCCGC
     AlaLeuLeuGlnLeuLysSerAspSerSerArgCysAlaGlnGluSerSerValValArg
```

FIG.36A

```
         670       680       690       700       710       720
ACTGTGTGCCTTCCCCCGGCGGACCTGCAGCTGCCGGACTGGACGGAGTGTGAGCTCTCT
ThrValCysLeuProProAlaAspLeuGlnLeuProAspTrpThrGluCysGluLeuSer 730       740       750       760       770       780
GGCTACGGCAAGCATGAGGCCTTGTCTCCTTTCTATTCGGAGCGGCTGAAGGAGGCTCAT
GlyTyrGlyLysHisGluAlaLeuSerProPheTyrSerGluArgLeuLysGluAlaHis 790       800       810       820       830       840
GTCAGACTGTACCCATCCAGCCGCTGCACATCACAACATTTACTTAACAGAACAGTCACC
ValArgLeuTyrProSerSerArgCysThrSerGlnHisLeuLeuAsnArgThrValThr 850       860       870       880       890       900
GACAACATGCTGTGTGCTGGAGACACTCGGAGCGGCGGGCCCCAGGCAAACTTGCACGAC
AspAsnMetLeuCysAlaGlyAspThrArgSerGlyGlyProGlnAlaAsnLeuHisAsp 910       920       930       940       950       960
GCCTGCCAGGGCGATTCGGGAGGCCCCCTGGTGTGTCTGAACGATGGCCGCATGACTTTG
AlaCysGlnGlyAspSerGlyGlyProLeuValCysLeuAsnAspGlyArgMetThrLeu 970       980       990      1000      1010      1020
GTGGGCATCATCAGCTGGGGCCTGGGCTGTGGACAGAAGGATGTCCCGGGTGTGTACACA
ValGlyIleIleSerTrpGlyLeuGlyCysGlyGlnLysAspValProGlyValTyrThr 1030      1040      1050      1060      1070
AAGGTTACCAACTACCTAGACTGGATTCGTGACAACATGCGACCGTGA  - 3'
LysValThrAsnTyrLeuAspTrpIleArgAspAsnMetArgPro***
                                              ←|
```

FIG.36B

```
                10         20         30         40         50         60
5' - ATGTCTGAGGGAAACAGTGACTGCTACTTTGGGAATGGGTCAGCCTACCGTGGCACGCAC
     MetSerGluGlyAsnSerAspCysTyrPheGLyAsnGlySerAlaTyrArgGlyThrHis
     |→ thTTtPA
                70         80         90        100        110        120
     AGCCTCACCGAGTCGGGTGCCTCCTGCCTCCCGTGGAATTCCATGATCCTGATAGGCAAG
     SerLeuThrGluSerGlyAlaSerCysLeuProTrpAsnSerMetIleLeuIleGlyLys 130        140        150        160        170        180
     GTTTACACAGCACAGAACCCCAGTGCCCAGGCACTGGGCCTGGGCAAACATAATTACTGC
     ValTyrThrAlaGlnAsnProSerAlaGlnAlaLeuGlyLeuGlyLysHisAsnTyrCys 190        200        210        220        230        240
     CGGAATCCTGATGGGGATGCCAAGCCCTGGTGCCACGTGCTGAAGAACCGCAGGCTGACG
     ArgAsnProAspGlyAspAlaLysProTrpCysHisValLeuLysAsnArgArgLeuThr 250        260        270        280        290        300
     TGGGAGTACTGTGATGTGCCCTCCTGCTCCACCTGCGGCCTGAGACAGTACAGCCAGCCA
     TrpGluTyrCysAspValProSerCysSerThrCysGlyLeuArgGlnTyrSerGlnPro 310        320        330        340        350        360
     ATTCCTAGATCTGGAGGCCTCTTCGCCGACATCGCCTCCCACCCCTGGCAGGCTGCCATC
     IleProArgSerGlyGlyLeuPheAlaAspIleAlaSerHisProTrpGlnAlaAlaIle 370        380        390        400        410        420
     TTTGCCAAGCACAGGAGGTCGCCCGGAGAGCGGTTCCTGTGCGGGGGGCATACTATCAGC
     PheAlaLysHisArgArgSerProGlyGluArgPheLeuCysGlyGlyIleLeuIleSer 430        440        450        460        470        480
     TCCTGCTGGATTCTCTCTGCCGCCCACTGCTTCCAGGAGAGGTTTCCGCCCCACCACCTG
     SerCysTrpIleLeuSerAlaAlaHisCysPheGlnGluArgPheProProHisHisLeu 490        500        510        520        530        540
     ACGGTGATCTTGGGCAGAACATACCGGGTGGTCCCTGGCGAGGAGGAGCAGAAATTTGAA
     ThrValIleLeuGlyArgThrTyrArgValValProGlyGluGluGluGlnLysPheGlu 550        560        570        580        590        600
     GTCGAAAAATACATTGTCCATAAGGAATTCGATGATGACACTTACGACAATGACATTGCG
     ValGluLysTyrIleValHisLysGluPheAspAspAspThrTyrAspAsnAspIleAla 610        620        630        640        650        660
     CTGCTGCAGCTGAAATCGGATTCGTCCCGCTGTGCCCAGGAGAGCAGCGTGGTCCGCACT
     LeuLeuGlnLeuLysSerAspSerSerArgCysAlaGlnGluLeuSerValValArgThr
```

FIG.37A

```
         670       680       690       700       710       720
GTGTGCCTTCCCCCGGCGGACCTGCAGCTGCCGGACTGGACGGAGTGTGAGCTCTCCGGC
ValCysLeuProProAlaAspLeuGlnLeuProAspTrpThrGluCysGluLeuSerGly 730       740       750       760       770       780
TACGGCAAGCATGAGGCCTTGTCTCCTTTCTATTCGGAGCGGCTGAAGGAGGCTCATGTC
TyrGlyLysHisGluAlaLeuSerProPheTyrSerGluArgLeuLysGluAlaHisVal 790       800       810       820       830       840
AGACTGTACCATCCAGCCGCTGCACATCACAACARTTTACTTAACAGAACAGTCACCGAC
ArgLeuTyrProSerSerArgCysThrSerGlnHisLeuLeuAsnArgThrValThrAsp 850       860       870       880       890       900
AACATGCTGTGTGCTGGAGACACTCGGAGCGGCGGGCCCCAGGCAAACTTGCACGACGCC
AsnMetLeuCysAlaGlyAspThrArgSerGlyGlyProGlnAlaAsnLeuHisAspAla 910       920       930       940       950       960
TGCCAGGGCGATTCGGGAGGCCCCCTGGTGTGTCTGAACGATGGCCGCATGACTTTGGTG
CysGlnGlyAspSerGlyGlyProLeuValCysLeuAsnAspGlyArgMetThrLeuVal 970       980       990      1000      1010      1020
GGCATCATCAGCTGGGGCCTGGGCTGTGGACAGAAGGATGTCCCGGGTGTGTACACAAAG
GlyIleIleSerTrpGluLeuGlyCysGlyGlnLysAspValProGlyValTyrThrLys 1030      1040      1050      1060
GTTACCAACTACCTAGACTGGATTCGTGACAACATGCGACCGTGA - 3'
ValThrAsnTyrLeuAspTrpIleArgAspAsnMetArgPro***
```

FIG.37B

```
             10        20        30        40        50        60
5' - ATGGATGCAATGAAGAGAGGGCTCTGCTGTGTGCTGCTGCTGTGTGGAGCAGTCTTCGTT
     MetAspAlaMetLysArgGlyLeuCysCysValLeuLeuLeuCysGlyAlaValPheVal 70        80        90       100       110       120
     TCGCCCAGCCAGGAAATCCATGCCCGATTCAGAAGAGGAGCCAGATCTTGCTACGAGGAC
     SerProSerGlnGluIleHisAlaArgPheArgArgGlyAlaArgSerCysTyrGluAsp
                                                  |→ mTQktPA
            130       140       150       160       170       180
     CAGGGCATCAGCTACAGGGGCACGTGGAGCACAGCGGAGAGTGGCGCCGAGTGCACCAAC
     GlnGlyIleSerTyrArgGlyThrTrpSerThrAlaGluSerGlyAlaGluCysThrAsn 190       200       210       220       230       240
     TGGAACAGCAGCGCGTTGGCCCAGAAGCCCTACAGCGGGCGGAGGCCAGACGCCATCAGG
     TrpAsnSerSerAlaLeuAlaGlnLysProTyrSerGlyArgArgProAspAlaIleArg 250       260       270       280       290       300
     CTGGGCCTGGGGAACCACAACTACTGCAGAAACCCAGATCGAGACTCAAAGCCCTGGTGC
     LeuGlyLeuGlyAsnHisAsnTyrCysArgAsnProAspArgAspSerLysProTrpCys 310       320       330       340       350       360
     TACGTCTTTAAGGCGGGGAAGTACAGCTCAGAGTTCTGCAGCACCCCTGCCTGCTCTGAG
     TyrValPheLysAlaGlyLysTyrSerSerGluPheCysSerThrProAlaCysSerGlu 370       380       390       400       410       420
     GGAAACAGTGACTGCTACTTTGGGAATGGGTCAGCCTACCGTGGCACGCACAGCCTCACC
     GlyAsnSerAspCysTyrPheGlyAsnGlySerAlaTyrArgGlyThrHisSerLeuThr 430       440       450       460       470       480
     GAGTCGGGTGCCTCCTGCCTCCCGTGGAATTCCATGATCCTGATAGGCAAGGTTTACACA
     GluSerGlyAlaSerCysLeuProTrpAsnSerMetIleLeuIleGlyLysValTyrThr 490       500       510       520       530       540
     GCACAGAACCCCAGTGCCCAGGCACTGGGCCTGGGCAAACATAATTACTGCCGGAATCCT
     AlaGlnAsnProSerAlaGlnAlaLeuGlyLeuGlyLysHisAsnTyrCysArgAsnPro 550       560       570       580       590       600
     GATGGGGATGCCAAGCCCTGGTGCCACGTGCTGAAGAACCGCAGGCTGACGTGGGAGTAC
     AspGlyAspAlaLysProTrpCysHisValLeuLysAsnArgArgLeuThrTrpGluTyr 610       620       630       640       650       660
     TGTGATGTGCCCTCCTGCTCCACCTGCGGCCTGAGACAGTACAGCCAGCCTCAGTTTCGC
     CysAspValProSerCysSerThrCysGlyLeuArgGlnTyrSerGlnProGlnPheArg
```

FIG.38A

```
       670       680       690       700       710       720
ATCAAAGGAGGGCTCTTCGCCGACATCGCCTCCCACCCCTGGCAGGCTGCCATCTTTGCC
IleLysGlyGlyLeuPheAlaAspIleAlaSerHisProTrpGlnAlaAlaIlePheAla 730       740       750       760       770       780
AAGCACAGGAGGTCGCCCGGAGAGCGGTTCCTGTGCGGGGGCATACTCATCAGCTCCTGC
LysHisArgArgSerProGlyGluArgPheLeuCysGlyGlyIleLeuIleSerSerCys 790       800       810       820       830       840
TGGATTCTCTCTGCCGCCCACTGCTTCCAGGAGAGGTTTCCGCCCCACCACCTGACGGTG
TrpIleLeuSerAlaAlaHisCysPheGlnGluArgPheProProHisHisLeuThrVal 850       860       870       880       890       900
ATCTTGGGCAGAACATACCGGGTGGTCCCTGGCGAGGAGGAGCAGAAATTTGAAGTCGAA
IleLeuGlyArgThrTyrArgValValProGlyGluGluGluGlnLysPheGluValGlu 910       920       930       940       950       960
AAATACATTGTCCATAAGGAATTCGATGATGACACTTACGACAATGACATTGCGCTGCTG
LysTyrIleValHisLysGluPheAspAspAspThrTyrAspAsnAspIleAlaLeuLeu 970       980       990      1000      1010      1020
CAGCTGAAATCGGATTCGTCCCGCTGTGCCCAGGAGAGCAGCGTGGTCCGCACTGTGTGC
GlnLeuLysSerAspSerSerArgCysAlaGlnGluSerSerValValArgThrValCys 1030      1040      1050      1060      1070      1080
CTTCCCCCGGCGGACCTGCAGCTGCCGGACTGGACGGAGTGTGAGCTCTCCGGCTACGGC
LeuProProAlaAspLeuGlnLeuProAspTrpThrGluCysGluLeuSerGlyTyrGly 1090      1100      1110      1120      1130      1140
AAGCATGAGGCCTTGTCTCCTTTCTATTCGGAGCGGCTGAAGGAGGCTCATGTCAGACTG
LysHisGluAlaLeuSerProPheTyrSerGluArgLeuLysGluAlaHisValArgLeu 1150      1160      1170      1180      1190      1200
TACCCATCCAGCCGCTGCACATCACAACATTTACTTAACAGAACAGTCACCGACAACATG
TyrProSerSerArgCysThrSerGlnHisLeuLeuAsnArgThrValThrAspAsnMet 1210      1220      1230      1240      1250      1260
CTGTGTGCTGGAGACACTCGGAGCGGCGGGCCCCAGGCAAACTTGCACGACGCCTGCCAG
LeuCysAlaGlyAspThrArgSerGlyGlyProGlnAlaAsnLeuHisAspAlaCysGln 1270      1280      1290      1300      1310      1320
GGCGATTCTGGAGGCCCCCTGGTGTGTCTGAACGATGGCCGCATGACTTTGGTGGGCATC
GlyAspSerGlyGlyProLeuValCysLeuAsnAspGlyArgMetThrLeuValGlyIle
```

FIG.38B

```
        1330      1340      1350      1360      1370      1380
ATCAGCTGGGGCCTGGGCTGTGGACAGAAGGATGTCCCGGGTGTGTACACAAAGGTTACC
IleSerTrpGlyLeuGlyCysGlyGlnLysAspValProGlyValTyrThrLysValThr 1390      1400      1410      1420
AACTACCTAGACTGGATTCGTGACAACATGCGACCGTGA - 3'
AsnTyrLeuAspTrpIleArgAspAsnMetArgPro***
                                       ←|
```

FIG.38C

```
              10        20        30        40        50        60
5' - ATGGATGCAATGAAGAGAGGGCTCTGCTGTGTGCTGCTGCTGTGTGGAGCAGTCTTGCTT
     MetAspAlaMetLysArgGlyLeuCysCysValLeuLeuLeuCysGlyAlaValPheVal 70        80        90       100       110       120
     TCGCCCAGCCAGGAAATCCATGCCCGATTCAGAAGAGGAGCCAGATCTGAGGGAAACAGT
     SerProSerGlnGluIleHisAlaArgPheArgArgGlyAlaArgSerGluGlyAsnSer
                                                  |→ TTktPA
             130       140       150       160       170       180
     GACTGCTACTTTGGGAATGGGTCAGCCTACCGTGGCACGCACAGCCTCACCGAGTCGGGT
     AspCysTyrPheGlyAsnGlySerAlaTyrArgGlyThrHisSerLeuThrGluSerGly 190       200       210       220       230       240
     GCCTCCTGCCTCCCGTGGAATTCCATGATCCTGATAGGCAAGGTTTACACAGCACAGAAC
     AlaSerCysLeuProTrpAsnSerMetIleLeuIleGlyLysValTyrThrAlaGlnAsn 250       260       270       280       290       300
     CCCAGTGCCCAGGCACTGGGCCTGGGCAAACATAATTACTGCCGGAATCCTGATGGGGAT
     ProSerAlaGlnAlaLeuGlyLeuGlyLysHisAsnTyrCysArgAsnProAspGlyAsp 310       320       330       340       350       360
     GCCAAGCCCTGGTGCCACGTGCTGAAGAACCGCAGGCTGACGTGGGAGTACTGTGATGTG
     AlaLysProTrpCysHisValLeuLysAsnArgArgLeuThrTrpGluTyrCysAspVal 370       380       390       400       410       420
     CCCTCCTGCTCCACCTGCGGCCTGAGACAGTACAGCCAGCCTCAGTTTCGCATCAAAGGA
     ProSerCysSerThrCysGlyLeuArgGlnTyrSerGlnProGlnPheArgIleLysGly 430       440       450       460       470       480
     GGGCTCTTCGCCGACATCGCCTCCCACCCCTGGCAGGCTGCCATCTTTGCCAAGCACAGG
     GluLeuPheAlaAspIleAlaSerHisProTrpGlnAlaAlaIlePheAlaLysHisArg 490       500       510       520       530       540
     AGGTCGCCCGGAGAGCGGTTCCTGTGCGGGGGCATACTCATCAGCTCCTGCTGGATTCTC
     ArgSerProGlyGluArgPheLeuCysGlyGlyIleLeuIleSerSerCysTrpIleLeu 550       560       570       580       590       600
     TCTGCCGCCCACTGCTTCCAGGAGAGGTTTCCGCCCCACCACCTGACGGTGATCTTGGGC
     SerAlaAlaHisCysPheGlnGluArgPheProProHisHisLeuThrValIleLeuGly 610       620       630       640       650       660
     AGAACATACCGGGTGGTCCCTGGCGAGGAGGAGCAGAAATTTGAAGTCGAAAAATACATT
     ArgThrTyrArgValValProGlyGluGluGluGlnLysPheGluValGluLysTyrIle
```

FIG.39A

```
       670       680       690       700       710       720
GTCCATAAGGAATTCGATGATGACACTTACGACAATGACATTGCGCTGCTGCAGCTGAAA
ValHisLysGluPheAspAspAspThrTyrAspAsnAspIleAlaLeuLeuGlnLeuLys 730       740       750       760       770       780
TCGGATTCGTCCCGCTGTGCCCAGGAGAGCAGCGTGGTCCGCACTGTGTGCCTTCCCCCG
SerAspSerSerArgCysAlaGlnGluSerSerValValArgThrValCysLeuProPro 790       800       810       820       830       840
GCGGACCTGCAGCTGCCGGACTGGACGGAGTGTGAGCTCTCCGGCTACGGCAAGCATGAG
AlaAspLeuGlnLeuProAspTrpThrGluCysGluLeuSerGlyTyrGlyLysHisGlu 850       860       870       880       890       900
GCCTTGTCTCCTTTCTATTCGGAGCGGCTGAAGGAGGCTCATGTCAGACTGTACCCATCC
AlaLeuSerProPheTyrSerGluArgLeuLysGluAlaHisValArgLeuTyrProSer 910       920       930       940       950       960
AGCCGCTGCACATCACAACATTTACTTAACAGAACAGTCACCGACAACATGCTGTGTGCT
SerArgCysThrSerGlnHisLeuLeuAsnArgThrValThrAspAsnMetLeuCysAla 970       980       990      1000      1010      1020
GGAGACACTCGGAGCGGCGGGCCCCAGGCAAACTTGCACGACGCCTGCCAGGGCGATTCG
GlyAspThrArgSerGlyGlyProGlnAlaAsnLeuHisAspAlaCysGlnGlyAspSer 1030      1040      1050      1060      1070      1080
GGAGGCCCCCTGGTGTGTCTGAACGATGGCCGCATGACTTTGGTGGGCATCATCAGCTGG
GlyGlyProLeuValCysLeuAsnAspGlyArgMetThrLeuValGlyIleIleSerTrp 1090      1100      1110      1120      1130      1140
GGCCTGGGCTGTGGACAGAAGGATGTCCCGGGTGTGTACACAAAGGTTACCAACTACCTA
GlyLeuGlyCysGlyGlnLysAspValProGlyValTyrThrLysValThrAsnTyrLeu 1150      1160      1170
GACTGGATTCGTGACAACATGCGACCGTGA - 3'
AspTrpIleArgAspAsnMetArgPro***
```

FIG.39B

```
              10        20        30        40        50        60
5' - ATGGATGCAATGAAGAGAGGGCTCTGCTGTGTGCTGCTGCTGTGTGGAGCAGTCTTGCTT
     MetAspAlaMetLysArgGlyLeuCysCysValLeuLeuLeuCysGlyAlaValPheVal 70        80        90       100       110       120
     TCGCCCAGCCAGGAAATCCATGCCCGATTCAGAAGAGGAGCCAGATCTGAGGGAAACAGT
     SerProSerGlnGluIleHisAlaArgPheArgArgGlyAlaArgSerGluGlyAsnSer
                                                 |→ STTktPA
             130       140       150       160       170       180
     GACTGCTACTTTGGGAATGGGTCAGCCTACCGTGGCACGCACAGCCTCACCGAGTCGGGT
     AspCysTyrPheGlyAsnGlySerAlaTyrArgGlyThrHisSerLeuThrGluSerGly 190       200       210       220       230       240
     GCCTCCTGCCTCCCGTGGAATTCCATGATCCTGATAGGCAAGGTTTACACAGCACAGAAC
     AlaSerCysLeuProTrpAsnSerMetIleLeuIleGlyLysValTyrThrAlaGlnAsn 250       260       270       280       290       300
     CCCAGTGCCCCAGGCACTGGGCCTGGGCAAACATAATTACTGCCGGAATCCTGATGGGGAT
     ProSerAlaGlnAlaLeuGlyLeuGlyLysHisAsnTyrCysArgAsnProAspGlyAsp 310       320       330       340       350       360
     GCCAAGCCCTGGTGCCACGTGCTGAAGAACCGCAGGCTGACGTGGGAGTACTGTGATGTG
     AlaLysProTrpCysHisValLeuLysAsnArgArgLeuThrTrpGluTyrCysAspVal 370       380       390       400       410       420
     CCCTCCTGCTCCACCTGCGGCCTGAGACAGTACAGCCAGCCACAGTTTGATATCAAAGGA
     ProSerCysSerThrCysGlyLeuArgGlnTyrSerGlnProGlnPheAspIleLysGly 430       440       450       460       470       480
     GGCCTCTTCGCCGACATCGCCTCCCACCCCTGGCAGGCTGCCATCTTTGCCAAGCACAGG
     GlyLeuPheAlaAspIleAlaSerHisProTrpGlnAlaAlaIlePheAlaLysHisArg 490       500       510       520       530       540
     AGGTCGCCCGGAGAGCGGTTCCTGTGCGGGGGCATACTCATCAGCTCCTGCTGGATTCTC
     ArgSerProGlyGluArgPheLeuCysGlyGlyIleLeuIleSerSerCysTrpIleLeu 550       560       570       580       590       600
     TCTGCCGCCCACTGCTTCCAGGAGAGGTTTCCGCCCCACCACCTGACGGTGATCTTGGGC
     SerAlaAlaHisCysPheGlnGluArgPheProProHisHisLeuThrValIleLeuGly 610       620       630       640       650       660
     AGAACATACCGGGTGGTCCCTGGCGAGGAGGAGCAGAAATTTGAAGTCGAAAAATACATT
     ArgThrTyrArgValValProGlyGluGluGluGlnLysPheGluValGluLysTyrIle
```

FIG.40A

```
      670       680       690       700       710       720
GTCCATAAGGAATTCGATGATGACACTTACGACAATGACATTGCGCTGCTGCAGCTGAAA
ValHisLysGluPheAspAspAspThrTyrAspAsnAspIleAlaLeuLeuGlnLeuLys 730       740       750       760       770       780
TCGGATTCGTCCCGCTGTGCCCAGGAGAGCAGCGTGGTCCGCACTGTGTGCCTTCCCCCG
SerAspSerSerArgCysAlaGlnGluSerSerValValArgThrValCysLeuProPro 790       800       810       820       830       840
GCGGACCTGCAGCTGCCGGACTGGACGGAGTGTGAGCTCTCCGGCTACGGCAAGCATGAG
AlaAspLeuGlnLeuProAspTrpThrGluCysGluLeuSerGlyTyrGlyLysHisGlu 850       860       870       880       890       900
GCCTTGTCTCCTTTCTATTCGGAGCGGCTGAAGGAGGCTCATGTCAGACTGTACCCATCC
AlaLeuSerProPheTyrSerGluArgLeuLysGluAlaHisValArgLeuTyrProSer 910       920       930       940       950       960
AGCCGCTGCACATCACAACATTTACTTAACAGAACAGTCACCGACAACATGCTGTGTGCT
SerArgCysThrSerGlnHisLeuLeuAsnArgThrValThrAspAsnMetLeuCysAla 970       980       990      1000      1010      1020
GGAGACACTCGGAGCGGCGGGCCCCAGGCAAACTTGCACGACGCCTGCCAGGGCGATTCG
GlyAspThrArgSerGlyGlyProGlnAlaAsnLeuHisAspAlaCysGlnGlyAspSer 1030      1040      1050      1060      1070      1080
GGAGGCCCCCTGGTGTGTCTGAACGATGGCCGCATGACTTTGGTGGGCATCATCAGCTGG
GlyGLyProLeuValCysLeuAsnAspGlyArgMetThrLeuValGlyIleIleSerTrp 1090      1100      1110      1120      1130      1140
GGCCTGGGCTGTGGACAGAAGGATGTCCCGGGTGTGTACACAAAGGTTACCAACTACCTA
GlyLeuGlyCysGlyGlnLysAspValProGlyValTyrThrLysValThrAsnTyrLeu 1150      1160      1170
GACTGGATTCGTGACAACATGCGACCGTGA - 3'
AspTrpIleArgAspAsnMetArgPro***
                              ←|
```

FIG.40B

TISSUE PLASMINOGEN ACTIVATOR

This application is a continuation of application Ser. No. 08/238,796, filed on May 6, 1994, now abandoned; which is a continuation of Ser. No. 08/131,672, filed Oct. 5, 1993, abandoned; which is a continuation of Ser. No. 07/991,714, filed Dec. 16, 1992, abandoned; which is a continuation of Ser. No. 07/879,736, filed May 6, 1992, abandoned; which is a continuation of Ser. No. 07/711,410 filed Jun. 5, 1991, abandoned; which is a continuation of Ser. No. 07/227,149 filed Aug. 2, 1988, abandoned.

This invention relates to a new tissue plasminogen activator. More particularly, it relates to a new tissue plasminogen activator which has strong activity for converting plasminogen into plasmin that degrades the fibrin network of blood clots to form soluble products and therefore is useful as a thrombolytic agent, to a DNA sequence encoding an amino acid sequence for it, to a process for producing it and pharmaceutical composition comprising it.

The whole amino acid sequence and structure of a native human "tissue plasminogen activator" (hereinafter referred to as "t-PA") and DNA sequence coding for it derived from a human melanoma cell (Bowes) have already been clarified by recombinant DNA technology [Cf. Nature 301, 214 (1983)].

However, the native t-PA obtained by expressing DNA encoding amino acid sequence of the native t-PA in *E. coli* can hardly be refolded and therefore only an extremely small quantity of the active t-PA can be recovered from the cultured cells of the *E. coli*.

From the results of various investigations, inventors of this invention succeeded in producing new t-PA which is well refolded, even in a form of the resultant product obtained from the *E. coli* cells to give an active t-PA, and display a longer half-life and has a stronger thrombolytic activity than the native t-PA.

The new t-PA of this invention may be represented by the following amino acid sequence (I) as its primary structure.

```
                180                    190
R—GluGlyAsnSerAspCysTyrPheGlyAsnGlySer AlaTyrArgGlyThrHis Ser 200                    210
LeuThrGluSerGlyAlaSerCysLeuProTrpAsnSerMetIleLeuIleGlyLysVal 220                    230
TyrThrAlaGlnAsnProSerAlaGlnAlaLeuGlyLeuGlyLysHisAsnTyrCysArg 240                    250
AsnProAspGlyAspAlaLysProTrpCysHisValLeuLysAsnArgArgLeuThrTrp 260                    270
GluTyrCysAspValProSerCysSerThrCysGlyLeuArgGln—Y—

277   280                      290
—X—GlyGlyLeuPheAlaAspIleAlaSerHis ProTrpGlnAlaAlaIle 300                    310
PheAlaLysHisArgArgSerProGlyGluArgPheLeuCysGlyGlyIleLeuIleSer 320                    330
SerCysTrpIleLeuSerAlaAlaHisCysPheGlnGluArgPheProProHisHisLeu 340                    350
ThrValIleLeuGlyArgThrTyrArgValValProGlyGluGluGluGlnLysPheGlu 360                    370
ValGluLysTyrIleValHisLysGluPheAspAspAspThrTyrAspAsnAspIleAla 380                    390
LeuLeuGlnLeuLysSerAspSerSerArgCysAlaGlnGluSerSerValValArgThr 400                    410
ValCysLeuProProAlaAspLeuGlnLeuProAspTrpThrGluCysGluLeuSerGly 420                    430
TyrGlyLysHisGluAlaLeuSerProPheTyrSerGluArgLeuLysGluAlaHisVal 440                    450
ArgLeuTyrProSerSerArgCysThrSerGlnHisLeuLeuAsnArgThrValThrAsp 460                    470
AsnMetLeuCysAlaGlyAspThrArgSerGlyGlyProGlnAlaAsnLeuHisAspAla 480                    490
CysGlnGlyAspSerGlyGlyProLeuValCysLeuAsnAspGlyArgMetThrLeuVal 500                    510
GlyIleIleSerTrpGlyLeuGlyCysGlyGlnLysAspValProGlyValTyrThrLys 520                    527
ValThrAsnTyrLeuAspTrpIleArgAspAsnMetArgPro 92                    100
wherein R is Ser— or CysTyrGluAspGlnGlyIleSerTyrArgGlyThrTrp 110                    120
SerThrAlaGluSerGlyAlaGluCysThrAsnTrpAsnSerSerAlaLeuAlaGlnLys 130                    140
ProTyrSerGlyArgArgProAspAlaIleArgLeuGlyLeuGlyAsnHisAsnTyrCys 150                    160
ArgAsnProAspArgAspSerLysProTrpCysTyrValPheLysAlaGlyLysTyrSer 170    174
SerGluPheCysSerThrProAlaCysSer—
```

X is -Lys-, -Ile- or bond and
  Y is -TyrSerGlnProGlnPheArgIle-,
      -TyrSerGlnProGlnPheAspIle-,
      -TyrSerGlnProIleProArgSer-     or
      -ThrLeuArgProArgPheLysIle-.

[The numbering of the amino acid sequences of the t-PA is according to that described in Nature 301, 217 (1983)]

In the above amino acid sequence, $Asn^{184}$, $Asn^{218}$ and $Asn^{448}$ may be glycosylated depending on the nature of host cellular environment in the process for the preparation thereof by recombinant DNA technology.

In this specification, the following code names are conveniently employed for the new t-PAs of this invention.

TTktPA

In the above amino acid sequence (I), R is Ser-, X is -Lys- and Y is -TyrSerGlnProGlnPheArgIle-.

TTitPA

In the above amino acid sequence (I), R is Ser-, X is -Ile- and Y is -TyrSerGlnProGlnPheArgIle-.

TQitPA

In the above amino acid sequence (I), R is the residues labelled $Cys^{92}$ to $Ser^{174}$- of the native tPA, X is -Ile- and Y is -TyrSerGlnProGlnPheArgIle-.

TQktPA

In the above amino acid sequence (I), R is the residues labelled $Cys^{92}$ to $Ser^{174}$- of the native tPA, X is -Lys- and Y is -TyrSerGlnProGlnPheArgIle-.

STTktPA

In the above amino acid sequence (I), R is Ser-, X is -Lys- and Y is -TyrSerGlnProGlnPheAspIle-.

STQktPA

In the above amino acid sequence (I), R is the residues labelled $Cys^{92}$ to $Ser^{174}$- of the native tPA, X is -Lys- and Y is -TyrSerGlnProGlnPheAspIle-.

STQitPA

In the above amino acid sequence (I), R is the residues labelled $Cys^{92}$ to $Ser^{174}$- of the native tPA, X is -Ile- and Y is -TyrSerGlnProGlnPheAspIle-.

thTTtPA

In the above amino acid sequence (I), R is Ser-, X is bond and Y is -TyrSerGlnProIleProArgSer-.

uTTtPA

In the above amino acid sequence (I), R is Ser-, X is -Lys- and Y is -ThrLeuArgProArgPheLysIle-.

The native t-PA is a single chain serine protease which is converted to a 2-chain form, heavy and light chains, linked by single disulfide bond with plasmin. The light chain (L) is a protease domain and therefore contains the active-site of the enzyme. The heavy chain (H) has a finger domain (F) (having homology to fibronectin), a growth factor domain (E) (homologous to epidermal growth factor) and two kringles (i.e. kringle 1 and kringle 2 domains; $K_1$ and $K_2$) having triple disulfide bonds. Accordingly, the native t-PA is composed of five functional domains F, E, $K_1$, $K_2$ and L [Cf. European Patent Application laid open No. 0196920 and Proc. Natl. Acad. Sci. U.S.A. 83 4670 (1986)].

Therefore, it is to be understood that this invention also provides (1) finger and growth factor domains lacking t-PA without glycosylation and (2) finger and growth factor domains lacking t-PA essentially free from other proteins of human and animal origin.

The above-defined t-PA includes t-PA essentially consisting of kringle 1 and kringle 2 domains of the heavy chain and the light chain of the native t-PA, and a t-PA prepared by deletion or substitution of the amino acid sequence of said t-PA (e.g. t-PA essentially consisting of kringle 2 domain of the heavy chain and the light chain of the native t-PA, the above-exemplified t-PAs in which $Lys^{277}$ is substituted with $Ile^{277}$, and/or $Arg^{275}$ is substituted with $Gly^{275}$, $Glu^{275}$, $Asp^{275}$, etc.).

The new t-PA of this invention can be prepared by recombinant DNA technology and polypeptide synthesis.

Namely, the new t-PA of this invention can be prepared by culturing a host cell transformed with an expression vector comprising DNA encoding an amino acid sequence of the new t-PA in a nutrient medium, and recovering the new t-PA from the cultured broth.

In the above process, particulars of which are explained in more detail as follows.

The host cell may include a microorganism [bacteria (e.g. *Escherichia coli, Bacillus subtilis*, etc.), yeast (e.g. *Saccharomyces cerevisiae*, etc.)], cultured human and animal cells (e.g. CHO cell, L929 cell, etc.) and cultured plant cells. Preferred examples of the microorganism may include bacteria, especially a strain belonging to the genus Escherichia (e.g. *E. coli* HB 101 ATCC 33694, *E. coli* HB 101-16 FERM BP-1872, *E. coli* 294 ATCC 31446, *E. coli* χ 1776 ATCC 31537, etc.), yeast, animal cell lines(e.g. mouse L929 cell, Chinese hamster ovary(CHO) cell, etc.) and the like.

When the bacterium, especially *E. coli* is used as a host cell, the expression vector is usually comprising at least promoter-operator region, initiation codon, DNA encoding the amino acid sequence of the new t-PA, termination codon, terminator region and replicatable unit. When yeast or animal cell is used as host cell, the expression vector is preferably composed of at least promoter, initiation codon, DNA encoding the amino acid sequence of the signal peptide and the new t-PA and termination codon and it is possible that enhancer sequence, 5'- and 3'-noncoding region of the native t-PA, splicing junctions, polyadenylation site and replicatable unit are also inserted into the expression vector.

The promoter-operator region comprises promoter, operator and Shine-Dalgarno (SD) sequence (e.g. AAGG, etc.) Examples of the promoter-operator region may include conventionally employed promoter-operator region (e.g. lactose-operon, PL-promoter, trp-promoter, etc.) and the promoter for the expression of the new t-PA in mammalian cells may include HTLV-promoter, SV40 early or late-promoter, LTR-promoter, mouse metallothionein I(MMT)-promoter and vaccinia-promoter.

Preferred initiation codon may include methionine codon (ATG).

The DNA encoding signal peptide may include the DNA encoding signal peptide of t-PA.

The DNA encoding the amino acid sequence of the signal peptide or the new t-PA can be prepared in a conventional manner such as a partial or whole DNA synthesis using DNA synthesizer and/or treatment of the complete DNA sequence coding for native or mutant t-PA inserted in a suitable vector (e.g. pTPA21, pTPA25, pTPA102, p51H, pN53, pST112, etc.) obtainable from a transformant [e.g. *E. coli* LE 392 λ⁺ (pTPA21), *E. coli* JA 221 (pTPA 25) ATCC 39808, *E. coli* JA 221 (pTPA 102) (Lys 277 →Ile) ATCC 39811, *E. coli* JM109(p51H) FERM P-9774, *E. coli* JM109(pN53) FERM P-9775, *E. coli* DH-1(pST112) FERM BP-1966, etc.], or genome in a conventional manner (e.g. digestion with restriction enzyme, dephosphorylation with bacterial alkaline phosphatase, ligation using T4 DNA ligase).

The termination codon(s) may include conventionally employed termination codon (e.g. TAG, TGA, etc.).

The terminator region may contain natural or synthetic terminator (e.g. synthetic fd phage terminator, etc.).

The replicatable unit is a DNA sequence capable of replicating the whole DNA sequence belonging thereto in the host cells and may include natural plasmid, artificially modified plasmid (e.g. DNA fragment prepared from natural plasmid) and synthetic plasmid and preferred examples of the plasmid may include plasmid pBR 322 or artificially modified thereof (DNA fragment obtained from a suitable restriction enzyme treatment of pBR 322) for *E. coli*, plasmid pRSVneo ATCC 37198, plasmid pSV2dhfr ATCC 37145 plasmid pdBPV-MMTneo ATCC 37224, plasmid pSV2neo ATCC 37149 for mammalian cell.

The enhancer sequence may include the enhancer sequence (72 bp) of SV40.

The polyadenylation site may include the polyadenlation site of SV40.

The splicing junction may include the splicing junction of SV40.

The promoter-operator region, initiation codon, DNA encoding the amino acid sequence of the new t-PA, termination codon(s) and terminator region can consecutively and circularly be linked with an adequate replicatable unit (plasmid) together, if desired using an adequate DNA fragment(s) (e.g. linker, other restriction site, etc.) in a conventional manner (e.g. digestion with restriction enzyme, phosphorylation using T4 polynucleotide kinase, ligation using T4 DNA-ligase) to give an expression vector. When mammalian cell line is used as a host cell, it is possible that enhancer sequence, promoter, 5'-noncoding region of the cDNA of the native t-PA, initiation codon, DNA encoding amino acid sequences of the signal peptide and the new t-PA, termination codon(s), 3'-noncoding region, splicing junctions and polyadenlation site are consecutively and circularly be linked with an adequate replicatable unit together in the above manner.

The expression vector can be inserted into a host cell. The insertion can be carried out in a conventional manner (e.g. transformation including transfection, microinjection, etc.) to give a transformant including transfectant.

For the production of the new t-PA in the process of this invention, thus obtained transformant comprising the expression vector is cultured in a nutrient medium.

The nutrient medium contains carbon source(s) (e.g. glucose, glycerine, mannitol, fructose, lactose, etc.) and inorganic or organic nitrogen source(s) (e.g. ammonium sulfate, ammonium chloride, hydrolysate of casein, yeast extract, polypeptone, bactotrypton, beef extracts, etc.). If desired, other nutritious sources [e.g. inorganic salts (e.g. sodium or potassium biphosphate, dipotassium hydrogen phosphate, magnesium chloride, magnesium sulfate, calcium chloride), vitamins (e.g. vitamin B1), antibiotics (e.g. ampicillin) etc.] may be added to the medium. For the culture of mammalian cell, Dulbecco's Modified Eagle's Minimum Essential Medium(DMEM) supplemented with fetal calf serum and an antibiotic is often used.

The culture of transformant may generally be carried out at pH 5.5–8.5 (preferably pH 7–7.5) and 18°–40° C. (preferable 25°–38° C.) for 5–50 hours.

When a bacterium such as $E.\ coli$ is used as a host cell, thus produced new t-PA generally exists in cells of the cultured transformant and the cells are collected by filtration or centrifugation, and cell wall and/or cell membrane thereof are destroyed in a conventional manner (e.g. treatment with super sonic waves and/or lysozyme, etc.) to give debris. From the debris, the new t-PA can be purified and isolated in a conventional manner as generally employed for the purification and isolation of natural or synthetic proteins [e.g. dissolution of protein with an appropriate solvent (e.g. 8M aqueous urea, 6M aqueous guanidium salts, etc.), dialysis, gel filtration, column chromatography, high performance liquid chromatography, etc.]. When the mammalian cell is used as a host cell, the produced new t-PA is generally exist in the culture solution. The culture filtrate (supernatant) is obtained by filtration or centrifugation of the cultured broth. From the culture filtrate, the new t-PA can be purified in a conventional manner as exemplified above.

It may be necessary to obtain the active t-PA from the cell debris of bacteria in the above case. For refolding of thus produced new t-PA, it is preferably employed a dialysis method which comprises, dialyzing a guanidine or urea solution of the new t-PA in the presence of reduced glutathione (GSH) and oxidized glutathione (GSSG) at the same concentration of glutathiones inside and outside of semipermeable membrane at 4°–40° C. for 2–60 hours. In this method, the concentration of the glutathiones is preferably more than 2 mM and the ratio of reduced glutathione and oxidized glutathione is preferably 10:1. Further, the glutathiones can be replaced with cysteine and cystine in this method. These method can be preferably used for refolding of all the t-PA including native t-PA produced by DNA recombinant technology.

The new t-PA of this invention is useful as a thrombolytic agent for the treatment of vascular diseases (e.g. myocardial infarction, stroke, heart attack, pulmonary embolism, deep vein thrombosis, peripheral arterial occlusion, etc.). The new t-PA of this invention in admixture with pharmaceutically acceptable carriers can be parenterally to mammals including human being in a form of a pharmaceutical composition such as infusion.

The pharmaceutically acceptable carriers may include various organic or inorganic carrier materials conventionally employed in the preparation of pharmaceutical composition comprising a peptide or protein (e.g. serum albumin etc.).

A dosage of the new t-PA of this invention is to be varied depending on various factors such as kind of diseases, weight and/or age of a patient, and further the kind of administration route.

The optimal dosage of the new t-PA of this invention is usually selected from a dose range of 0.1–10 mg/kg/day by injection or by infusion.

The total daily amount mentioned above may divisionally be given to the patient for several hours.

Mono(or di, or tri)mer (of oligonucleotides) can be prepared by, for examples the Hirose's method [Cf. Tanpakushitsu Kakusan Kohso 25, 255 (1980)] and coupling can be carried out, for examples on cellulose or polystyrene polymer by a phosphotriester method [Cf. Nucleic Acid Research, 9, 1691 (1981), Nucleic Acid Research 10, 1755 (1982)].

Brief explanation of the accompanying drawings is as follows.

FIG. 1 shows construction and cloning of plasmid pHVBB.

FIG. 2 shows construction and cloning of plasmid pCLiPAxtrp.

FIG. 3 shows DNA sequence of BglII DNA fragment (1974 bp).

FIG. 4 shows construction and cloning of plasmid pCLiPAΔxtrp.

FIG. 5 shows construction and cloning of plasmid pTQiPAΔtrp.

FIG. 6 shows construction and cloning of plasmid pTA9004.

FIG. 7 shows construction and cloning of plamid pTTkPAΔtrp.

FIG. 8 shows DNA sequence of EcoRI DNA fragment (472 bp) and

FIG. 9 shows construction and cloning of pTTiPAΔtrp.

FIG. 10 shows construction and cloning of plasmid pTQkPAΔtrp.

FIG. 12 shows construction and cloning of plasmid pST-Tktrp.

FIG. 14 shows construction and cloning of plasmid pST-Qitrp.

FIG. 15 shows construction and cloning of plasmid pSTQktrp.

FIG. 16 shows construction and cloning of plasmid pMH9006.

FIG. 17 shows construction and cloning of plasmid pthTTtrp.

FIG. 19 shows construction and cloning of plasmid puTTtrp.

FIG. 21 shows cDNA sequence of a native t-PA in pST112.

FIG. 29 shows DNA sequence of coding region in pTTkPAΔtrp.

FIG. 30 shows DNA sequence of coding region in pTTiPAΔtrp.

FIG. 31 shows DNA sequence of coding region in pTQkPAΔtrp.

FIG. 32 shows DNA sequence of coding region in pTQiPAΔtrp.

FIG. 33 shows DNA sequence of coding region in pST-Tktrp.

FIG. 34 shows DNA sequence of coding region in pSTQktrp.

FIG. 35 shows DNA sequence of coding region in pST-Qitrp

FIG. 36 shows DNA sequence of coding region in puTTtrp.

FIG. 37 shows DNA sequence of coding region in pthTTtrp.

FIG. 38 shows DNA sequence of coding region in pmTQk112.

FIG. 39 shows DNA sequence of coding region an pmTTk.

FIG. 40 shows DNA sequence of coding region in pmSTTk.

Figure 11:
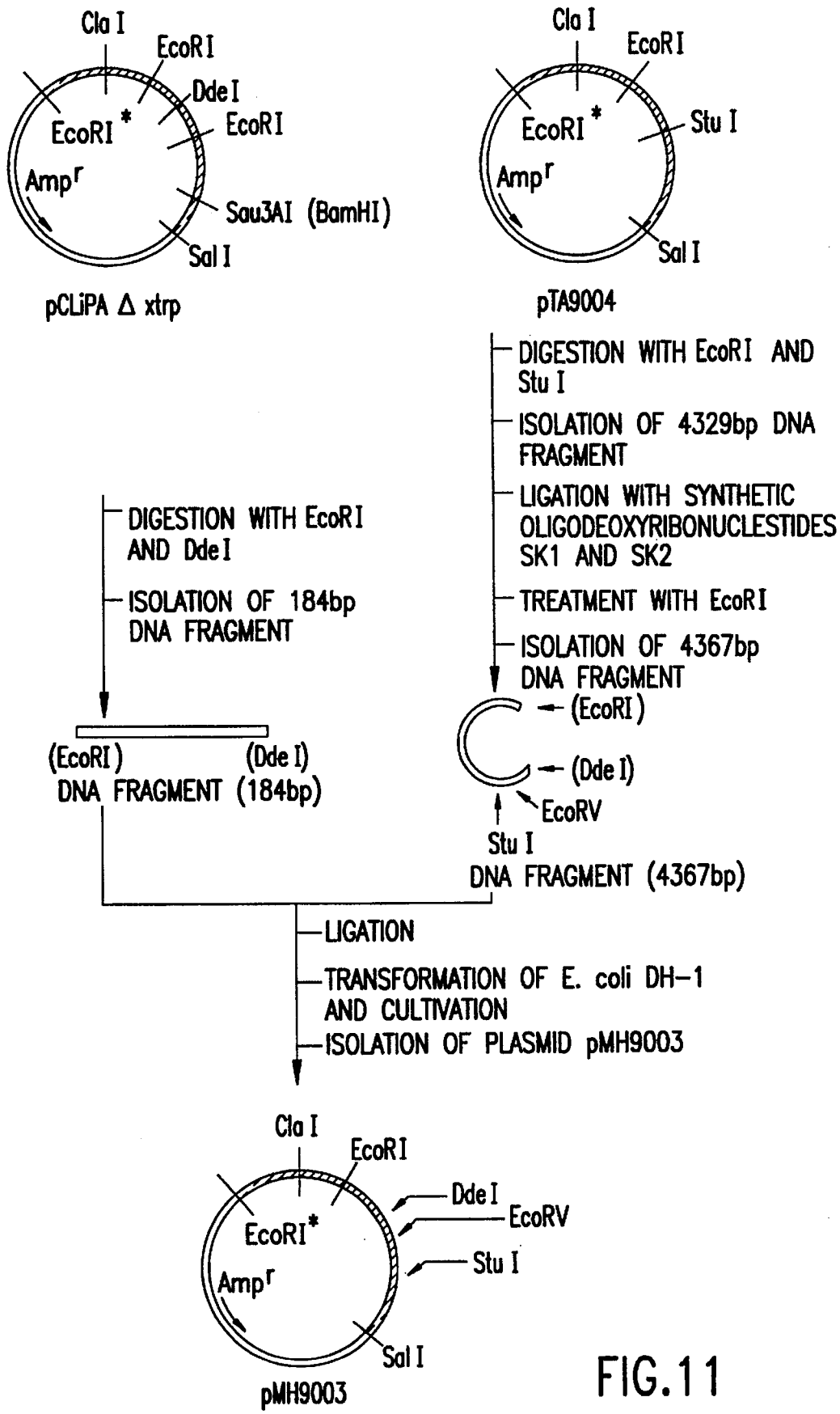
FIG. 11 shows construction and cloning of plasmid pMH9003.

The following Examples are give for the purpose of illustrating this invention, but not limited thereto.

In the Examples, all of the used enzymes (e.g. restriction enzyme, bacterial alkaline phosphatase, T4 DNA ligase) are commercially available and conditions of usage of the enzymes are obvious to the person skilled in the art, for examples, referring to a prescription attached to commercially sold enzymes.

EXAMPLE 1

(Synthesis of oligonucleotides)

The following oligonucleotides were prepared in a conventional manner described as mentioned above.

1) For pHVBB

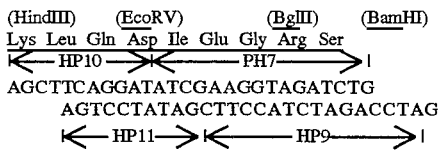

HP10; AG-CTT-CAG-GAT
HP7; ATC-GAA-GGT-AGA-TCT-G
HP11; C-GAT-ATC-CTG-A
HP9; GA-TCC-AGA-TCT-ACC-TT

2) For pTQiPAΔtrp and pTQkPAΔtrp

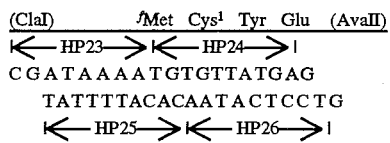

HP23; C-GAT-AAA-AT
HP24; G-TGT-TAT-GAG
P25; ACA-CAT-TTT-AT
HP26; GTC-CTC-ATA

Cys$^1$ of TQitPA or TQktPA is corresponding to Cys$^{92}$ of the native t-PA reported in Nature 301, 214 (1983).

3) For pTTkPAΔtrp and pTTiPAΔtrp

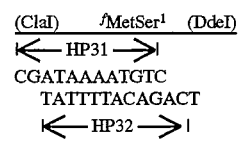

HP31; C-GAT-AAA-ATG-TC
HP32; TC-AGA-CAT-TTT-AT

Ser$^1$ of TTktPA or TTitPA is corresponding to Ser$^{174}$ of the native t-PA reported in Nature 301, 214 (1983).

EXAMPLE 2

(Construction and cloning of plasmid pHVBB)

(as illustrated in FIG. 1)

Oligodeoxyribonucleotides HP7 and HP11 (0.2 nmole of each, see: Example 1-(1)) were phosphorylated in 20 μl of a ligation buffer (1 mM ATP, 50 mM tris-HCl (pH 7.6), 10 mM MgCl$_2$, 20 mM dithiothreitol, 1 mM spermidine, 50 μg/ml bovine serum albumin) with 2.5 units of T4 polynucleotide kinase (Takara Shuzo) at 37° C. for 1 hour. After heat inactivation of the enzyme, other oligodeoxyribonucleotides HP10 and HP9 (0.4 nmole of each), 1 μl of 20 mM ATP and 900 units of T4 DNA ligase (Takara Shuzo) were added to the reaction mixture. The resultant mixture was incubated at 15° C. for 30 minutes to give the crude 27 bp DNA fragment.

On the other hand, pCLaHtrp3t (an experssion vector for α-hANP, the preparation of which is described in European Patent Application Laid open No. 0206769) was digested with BamHI and HindIII. The resulting 4137 bp DNA fragment was isolated by 0.8% agarose gel electrophoresis, and ligated to the crude 27 bp DNA fragment in the presence of T4 DNA ligase. The ligation mixture was used to transform E. coli DH-1 [Cf. Maniatis, T. et al., Molecular cloning p. 505 (1982), Cold Spring Harbor Laboratry (New York)]. From one of the ampicillin resistant transformants, the desired plasmid pHVBB (4164 bp) was isolated and characterized by restriction endonuclease (BglII, EcoRV, PstI, HindIII and BamHI) digestion.

EXAMPLE 3

(Construction and cloning of plasmid pCLiPAxtrp)

(as illustrated in FIG. 2)

pHVBB was digested with BglII. The resulting 4164 linear DNA was incubated with bacterial alkaline phosphatase (Takara Shuzo) in 200 mM Tris-HCl (pH 8.0) at 37° C. for 1 hour to dephosphorylate the both 5' ends of the DNA. The resulting DNA was isolated by 5% polyacrylamide gel electrophoresis (PAGE).

On the other hand, pTPA 102 (Lys$^{277}$→Ile) [an expression vector for a mutant t-PA (Lys$^{277}$→Ile), a transformant comprising the same, E. coli JA 221 (pTPA 102) (Lys$^{277}$→Ile) ATCC 39811] was digested with BglII and the 1974 bp DNA fragment (DNA sequence of which is shown in FIG. 3) was isolated. The fragment was ligated to the 4164 bp BglII DNA fragment in the presence of T4 DNA ligase. After transformation of E. coli MM294 ATCC 33625, an ampicillin resistant transformant carrying the desired plasmid pCLi-PAxtrp (6138 bp), into which the 1974 bp t-PA gene was inserted in a clockwise direction under the down stream of the peptide CLa gene, was obtained. pCLiPAxtrp was characterized by restriction endonuclease (PvuII, EcoRI and BglII) digestion.

EXAMPLE 4

(Construction and cloning of plasmid pCLiPAΔxtrp)

(as illustrated in FIG. 4)

pCLiPAxtrp was digested with BamHI and SacI and the resultant 5388 bp DNA fragment was isolated. On the other hand, pCLiPAxtrp was digested with Sau3AI and SacI. The resultant 389 bp DNA fragment was ligated to the 5388 bp DNA fragment in the presence of T4 DNA ligase. The ligation mixture was used to transform E. coli DH-1. From one of the ampicillin resistant transformants, the desired plasmid pCLiPAΔxtrp (5777 bp) was isolated and was characterized by restriction endonuclease (ClaI, EcoRI, XhoI, NarI and SacI) digestion.

EXAMPLE 5

(Construction and cloning of plasmid pTQiPAΔtrp)

(as illustrated in FIG. 5)

pTPA102 ($Lys^{277} \rightarrow Ile$) as mentioned above was digested with AvaII and BbeI, an isoshizomer of NarI creating 4 nucleotide-long single-stranded cohesive terminal, and the resulting 50 bp DNA fragment encoding $Asp^{95}$-$Ala^{111}$ of the native t-PA was isolated. On the other hand, the synthetic 19 bp ClaI-AvaII DNA fragment was prepared from HP23, HP24, HP25 and HP26 (see: Example 1) using T4 polynucleotide kinase and T4 DNA ligase. It was ligated to the 50 bp DNA fragment with T4 DNA ligase to construct the 69 bp ClaI-BbeI DNA fragment.

pCLiPAΔxtrp was linearlized by BbeI partial digestion. The resultant 5777 bp DNA fragment was digested with ClaI and the 5149 bp DNA fragment was isolated. It was ligated to the 69 bp ClaI-BbeI DNA fragment in the presence of T4 DNA ligase. The ligation mixture was used to transform E. coli DH-1. From one of the ampicillin resistant transformants, the desired plasmid pTQiPAΔtrp (5218 bp) was obtained, which was characterized by restriction endonuclease digestion.

E. coli HB101-16 [HB101 ($recA^+$,$supE^+$,htpR16 (am) $tet^r$) FERM P-9502] was transformed with pTQiPAΔtrp to give a transformant, E. coli HB101-16 (pTQiPAΔtrp).

EXAMPLE 6

(Construction and cloning of plasmid pTA9004)

(as illustrated in FIG. 6)

pCLiPAΔxtrp was digested with DdeI and EcoRI and the 91 bp DNA fragment encoding $Glu^{175}$-$Trp^{204}$ of the native t-PA was isolated. The resultant DNA was ligated to oligodeoxyribonucleotides HP31 and HP32(see: Example 1-(3)) using T4 polynucleotide kinase and T4 DNA ligase. The resultant 103 bp ClaI-EcoRI DNA fragment was ligated to the 4397 bp ClaI-EcoRI fragment of pCLiPAΔxtrp in the presence of T4 DNA ligase. The ligation mixture was used to transform E. coli DH-1. From one of the ampicillin resistant transformants, the desired plasmid pTA9004 (4500 bp) was obtained.

EXAMPLE 7

(Construction and cloning of plasmid FTTkPAΔtrp)

(as illustrated in FIG. 7)

pTA9004 was digested with EcoRI and the resultant DNA fragment (4500 bp) was dephosphorylated with bacterial alkaline phosphatase. On the other hand, pTPA21 which comprises the complete cDNA sequence encoding the native t-PA and a portion of the 3'-noncoding region was digested with EcoRI and the 472 bp DNA fragment encoding $Asn^{205}$-$Lys^{361}$ of the native t-PA (DNA sequence of which is shown in FIG. 8) was isolated. The resultant DNA fragment was ligated to the dephosphorylated 4500 bp EcoRI DNA fragment in the presence of T4 DNA ligase. The ligation mixture was used to transform E. coli DH-1. From one of the ampicillin resistant transformants, the desired plasmid pTTkPAΔtrp (4972 bp) was isolated. E. coli HB 101-16 was transformed with pTTkPAΔtrp to give a transformant E. coli HB101-16 (pTTkPAΔtrp).

EXAMPLE 8

(Construction and cloning of plasmid pTTiPAΔtrp)

(as illustrated in FIG. 9)

pTA9004 was digested with EcoRI and the resultant DNA was dephosphorylated with bacterial alkaline phosphatase. On the other hand, pTPA 102 ($Lys^{277} \rightarrow Ile$) as mentioned above was digested with EcoRI and the 472 bp DNA fragment endoding $Asn^{205}$-$Lys^{361}$ of the mutant t-PA ($Lys^{277} \rightarrow Ile$) was isolated. The resultant DNA fragment was ligated to the dephosphorylated 4500 bp EcoRI DNA fragment in the presence of T4 DNA ligase. The ligation mixture was used to transform E. coli DH-1. From one of the ampicillin resistant transformants, the desired plasmid pTTiPAΔtrp (4972 bp) was isolated. E. coli HB101-16 was transformed with pTTiPAΔtrp to give a transformant E. coli HB 101-16 (pTTiPAΔtrp).

EXAMPLE 9

(Expression and isolation)

A single colony of E. coli HB 101-16 (pTTkPAΔtrp) was inoculated into 5 ml of sterilized LA broth containing bactotrypton 10 g, yeast extract 5 g, NaCl 5 g, 50 µg/ml ampicillin (pH 7.2–7.4) in a test tube and incubated at 37° C. for 8 hours under shaking condition. The cultured broth was added to 100 ml of sterilized fresh LA broth in a flask and incubated at 37° C. for 15 hours under shaking condition. A portion (20 ml) of the resultant broth was added to 400 ml of sterilized M9CA broth containing 25 µg/ml ampicillin, and the mixed broth was incubated at 37° C. When $A_{600}$ of the broth reached approximately 0.6, β-indoleacrylic acid was added to the broth in a final concentration of 10 µg/ml. The resultant broth was incubated at 37° C. for 3 hours, and centrifuged at 4° C., 8, 900×g for 10 minutes The harvested cells were suspended in 100 ml of 10 mM Tris-HCl (pH 8.0) containing 5 mM EDTA, and treated with 50 mg of lysozyme at 4° C. for 1 hour. The resultant mixture was homogenized by a Biotron blender and centrifuged at 4° C., 8, 900×g for 30 minutes. The pellets were washed with 100 ml of 50% aqueous glycerol and dissolved in 800 ml of 10 mM Tris-HCl (pH 8.0) containing 8M urea. To the urea solution, 480 mg of GSH (Kojin) and 96 mg of GSSG (Kojin) were added. The resultant mixture was dialyzed twice against 16 liters of a buffer solution (pH 9.5) containing 20 mM acetic acid, 40 mM ammonia, 2 mM GSH and 0.2 mM GSSG at 4° C. for 15 hours. After centrifuging the mixture, the supernatant was assayed by the following fibrin plate assay. The fibrin plate assay (FPA) was carried out according to the method [Astrup T. and Müllertz S., Arch. Biochem. Biophys. 40 346–351 (1952)] with minor modification. A fibrin plate was prepared by mixing 5 ml of 1.2% human plasminogen-rich fibrinogen (Green-Cross) in 100 mM phosphate buffer (pH 7.2) with 5 ml of thrombin (Mochida, 50 units) in the same buffer, followed by allowing to stand at room temperature for 1 hour. The test solution or human native t-PA (WHO standard) (10 μl of each) were incubated at 37° C. for 18 hours. Using the human native t-PA as the standard, the activities of the samples were calculated from the areas of the lysis zones. From the result of assay, the t-PA activity of the supernatant containing TTkPA was $2.3\times10^5$ IU of the native t-PA/l.

EXAMPLE 10

(Expression and isolation)

A single colony of E. coli HB 101-16 (pTTiPAΔtrp) was cultured and TTitPA was isolated from the resultant culltured broth in the substantially the same manner as that described in Example 9. The t-PA activity of the resultant supernatant containing TTitPA was $2.0\times10^4$ IU of the native t-PA/l.

EXAMPLE 11

(Expression and isolation)

A single colony of E. coli HB 101-16 (pTQiPAΔtrp) was cultured and TQitPA was isolated from the resultant cull- tured broth in the substantially the same manner as that described in Example 9. The t-PA activity of the resultant supernatant containing TQitPA was $2.0\times10^4$ IU of the native t-PA/l.

EXAMPLE 12

(Purification of TTktPA)

All procedures were performed in cold room (at 4°–6° C.). The plasminogen activator, TTktPA in the supernatant renatured was isolated and purified as follows:

In the first step, the supernatant prepared from 20 liter of the cultured broth obtained in a similar manner to that described in Example 9 [TTktPA total activity: $3.4\times10^6$ IU of the native t-PA (WHO)] was loaded onto benzamidine Sepharose column [1.6 cm×3 cm: p-aminobenzamidine was linked covalently to CH Sepharose 4B (Pharmacia) by the carbodiimide method described in the literature: Las Holmberg, et al., BBA, 445, 215–222 (1976)] equilibrated with 0.05M Tris-HCl (pH 8.0) containing 1M NaCl and 0.01% (v/v) Tween80 and then washed with the same buffer. The plasminogen activator was eluted with 0.05M Tris-HCl (pH 8.0) containing 1M arginine and 0.01% (v/v) Tween80.

In the next step, pooled active fractions were applied on IgG coupled Sepharose (FTP 1163) column (1.6 cm×3 cm) [monoclonal anti t-PA antibody: FTP 1163 (Tsutomu Kaizu et al., Thrombosis Research, 40, 91–99 (1985) was coupled to CNBr activated Sepharose 4B according to manufacture's instructions] equilibrated with 0.1M Tris-HCl (pH 8.0). The column was washed with 0.1M Tris-HCl (pH 8.0) containing 1M NaCl, 0.01% (v/v) Tween80 and Aprotinin (10 KIU/ml, Sigma). Elution was done with 0.1M glycine-HCl (pH 2.5) containing 0.5M NaCl, 0.01% Tween80 and Aprotinin (10 KIU/ml).

In the last step, pooled active fractions obtained from the IgG Sepharose (FTP1163) column were dialyzed against 1 liter of 0.01M phosphate buffer (pH 7.4) containing 1.6M KSCN and 0.01% (v/v) Tween80. The solution dialyzed was concentrated to about 2 ml by dialysis against solid poly- ethylene glycol 20,000. The concentrate obtained was gel- filtered on a Sephacryl S200HR (Pharmacia, 1.6 cm×90 cm) in 0.01M phosphate buffer (pH 7.4) containing 1.6M KSCN and 0.01% (v/v) Tween80. The pooled active fractions were concentrated to about 10 ml by dialysis against solid poly- ethylene glycol 20,000 and the concentrate was then dia- lyzed against 0.1M ammonium bicarbonate containing 0.15 M NaCl and 0.01% (v/v) Tween80 to give dialyzate con- taining purified TTktPA (3.4 mg, $7.35\times10^5$ IU of the native t-PA (WHO)/mg·protein).

The TTktPA purified have following characteristics.

(i) Analytical SDS PAGE

A 15% polyacrylamide gel was prepared according to the method of Laemmli (U.K. Laemmli, Nature (London 227, 680–685 (1970)). The gel was stained with silver (H. M. Poehling, et al., Electrophoresis, 2, 141 (1981)).

TTktPA thus purified migrate on the SDS-PAGE as a single band at 35K Daltons under reducing condition and 32K Daltons under nonreducing condition, whereas material incubated with plasmin Sepharose (Per Wallin, et al., BBA, 719, 318–328 (1982)) yielded two bands at 30K Daltons (protease domain) and 13.5K Daltons (kringle domain) in the presence of reducing agent, and only one band at 32K Daltons in the absence of reducing agent.

(ii) HPLC

TTktPA purified was applied to a (4.6 mm×75 mm) ultrapore RPSC column (Beckman, U.S.A.). Elution was performed with a linear gradient of acetonitrile (10–60% (v/v)) in 0.1% (v/v) trifluoroacetic acid at a flow rate of 1.0 ml/min over 30 minutes.

In this system, TTktPA was eluted as single major species at an acetonitrile concentration of approximately 36.5% (v/v).

(iii) N-terminal sequence analysis

Purified single chain TTktPA was reduced and carboxymethylated, desalted on HPLC (Ultrapore RPSC column, concentrated by Speed Vac Concentrator (Savant) and analyzed using a gas phase sequencer, model 370A (Applied Biosystem). The N-terminal amino acid sequence of thus obtained TTktPA was as follows.

SerGluGlyAsn -

EXAMPLE 13

(Construction and cloning of plasmid pTQkPAΔtrp)

(as illustrated in FIG. 10)

The plasmid pTQiPAΔtrp was digested with EcoRI. The reaction mixture was dephosphorylated with bacterial alka- line phosphatase and the resultant 4744 bp DNA fragment was isolated. On the other hand, the plasmid pTPA 21 was digested with EcoRI and the resultant 472 bp DNA fragment was isolated. The 472 bp DNA fragment was ligated to the 4744bp DNA fragment in the presence of T4 DNA ligase and the ligation mixture was used to transform E. coli DH-1. From one of the transformants resistant to ampicillin, the desired plasmid pTQkPAΔtrp was isolated and characterized by restriction mapping. E. coli HB101-16 was transformed with the plasmid pTQkPAΔtrp to give a transformant E. coli HB101-16 (pTQkPAΔtrp).

EXAMPLE 14

(Synthesis of oligonucleotides)

The following oligonucleatides were prepared in a con- ventional manner described as mentioned above.

1) Linkage sequence for pSTTktrp and pSTQktrp

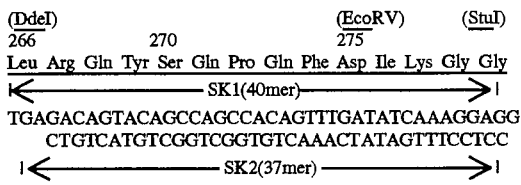

2) Linkage sequence for pSTQitrp

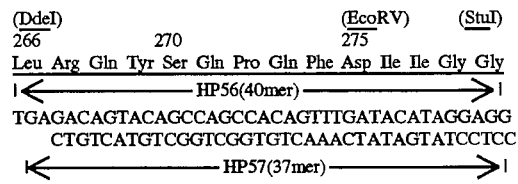

3) Linkage sequence for pthTTtrp

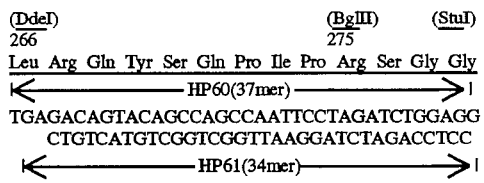

4) Linkage sequence for puTTtrp

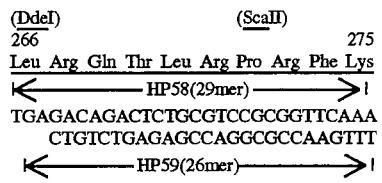

Numbers above the amino acids refer to the positions of the native t-PA reported by Pennica et al (Nature 301, 214–221, 1983).

EXAMPLE 15

(Construction and cloning of plasmid pMH9003)

(as illustrated FIG. 11).

The plasmid pTA9004 was digested with EcoRI and StuI, and the resultant 4329 bp DNA fragment was isolated. The DNA fragment was ligated to the synthetic oligodeoxyribonucleotides SK1 and SK2 using T4 polynucleotide kinase and T4 DNA ligase. The reaction mixture was treated with EcoRI to reconstruct the cohesive end digested with EcoRI, and the resultant EcoRI-DdeI DNA fragment (4367 bp) was ligated to the 184 bp EcoRI-DdeI DNA fragment coding $Asn^{205}$-$Leu^{266}$ of the native t-PA which was obtained from the plasmid pCLiPAΔxtrp in the presence of T4 DNA ligase. The ligation mixture was used to transform E. coli DH-1. From one of the transformants resistant to ampicillin, the desired plasmid pMH9003 was isolated and characterized by restriction endonuclease digestion.

EXAMPLE 16

(Construction and cloning of plasmid pSTTktrp)

(as illustrated in FIG. 12)

The plasmid pMH9003 was digested with StuI and the resulting DNA fragment (4551 bp) was dephosphorylated with calf intestinal phosphatase (Pharmacia AB). On the other hand, the plasmid pCLiPAΔxtrp was digested with StuI and the resultant 419 bp DNA fragment coding for $Gly^{279}$-$Ala^{419}$ of the native t-PA was isolated. The resultant DNA fragment was ligated to the 4551 bp StuI DNA fragment in the presence of T4 DNA ligase. The ligation mixture was used to transform E. coli DH-1. From one of the transformants resistant to ampicillin, the desired plasmid pSTTktrp was isolated and characterized by restriction endonuclease digestion. E. coli HB101-16 was transformed with the plasmid pSTTktrp to give a transformant, E. coli HB101-16 (pSTTktrp).

EXAMPLE 17

(Construction and cloning of plasmid pZY)

Figure 13:
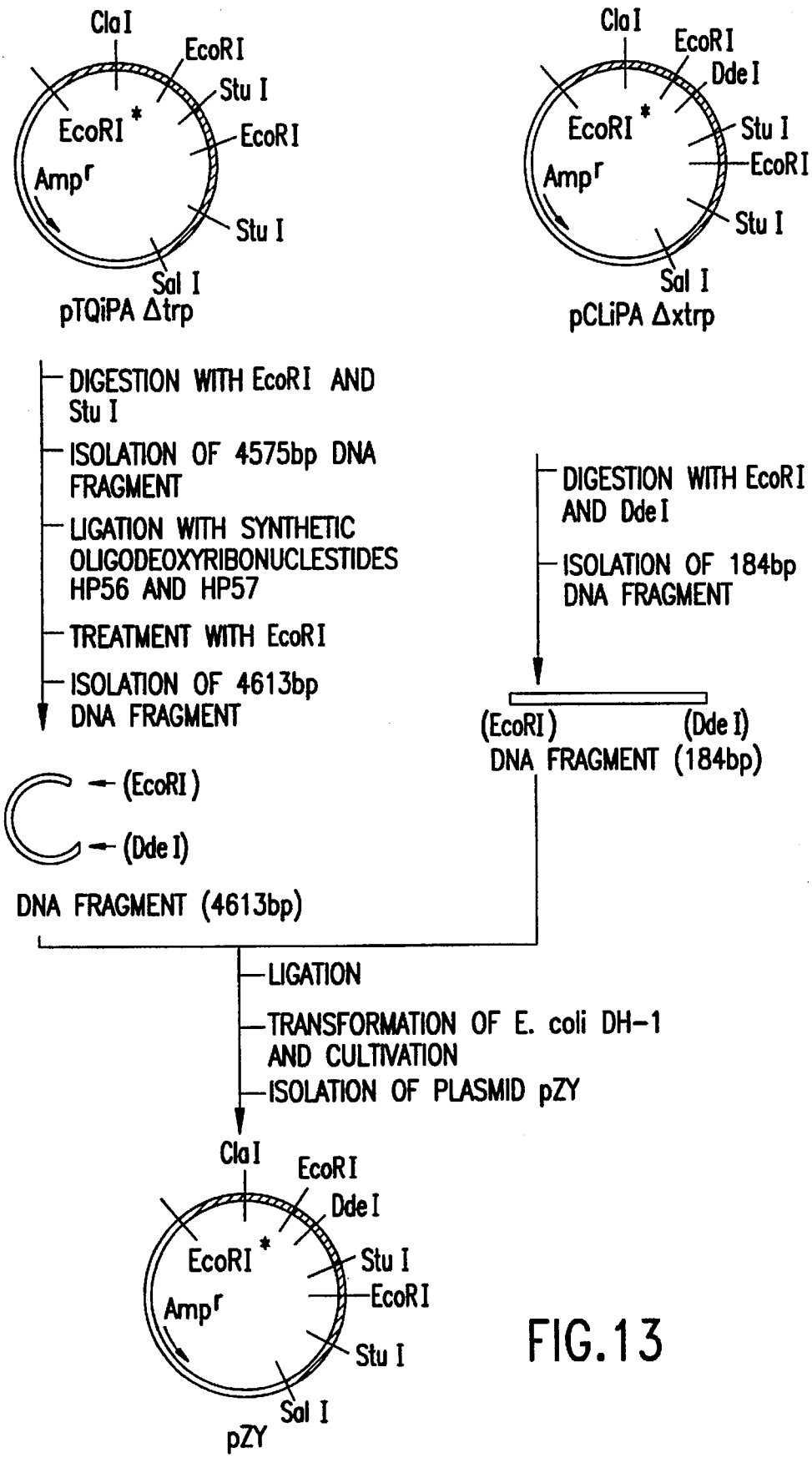
FIG. 13 shows construction and cloning of plasmid pZY.

(as illustrated in FIG. 13)

The plasmid pTQiPAΔtrp was digested with EcoRI and StuI, and the resultant 4575 bp DNA fragment was isolated. The DNA fragment was ligated to the synthetic oligodeoxyribonucleotides HP56 and HP57 using T4 polynucleotide kinase and T4 DNA ligase. The reaction mixture was treated with EcoRI to reconstruct the cohesive end digested with EcoRI, and the resultant EcoRI-DdeI DNA fragment (4613 bp) was ligated to the 184 bp EcoRI-DdeI DNA coding for $Asn^{205}$-$Leu^{266}$ of the native t-PA which was prepared from the plasmid pCLiPAΔxtrp in the presence of T4 DNA ligase.

The ligation mixture was used to transform E. coli DH-1. From one of the transformants resistant to ampicillin, the desired plasmid pZY was isolated and characterized by restriction mapping.

EXAMPLE 18

(Construction and cloning of plasmid pSTQitrp)

(as shown in FIG. 14)

The plasmid pZY was digested with StuI and the resulting DNA fragment (4797 bp) was dephosphorylated with calf intestinal phosphatase. On the other hand, the plasmid pCLiPAΔxtrp was digested with StuI and the resultant 419 bp DNA fragment coding for $Gly^{279}$-$Ala^{419}$ of the native t-PA was isolated. The 419 DNA fragment was ligated to the 4797 bp DNA fragment in the presence of T4 DNA ligase. The ligation mixture was used to transform E. coli DH-1. From one of the transformants resistant to ampicillin, the desired plasmid pSTQitrp was isolated and characterized by restriction mapping. E. coli HB101-16 was transformed with the plasmid pSTQitrp to give a transformant E. coli HB101-16 (pSTQitrp).

EXAMPLE 19

(Construction and cloning of plasmid pSTQktrp)

(as illustrated in FIG. 15)

The plasmid pSTTktrp was digested with ClaI and EcoRV and the resultant 4656 bp DNA fragment was isolated. On the other hand, the plasmid pSTQitrp was digested with ClaI and EcoRV, and the 560 bp DNA fragment coding for $Cys^1$-$Asp^{184}$ of STQitPA was isolated. The resulting DNA fragment was ligated to the 4656 bp DNA fragment in the presence of T4 DNA ligase. The ligation mixture was used to transform E. coli DH-1.

From one of the transformants resistant to ampicillin, the desired plasmid pSTQktrp was isolated and characterized by restriction mapping. E. coli HB101-16 was transformed with pSTQktrp to give a transformant HB101-16 (pSTQktrp).

EXAMPLE 20

(Construction and cloning of plasmid pMH9006)

(as illustrated in FIG. 16)

The plasmid pTA9004 was digested with StuI and EcoRI, and the resultant 4329 bp DNA fragment was isolated. The DNA fragment was ligated to synthetic oligodeoxyribonucleotides HP60 and HP61 using T4 polynucleotide kinase and T4 DNA ligase. The ligation mixture was digested with EcoRI to regenerate the cohesive end digested with EcoRI, and the resultant EcoRI-DdeI DNA fragment (4364 bp) was ligated to the 184 bp EcoRI-DdeI DNA fragment coding for $Asn^{205}$-$Leu^{266}$ of the native t-PA which was prepared from the plasmid pCLiPAΔxtrp. The ligation mixture was-used to transform E. coli DH-1. From one of the transformants resistant to ampicillin, the desired plasmid pMH9006 was isolated and characterized by restriction mapping.

EXAMPLE 21

(Construction and cloning of pthTTtrp)

(as illustrated in FIG. 17)

The plasmid pME9006 was digested with StuI and the resultant linearized DNA fragment (4548 bp) was dephosphorylated with calf intestinal phosphatase. On the other hand, the plasmid pCLiPAΔxtrp was digested with StuI and the 419 bp DNA fragment encoding $Gly^{279}$-$Ala^{419}$ of the native t-PA was isolated. The resultant DNA fragment was ligated to the 4548 bp DNA fragment in the presence of T4 DNA ligase. The ligation mixture was used to transform E. coli DH-1.

From one of the transformants resistant to ampicillin, the desired plasmid pthTTtrp was isolated and characterized by restriction mapping. E. coli HB101-16 was transformed with the plasmid pthTTtrp to give an transformant E. coli HB101-16 (pthTTtrp)

EXAMPLE 22

(Construction and cloning of plasmid pMH9007)

Figure 18:
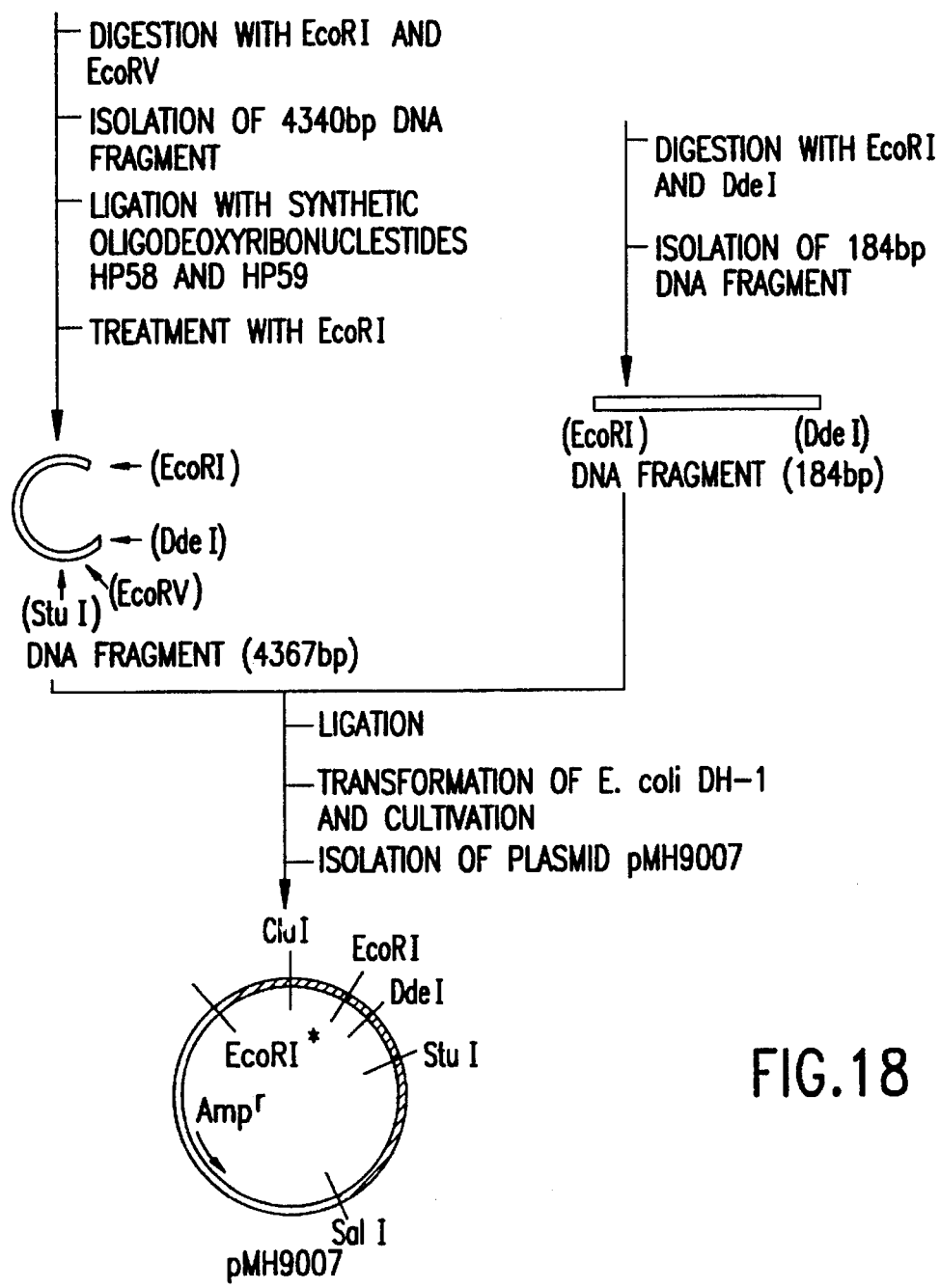
FIG. 18 shows construction and cloning of plasmid pMH9007.

(as illustrated in FIG. 18)

The plasmid pMH9003 was digested with EcoRI and EcoRV, and the 4340 bp DNA fragment was isolated. The resultant DNA fragment was ligated to the synthetic oligodeoxyribonucleotides HP58 and HP59 by using T4 polynucleotide kinase and T4 DNA ligase. The ligation mixture was treated with EcoRI to regenerate the cohesive terminal digested with EcoRI.

The resultant DNA fragment (4367 bp) was ligated to the 184 bp EcoRI-DdeI DNA fragment obtained from the plasmid pCLiPAΔxtrp in the presence of T4DNA ligase. The ligation mixture was used to transform E. coli DH-1.

From one of the transformants resistant to ampicillin, the desired plasmid pMH9007 was isolated and characterized by restriction mapping.

EXAMPLE 23

(Construction and cloning of plasmid puTTtrp)

(as illustrated in FIG. 19)

The plasmid pMH9007 was digested with StuI and the resultant linearized DNA fragment (4551 bp) was dephosphorylated with calf intestinal phosphatase. On the other hand, the plasmid pCLiPAΔxtrp was digested with StuI and the resultant 419 bp DNA fragment was isolated. The 419 bp DNA fragment was ligated with the 4551 bp DNA fragment in the presence of T4 DNA ligase. The ligation mixture was used to transform E. coli DH-1.

From one of the transformants resistance to ampicillin the desired plasmid puTTtrp was isolated and characterized by restriction mapping. E. coli HB101-16 was transformed with the plasmid puTTtrp to give a transformant E. coli HB101-16 (puTTtrp).

EXAMPLE 24

(Expression and isolation)

E. coli HB101-16 (pTQkPAΔtrp) was cultured and TQk-tPA was isolated from the resultant cultured broth in substantially the same manner as described in Example 9. The t-PA activity of the resultant supernatant containing TQktPA was $7.7 \times 10^4$ IU of the native t-PA/l.

EXAMPLE 25

(Expression and isolation)

E. coli HB101-16 (pSTTktrp), E. coli HB101-16 (pSTQktrp), E. coli HB101-16 (pSTQitrp), E. coli HB101-16 (pthTTtrp) and E. coli HB101-16 (puTTtrp) were used for the expression of new t-PAs. Cultivation of the bacteria was carried out in substantially the same manner as that described in Example 9. The cell pellets obtained from the resultant cultured broth (200 ml) were suspended in 20 ml of 10 mM phosphate buffered saline (pH 8.0) and sonicated at 4° C. for 1 minute. After centrifugation at 15,000 rpm for 20 minutes at 4° C., the resultant pellets were suspended in 20 ml of Triton X-100 solution (0.5% Triton X-100, 8% sucrose, 50 mM EDTA, 10 mM Tris; HCl, pH 8.0) and sonicated at 4° C. for 1 minute. The suspension was centrifuged at 15,000 rpm for 20 minute. The resultant pellets were washed with 20 ml of 50% aqueous glycerol and 20 ml of ice-cold ethanol, successively, and dissolved in 20 ml of 8M urea solution containing 8M urea, 20 mM acetic acid, 40 mM ammonium hydroxide, 0.4 mM cysteine and 0.04 mM cystine, pH9.5) by sonication.

After centrifugation at 15,000 rpm for 20 minutes, the supernatant was diluted to A280=0.1 (absorbance at 280 nm) with the 8M urea solution. The resultant solution was dialysed against 10 times volume of aqueous solution containing 20 mM acetic acid, 40 mM ammonium hydroxide, 0.4 mM cysteine and 0.04 mM cystine (pH 9.5) at room temperature for 15 hours. In the above procedure, each of the dialysates containing the new t-PAs, STTktPA, STQktPA, STQitPA, thTTtPA or uTTtPA was obatined from the cultured broth of E. coli HB101-16 (pSTTktrp), E. coli HB101-16 (pSTQktrp), E. coli HB101-16 (pSTQitrp), E. coli HB101-16 (pthTTtrp) or E. coli HB 101-16(puTTtrp), respectively. Each of the resultant dialysates was subjected to the fibrin plate assay as described in Example 9, respectively. The results are shown in the following table.

| New t-PA contained in the dialysate | Activity (IU of the native t-PA/l) |
| --- | --- |
| STTktPA | $1.1 \times 10^5$ |
| STQktPA | $2.3 \times 10^4$ |
| STQitPA | $2.3 \times 10^4$ |
| thTTtPA | $3.7 \times 10^4$ |
| uTTtPA | not detected*) |

*)uTTtPA may be a proenzyme like pro-urokinase. Although it was inactive by fibrin plate assay, it was produced in a ratio of 29 μg/l of the cultured broth as analysed by enzyme immunoassay.

EXAMPLE 26

(Determination of molecular weights of new tPAs)

Molecular weights of the new t-PAs as produced in the above Examples were determined by SDS-PAGE analysis using marker proteins(94,000, 67,000, 45,000, 30,000, 14,400 daltons). The results are shown in the following table.

Molecular weights of the new t-PAs as produced in the above Examples were determined by SDS-PAGE analysis using markerproteins(94,000, 67,000, 45,000, 30,000, 14,400 daltons). The results are shown in the following table.

| The new t-PAs | molecular weight (dalton) |
| --- | --- |
| TTktPA | approximately 38,000 |
| TTitPA | approximately 38,000 |
| TQitPA | approximately 45,000 |
| TQktPA | approximately 45,000 |
| STTktPA | approximately 38,000 |
| STQktPA | approximately 45,000 |
| STQitPA | approximately 45,000 |
| thTTtPA | approximately 38,000 |
| uTTtPA | approximately 38,000 |

EXAMPLE 27

(Identification of DNA sequence)

Expression vectors were characterized and identified by restriction mapping followed by partial DNA sequencing by the dideoxyribonucleotide chain termination method [Smith, A. J. H. Meth. Enzym. 65, 560–580 (1980)] applied to double strand DNA.

The plasmid pTTkPAΔtrp (2 μg in 16 μl of 10 mM Tris·HCl (pH 7.4)-1 mM EDTA) was treated with 2 mM EDTA (2 μl) and 2N NaOH (2 μl) at room temperature for 5 minutes. To the resultant mixture, 5M ammonium acetate (8 μl) and EtOH (100 μl) was added. The mixture was cooled at −80° C. for 30 minutes and centrifuged at 12,000 rpm for 5 minutes. After discarding the supernatant, precipitates were washed with ice-cold 70% aqueous EtOH and dried in vacuo to give the denatured plasmid.

The plasmid was annealed with a synthetic oligodeoxyribonucleotide primer (5'-ATATTCTGAAATGAGCTGT, corresponding to −55—37th position of the tryptophan promoter, 5 ng) in 40 mM Tris·HCl (pH 7.5)–20 mM MgCl$_2$–50 mM NaCl at 65° C. for 15 minutes followed by gently cooling to room temperature in 30 minutes. The sequencing reaction was performed with T7 polymerase (Sequenase, United States Biochemical Corp) and -$^{35}$S-dATP (Amersham) according to Tabor, S and Richardson, C. C., Proc. Natl. Acad. Sci. U.S.A. 84, 4767–4771 (1987). The determined sequence (approximately 150 bases from the primer i.e. 35 bases in the tryptophan promoter and 115 bases in the N-terminal coding sequence of TTktPA) was identical with that as expected.

The DNA sequence of pTQkPAΔtrp was performed in a similar manner as described above.

The DNA sequences of pSTTkPAtrp, pthTTtrp and puTTtrp were performed in a similar manner as above except for using a synthetic oligodeoxyribonucleotide (5'-CTCCGGGCGACCTCCTGTG, complementary to the DNA sequence for His$^{297}$-Gly$^{302}$ of native tPA).

EXAMPLE 28

(Identification of amino acid sequence)

Purified STTktPA which was purified from the dialysate comprising STTktPA obtained in Example 25 by the similar purification method described in Example 12, was dissolved in 8M urea–50 mM Tris·HCl (pH 8.0)–1.5% β-mercaptoethanol, and treated with monoiodoacetic acid for carboxymethylation of SH group in Cys residues. The resultant carboxymethylated STTktPA was purified by preparative HPLC using COSMOSIL 5C$_4$-300 (4.6 mmϕ×50 mm, Nakarai Tesque), and sequenced by a gas-phase sequencer 470A (Applied Biosystems Inc). The N-terminal sequence of the sample was Ser-Glu-Gly-Asn-Ser-Asp-Cys-Tyr-Phe-Gly-Asn-Gly-Ser-Ala-Tyr which was identical with the sequence as expected.

EXAMPLE 29

(Construction and cloning of pST118)

Figure 20:
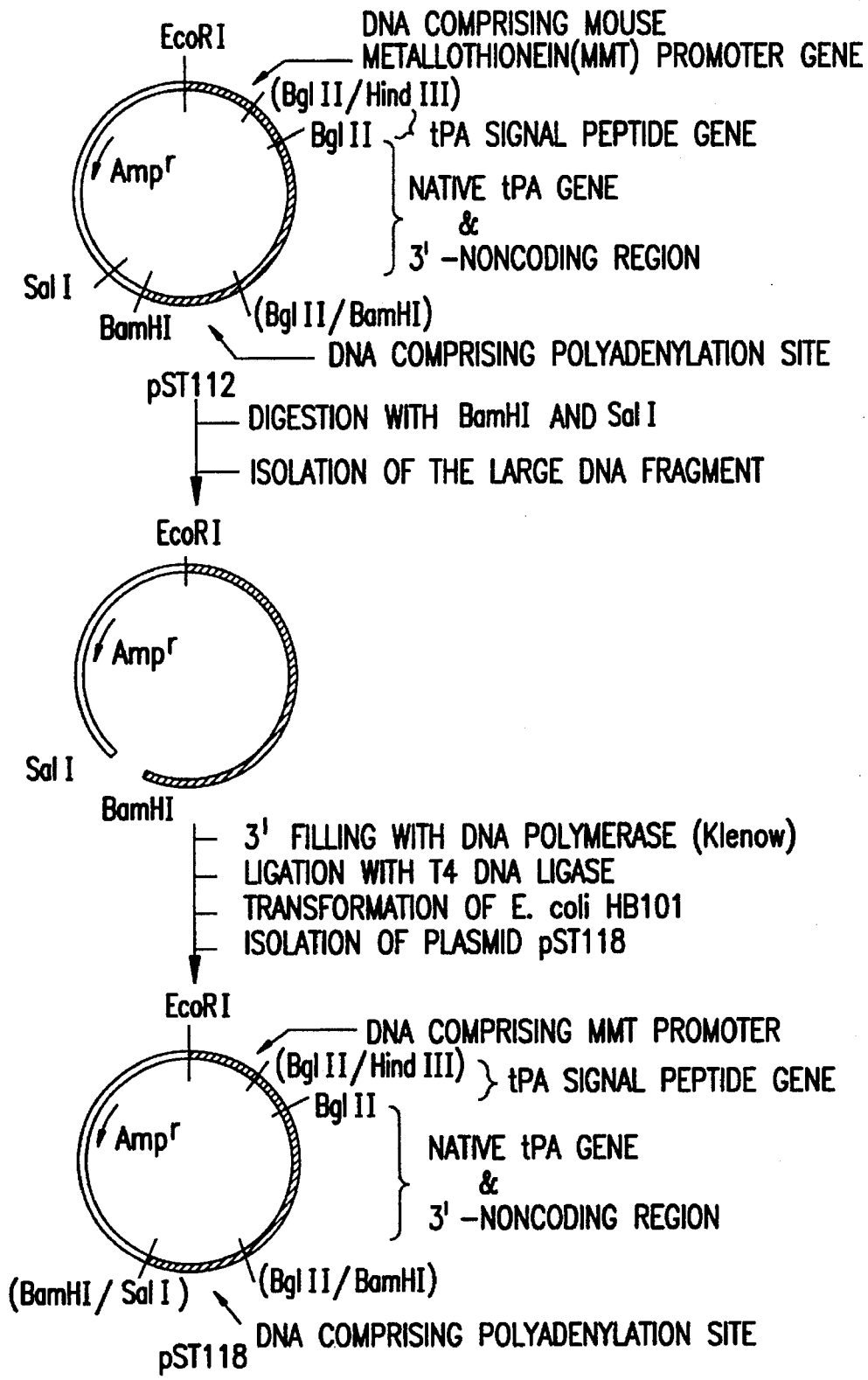
FIG. 20 shows construction and cloning of plasmid pST118.

(as illustrated in FIG. 20)

The plasmid pST112 [an expression vector for a native t-PA which can be isolated from a transformant comprising the same, E. coli DH-1 FERM BP-1966, the complete cDNA sequence of a native t-PA in pST 112 is illustrated in FIG. 21] was digested with BamHI and SalI.

The large DNA was isolated and blunted with DNA polymerase I (Klenow fragment). The resultant DNA fragment was self-ligated with T4 DNA ligase. The ligation mixture was used to transform E. coli HB101. From one of ampicillin resistant transformants, the objective plasmid pST118 was obtained and characterized by restriction mapping.

EXAMPLE 30

(Construction and cloning of pmTQk112)

Figure 22:
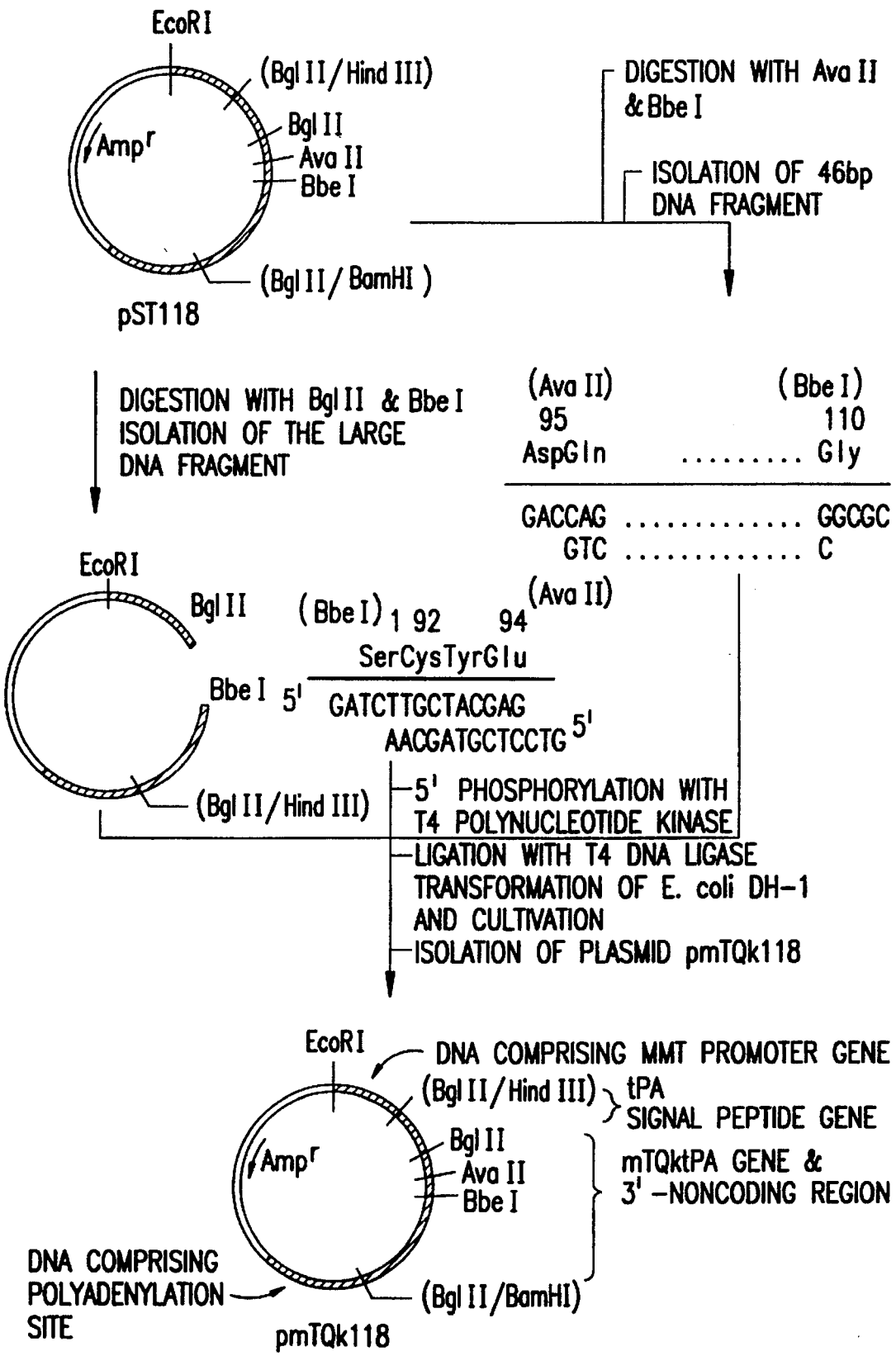
FIG. 22 shows construction and cloning of plasmid pmTQkl118
Figure 23:
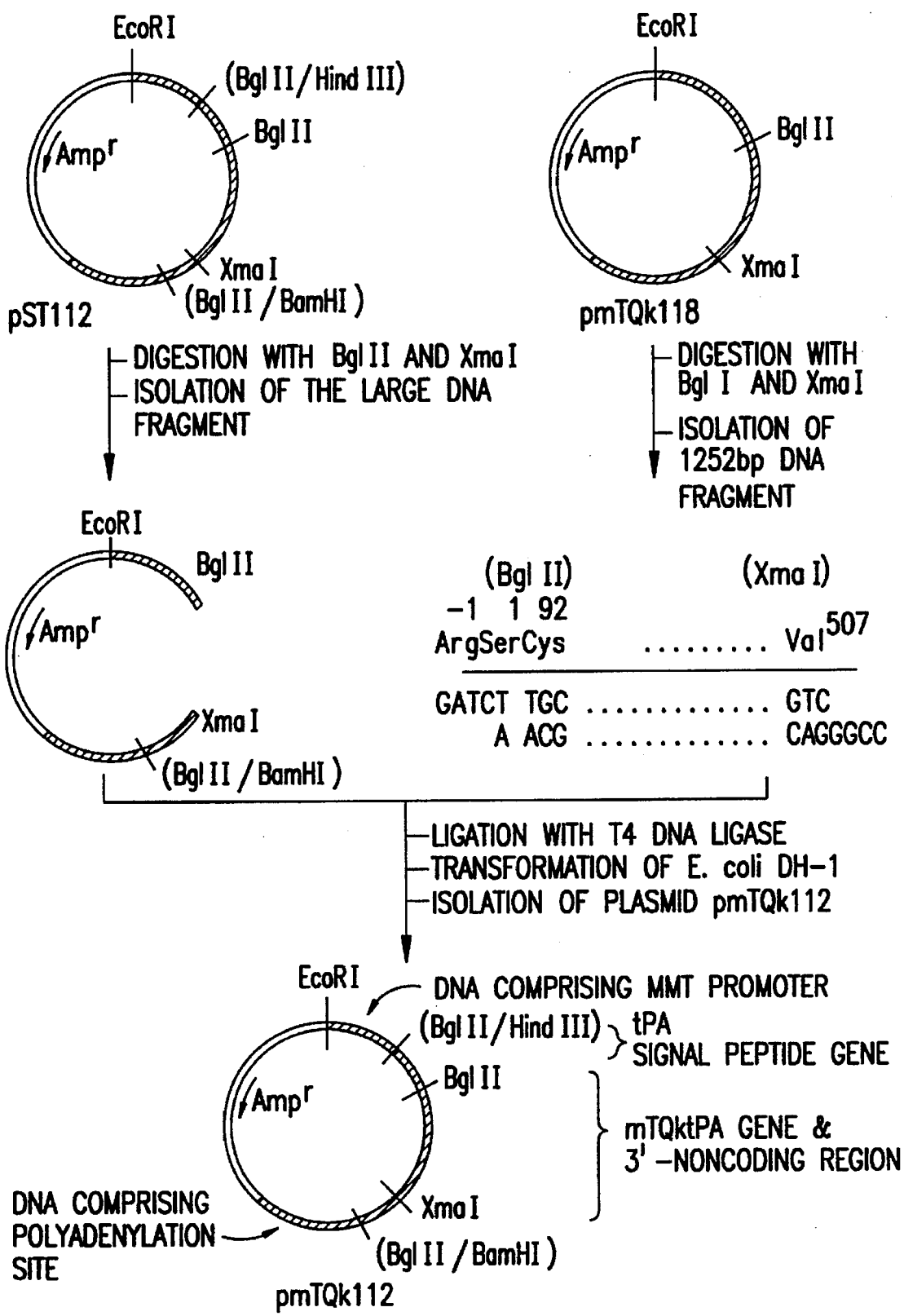
FIG. 23 shows construction and cloning of plasmid pmTQkl112.

(as illustrated in FIGS. 22 and 23)

The plasmid pST118 was digested with BglII and BbeI. The large DNA fragment was isolated and ligated to synthetic BglII-AvaII DNAs (5'-GATCTTGCTACGAG and 5'-GTCCTCGTAGCAA, each oligomer was phosphorylated with T4 polynucleatide kinase (Takara Suzo)) coding for Arg$^{-1}$ Ser$^1$ Cys$^{92}$ Tyr Glu, and Ava II-BbeI DNA coding for Asp$^{95}$-Gly$^{110}$ of the native tPA from pST118 with T4 DNA ligase (Takara Suzo).

The ligation mixture was used to transform E. coli DH-1. From one of the ampicillin resistant transformants, the objective plasmid pmTQk118 was isolated and characterized by restriction mapping.

On the other hand, the plasmid pST112 was digested with BglII and XmaI. The large DNA fragment was isolated and ligated to 1253 bp BglII-XmaI DNA coding for Arg$^{-1}$-Val$^{507}$ from pmTQk118 with T4 DNA ligase to give pmTQk112, an expression vector for mTQktPA in mammalian cell.

EXAMPLE 31

(Construction and cloning of pmTTk)

Figure 24:
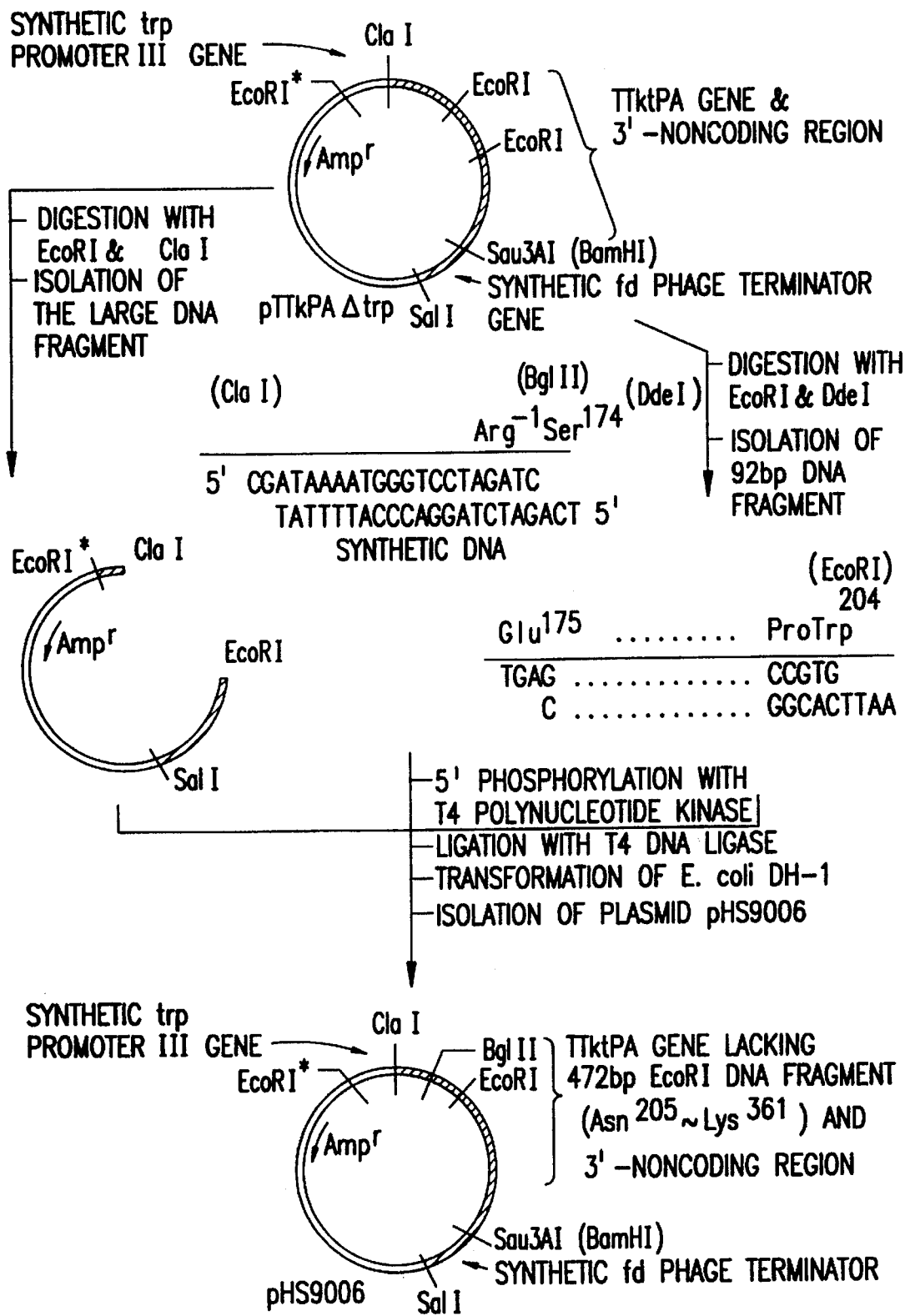
FIG. 24 shows construction and cloning of plasmid pHS9006.
Figure 25:
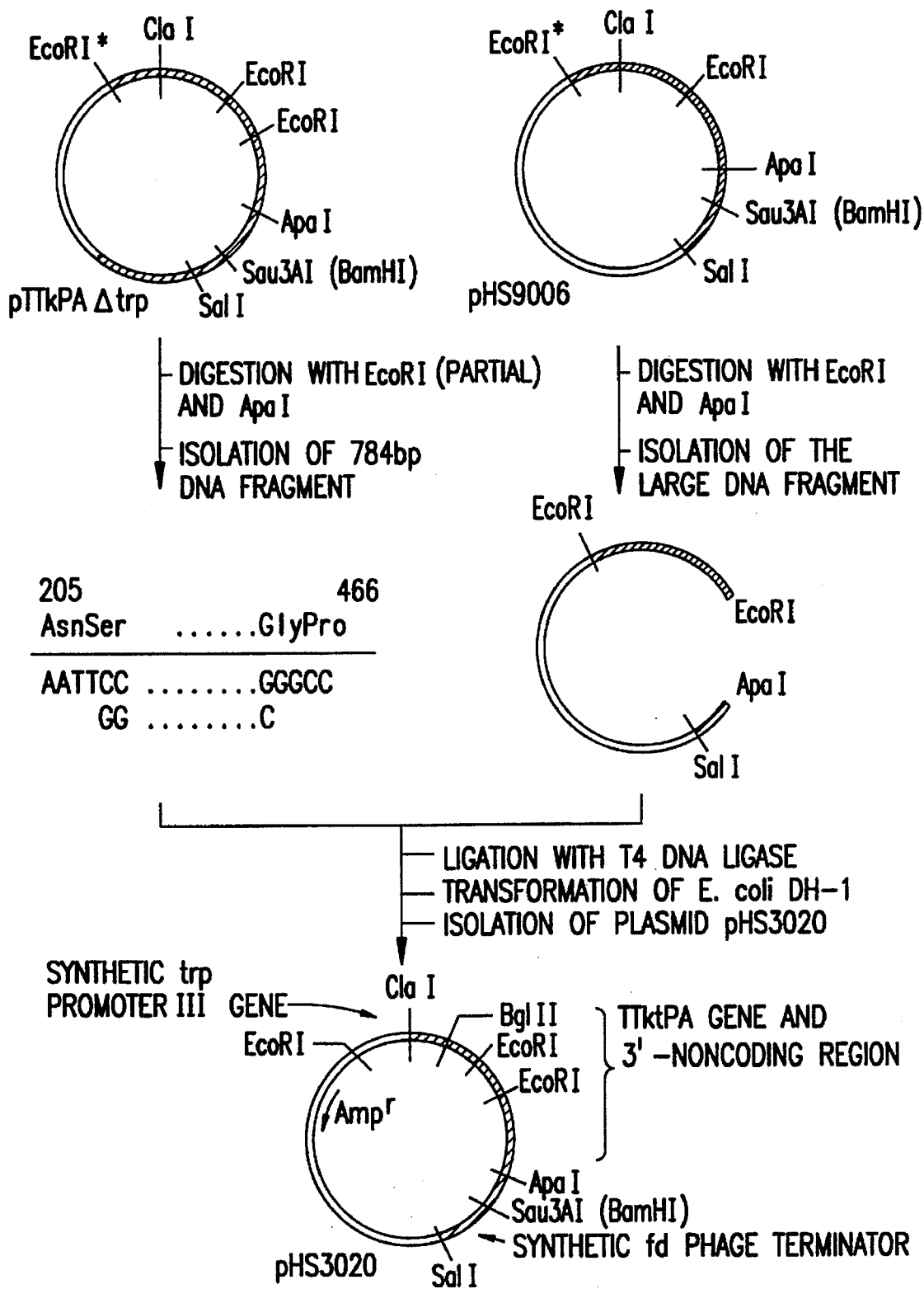
FIG. 25 shows construction and cloning of plasmid pHS3020.
Figure 26:
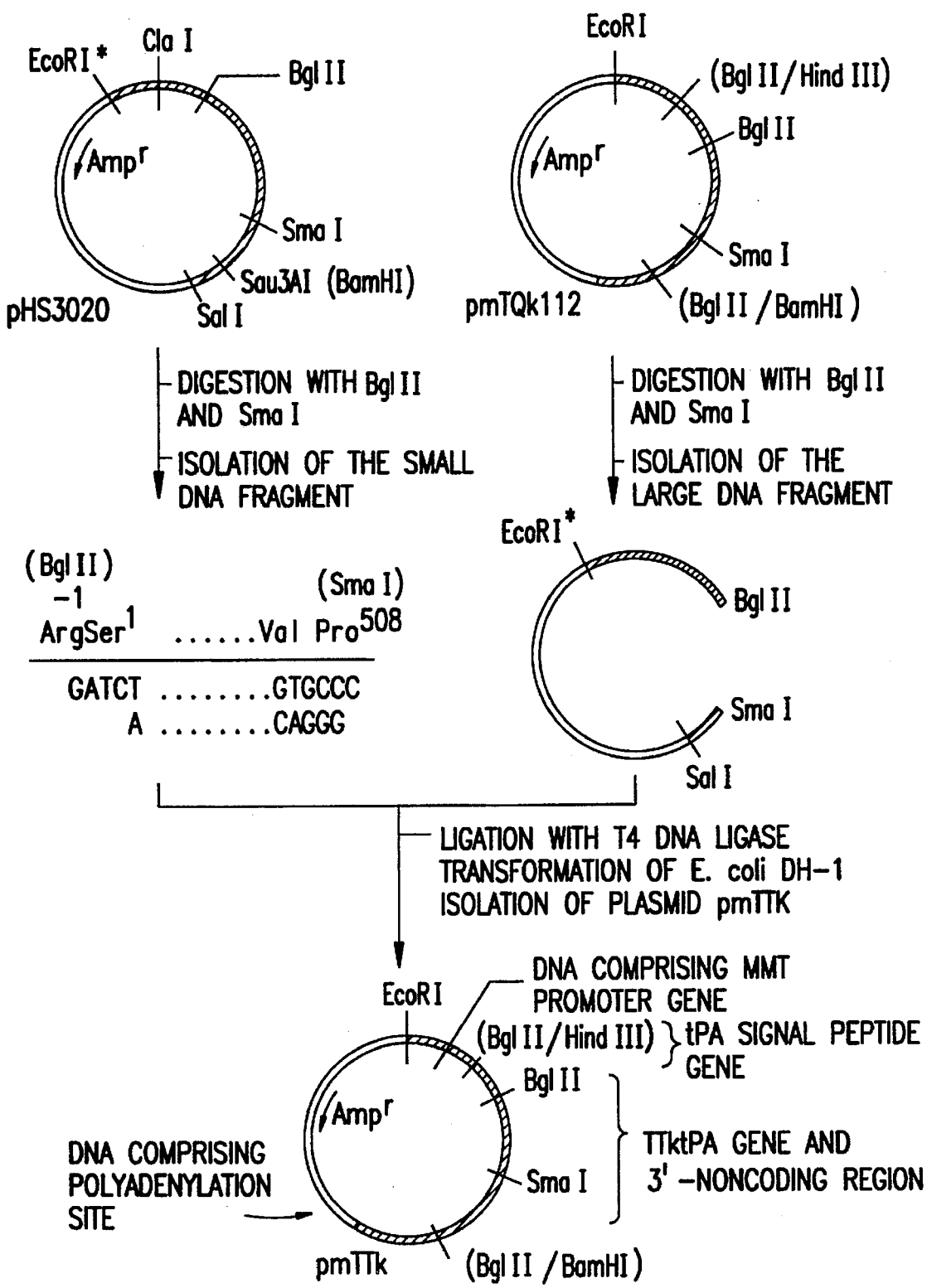
FIG. 26 shows construction and cloning of plasmid pmTTk.

(as illustrated in FIGS. 24, 25 and 26)

pTTkPAΔtrp was digested with ClaI and EcoRI completely. The large DNA fragment was isolated and ligated to ClaI-DdeI synthetic DNAs (5'-CGATAAAATGGGTCCTAGATC and 5'-TCAGATCTAGGACCCATTTTAT, each DNA was phosphorylated with T4 polynuclectide kinase) including BglII restriction site and 91bp DdeI-EcoRI DNA coding for Glu$^{175}$-Trp$^{204}$ from pTTkPAΔtrp with T4 DNA ligase to give pHS9006. pTTkPAΔtrp was digested with EcoRI (partial) and ApaI. The 78 kbp DNA fragment was isolated and ligated to 4.1 kbp EcoRI-ApaI DNA fragment from pHS9006 to give pHS3020 coding for Arg$^{-1}$ plus Ser$^{174}$-Pro$^{527}$.

pHS3020 was digested with BglII and SmaI. The small DNA fragment coding for Arg$^{-1}$ plus Ser$^{174}$-Pro$^{508}$ was isolated and ligated to the BglII-SmaI large DNA fragment from pmTQk112 to give pmTTk, an expression vector for TTktPA in mammalian cell.

EXAMPLE 32

(Construction and cloning of pmSTTk)

Figure 27:
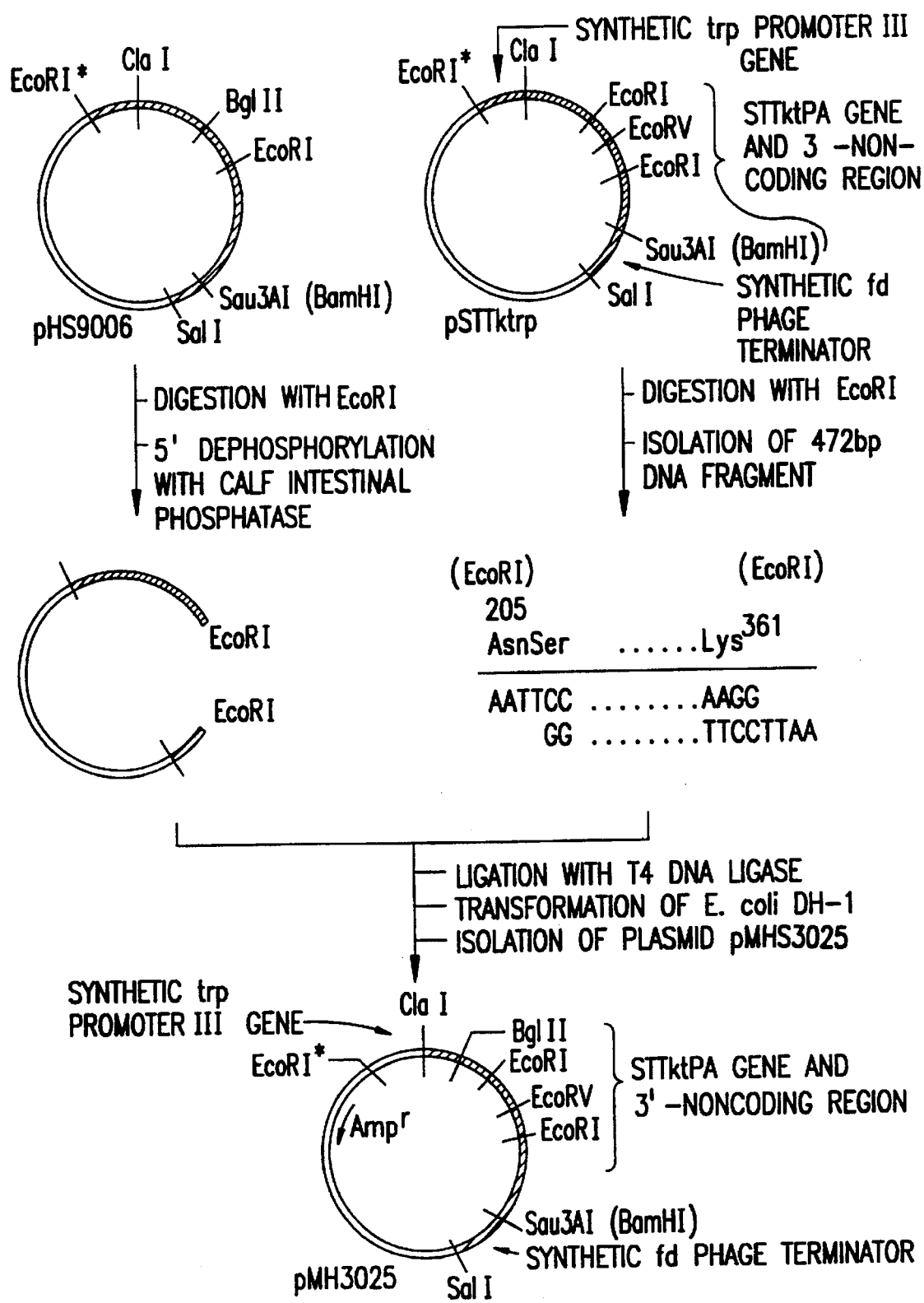
FIG. 27 shows construction and cloning of plasmid pMH3025.
Figure 28:
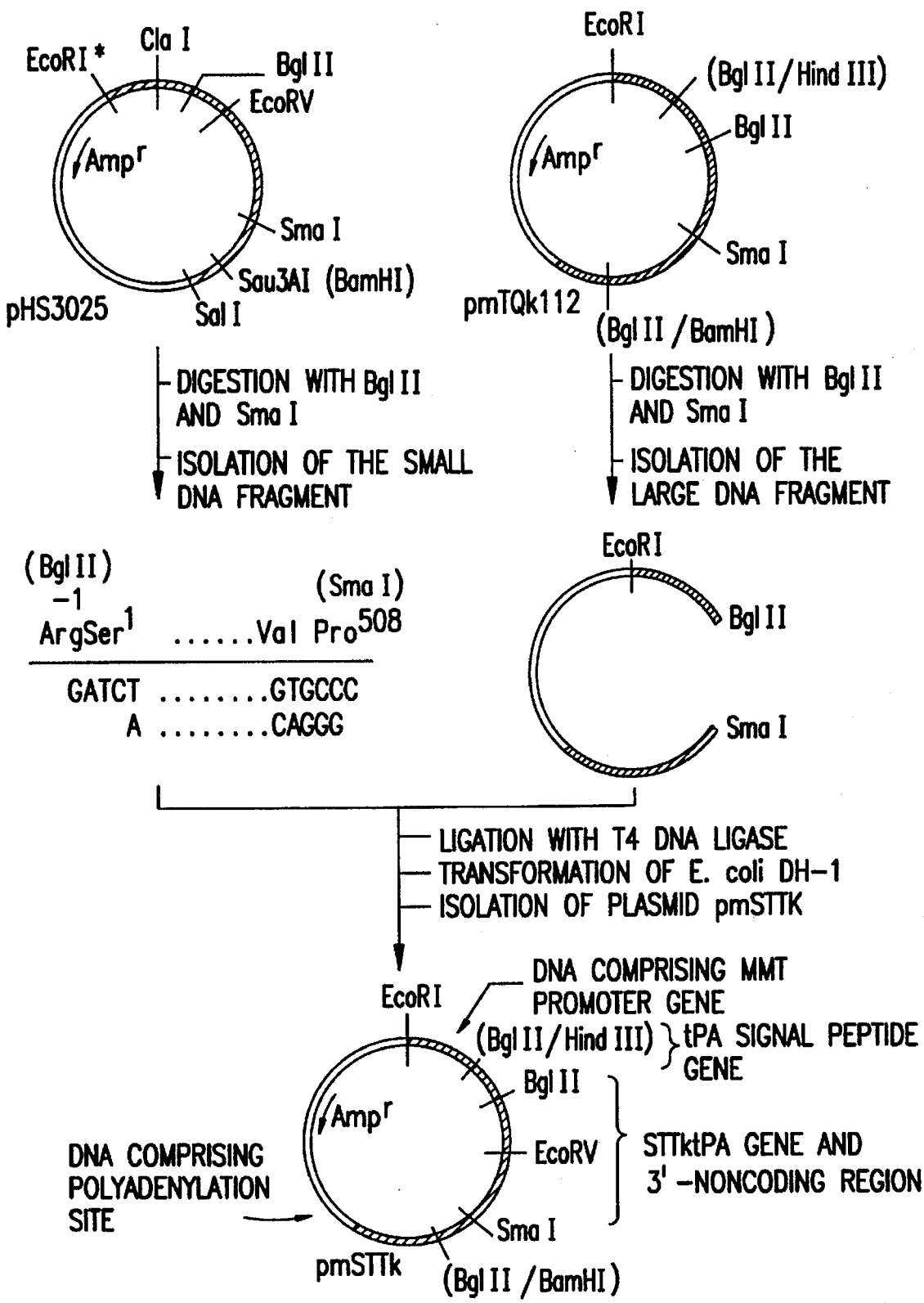
FIG. 28 shows construction and cloning of plasmid pmSTTk.

(as illustrated in FIGS. 27 and 28)

pHS9006 was digested with EcoRI. The large DNA fragment was isolated, dephosphorylated with calf intestinal phosphatase (Pharmacia) and ligated to the 472bp EcoRI DNA coding for Asn$^{205}$-Asp$^{275}$-Lys$^{361}$ from pSTTkΔtrp to give pMH3025. pMH3025 was digested with BglII and SmaI. The small DNA fragment was isolated and ligated to the large fragment BglII-SmaI DNA from pmTQk112 to give pmSTTk, an expression vector for STTktPA in mammalian cell.

EXAMPLE 33

(Expression)
Construction of L-929 Transformants
A. Preparation of the Cells

A culture of L-929 cell line was used in this example. L-929 cells can be generated from ATCC #CCL-1, and were maintained in DMEM containing kanamycin and 10% (vol/vol) fetal calf serum at 37° C. in 5% $CO_2$. These cells were plated in a cell density of 5×10$^5$ per 10 cm petri dish on the day before transformation, and provided 50–60% confluency on the day transformation. The media was changed three hours before the transformation. Two 10 cm petri dishes of cells were used to each transformation.

B. Preparation of the DNA solution

Plasmid DNA was introduced into L-929 cells using a calcium phosphate technique in a similar manner to that described in Gorman, DNA Cloning II, 143 (1985), IRL press.

Thirty μg of the expression plasmid (pmTQk112, pmTTk or pmSTTk) plus 3 μg of plasmid pSV2neo ATCC No. 37149 was added to 186 μl of 2M $CaCl_2$ and 1.3 ml of water. 1.5 ml of the DNA solution was then added dropwise to 1.5 ml of 2×HBS (1.63% NaCl, 1.19% Hepes, 0.04% $Na_2HPO_4$ pH 7.12) under bubbling. The mixture was allowed to stand 30 minutes at room temperature before it was added to the cells.

C. Transfection of the cells

The 0.6 ml of the DNA solution was added to a 10 cm petri dish of L-929 cells with gentle agitation and incubated at 37° C. for 18 hours in a $CO_2$ incubator. The cells were washed twice with DMEM. Complete fresh growth media containing 10% FCS was then added, and the cells were incubated at 37° C. for 24 hours in a $CO_2$ incubator. The cells were trypsinized and subcultured 1:10 into selective medium composed of DMEM containing 300 μg/ml geneticin (G418) and 10% FCS.

Cells which express the phosphotransferase (neo$^r$ gene product) can survive in the selective media and form colonies. Medium was changed every 3–4 days and colonies were isolated after 12–14 days. G418 resistant colonies were picked up by mild trypsinization in small cylinders, grown to mass cultures and tested for the secretion of mutant t-PA. The cells were grown in 1.7 cm diameter muti-well plate dishes with 3 ml Of the medium to a total of about 3×10$^5$ cells. Medium was removed and washed with PBS. Cells were cultured in 1 ml of inducible culture media composed of DMEM containing 0.04 mM $ZnSO_4$, 1 mM sodium butylate and 2% FCS at 37° C. for 24 hours and activity of mutant t-PA in the medium was confirmed an indirect spectrophotometric assay using the chromogenic agent S2251 [Cf. Thrombosis Research 31, 427 (1983)].

*E. coli* DH-1 was transformed with the plasmid, pmTQk112, pmTTk or pmSTTk for the purpose of the deposit in a conventional manner.

The following microorganisms shown in the above Examples have been desposited with one of the INTERNATIONAL DEPOSITORY AUTHORITY ON THE BUDAPEST TREATY, Fermentation Research Institute, Agency of Industrial Science and Technology residing at 1–3, Higashi 1 chome, Tsukuba-shi, Ibaraki-ken305, Japan since Jul. 30, Oct. 13 and Nov. 5, 1987 and Jul., 1988, and were assigned the following deposit numbers, respectively.

| Microorganisms | Deposit number |
| --- | --- |
| *Escherichia coli* HB101-16 | FERM BP-1872 |
| *Escherichia coli* HB101-16 (pTTkPAΔtrp) | FERM BP-1871 |
| *Escherichia coli* HB101-16 (pTTiPAΔtrp) | FERM BP-1869 |
| *Escherichia coli* HB101-16 (pTQiPAΔtrp) | FERM BP-1870 |
| *Escherichia coli* HB101-16 (pTQkPAΔtrp) | FERM BP-1521 |
| *Escherichia coli* HB101-16 (pSTTktrp) | FERM BP-1517 |
| *Escherichia coli* HB101-16 (pSTQitrp) | FERM BP-1516 |
| *Escherichia coli* HB101-16 (pSTQktrp) | FERM BP-1518 |
| *Escherichia coli* HB101-16 (pthTTtrp) | FERM BP-1562 |
| *Escherichia coli* HB101-16 (puTTtrp) | FERM BP-1519 |
| *Escherichia coli* DH-1 (pST112) | FERM BP-1966 |
| *Escherichia coli* DH-1 (pmTQk112) | FERM BP-1965 |
| *Escherichia coli* DH-1 (pmTTk) | FERM BP-1967 |
| *Escherichia coli* DH-1 (pmSTTk) | FERM BP-1964 |

We claim:

1. A non-glycosylated tissue plasminogen activator represented by the following amino acid sequence (I) as its primary structure:

```
                    180                        190
R—GluGlyAsnSerAspCysTyrPheGlyAsnGlySer AlaTyrArgGlyThrHis Ser 200                        210
   LeuThrGluSerGlyAlaSerCysLeuProTrpAsnSerMetIleLeuIleGlyLysVal 220                        230
   TyrThrAlaGlnAsnProSerAlaGlnAlaLeuGlyLeuGlyLysHisAsnTyrCysArg 240                        250
   AsnProAspGlyAspAlaLysProTrpCysHisValLeuLysAsnArgArgLeuThrTrp 260                        270
   GluTyrCysAspValProSerCysSerSerThrCysGlyLeuArgGln—Y—

277      280                        290
   —X—GlyGlyLeuPheAlaAspIleAlaSerHis ProTrpGlnAlaAlaIle 300                        310
   PheAlaLysHisArgArgSerProGlyGluArgPheLeuCysGlyGlyIleLeuIleSer 320                        330
   SerCysTrpIleLeuSerAlaAlaHisCysPheGlnGluArgPheProProHisHisLeu 340                        350
   ThrValIleLeuGlyArgThrTyrArgValValProGluGluGluGluGlnLysPheGlu 360                        370
   ValGluLysTyrIleValHisLysGluPheAspAspAspThrTyrAspAsnAspIleAla
```

-continued

```
                    380                           390
LeuLeuGlnLeuLysSerAspSerSerArgCysAlaGlnGluSerSerValValArgThr 400                           410
ValCysLeuProProAlaAspLeuGlnLeuProAspTrpThrGluCysGluLeuSerGly 420                           430
TyrGlyLysHisGluAlaLeuSerProPheTyrSerGluArgLeuLysGluAlaHisVal 440                           450
ArgLeuTyrProSerSerArgCysThrSerGlnHisLeuLeuAsnArgThrValThrAsp 460                           470
AsnMetLeuCysAlaGlyAspThrArgSerGlyGlyProGlnAlaAsnLeuHisAspAla 480                           490
CysGlnGlyAspSerGlyGlyProLeuValCysLeuAsnAspGlyArgMetThrLeuVal 500                           510
GlyIleIleSerTrpGlyLeuGlyCysGlyGlnLysAspValProGlyValTyrThrLys 520            527
ValThrAsnTyrLeuAspTrpIleArgAspAsnMetArgPro
``` wherein R is Ser—,

X is -Lys- and
Y is -TyrSerGlnProGlnPheArgIle- or -TyrSerGlnProGlnPheAspIle-.

2. The non-glycosylated tissue plasminogen activator of claim 1, in which R is Ser-, X is -Lys- and Y is -TyrSerGlnProGlnPheAspIle-.

3. The non-glycosylated plasminogen activator of claim 1, in which R is Ser-, X is -Lys- and Y is TyrSerGlnProGln-PheArgIle.

4. A isolated DNA encoding amino acid sequence (I) as defined in claim 1.

5. An expression vector of DNA encoding amino acid sequence (I) as defined in claim 1 wherein the sequence is expressed in *Escherichia coli*.

6. An *Escherichia coli* transformed with an expression vector of DNA sequence encoding amino acid sequence (I) as defined in claim 1.

7. A process for the production of tissue plasminogen a activator of claim 1 which comprises, culturing an *Escherichia coli* transformed with an expression vector of DNA encoding an amino acid sequence (I) as defined in claim 1 in a nutrient medium, and recovering the resultant t-PA from the cultured broth.

8. A pharmaceutical composition comprising tissue plasminogen activator of claim 1 and pharmaceutically acceptable carrier(s).

9. A tissue plasminogen activator expressed by a recombinant microorganism, lacking finger, growth factor and kringle 1 domains which further lacks glycosylation.

10. A process for the production of the tissue plasminogen activator of claim 9 which comprises, culturing *Escherichia coli* transformed with an expression vector of DNA encoding the tissue plasminogen activator of claim 9 in a nutrient medium, and recovering the resultant tissue plasminogen activator from the cultured broth.

11. A pharmaceutical composition comprising the tissue plasminogen activator of claim 9 and a pharmaceutically acceptable carrier.

12. A tissue plasminogen activator expressed by a recombinant microorganism, lacking finger, growth factor and kringle 1 domains which further lacks glycosylation, in which arginine residue at 275 position of native human tissue plasminogen activator is replaced by another amino acid residue.

13. A process for the production of the tissue plasminogen activator of claim 12 which comprises, culturing *Escherichia coli* transformed with an expression vector of DNA encoding the tissue plasminogen activator of claim 12 in a nutrient medium, and recovering the resultant tissue plasminogen activator from the cultured broth.

14. A pharmaceutical composition comprising the tissue plasminogen activator of claim 12 and pharmaceutically acceptable carrier.

15. The tissue plasminogen activator of claim 12 in which an arginine residue at 275 position of native human tissue plasminogen activator is replaced by an aspartic acid residue.

16. A process for the production of the tissue plasminogen activator of claim 15 which comprises, culturing *Escherichia coli* transformed with an expression vector of DNA encoding the tissue plasminogen activator of claim 15 in a nutrient medium, and recovering the resultant tissue plasminogen activator from the cultured broth.

17. A pharmaceutical composition comprising the tissue plasminogen activator of claim 15 and a pharmaceutically acceptable carrier.

* * * * *